US012558468B2

(12) United States Patent
Jensen et al.

(10) Patent No.: US 12,558,468 B2
(45) Date of Patent: Feb. 24, 2026

(54) BLOOD TREATMENT SYSTEMS

(71) Applicants: FRESENIUS MEDICAL CARE HOLDINGS, INC., Waltham, MA (US); FRESENIUS MEDICAL CARE DEUTSCHLAND GMBH, Bad Homburg (DE)

(72) Inventors: Lynn E. Jensen, Waltham, MA (US); Stephen A. Merchant, Waltham, MA (US); Arne Peters, Bad Homburg (DE); Alexander Heide, Bad Homburg (DE); Dejan Nikolic, Bad Homburg (DE)

(73) Assignees: Fresenius Medical Care Holdings, Inc., Waltham, MA (US); Fresenius Medical Care Deutschland GmbH, Bad Homburg (DE)

( * ) Notice: Subject to any disclaimer, the term of this patent is extended or adjusted under 35 U.S.C. 154(b) by 757 days.

(21) Appl. No.: 17/782,752

(22) PCT Filed: Dec. 11, 2020

(86) PCT No.: PCT/US2020/064462
§ 371 (c)(1),
(2) Date: Jun. 6, 2022

(87) PCT Pub. No.: WO2021/119401
PCT Pub. Date: Jun. 17, 2021

(65) Prior Publication Data
US 2023/0019233 A1      Jan. 19, 2023

Related U.S. Application Data

(60) Provisional application No. 62/947,285, filed on Dec. 12, 2019.

(51) Int. Cl.
A61M 1/16 (2006.01)
A61M 1/14 (2006.01)
(Continued)

(52) U.S. Cl.
CPC .......... A61M 1/1656 (2013.01); A61M 1/152 (2022.05); A61M 1/153 (2022.05);
(Continued)

(58) Field of Classification Search
None
See application file for complete search history.

(56) References Cited

U.S. PATENT DOCUMENTS

| | | | |
|---|---|---|---|
| 2,530,581 A | 11/1950 | Markis et al. | |
| 3,973,683 A | 8/1976 | Keller | |
| | (Continued) | | |

FOREIGN PATENT DOCUMENTS

| | | |
|---|---|---|
| AU | 2016201358 | 5/2016 |
| CN | 103751869 | 4/2014 |
| | (Continued) | |

OTHER PUBLICATIONS

Machine translation of DE-3923692-A1, pp. 1-5. (Year: 1991).*
(Continued)

*Primary Examiner* — Clare M Perrin
(74) *Attorney, Agent, or Firm* — Fish & Richardson P.C.

(57) ABSTRACT

In one aspect, a system includes a blood treatment machine; a dialyzer configured to be coupled to the blood treatment machine, the dialyzer including a dialyzer housing defining a blood inlet and a blood outlet; a bundle of hollow fibers within an interior of the dialyzer housing; a pumping device drivable to force blood received from the blood inlet through lumens of the bundle of hollow fibers and out the blood outlet; a dialysate inlet port in fluid communication with a dialysate flow path that includes space in the interior of the dialyzer housing between the bundle of hollow fibers; and a dialysate outlet port in fluid communication with the dialysate flow path. The system further includes a fluid conditioning system configured to (i) prepare and supply
(Continued)

fresh dialysate to the dialyzer via the dialysate inlet port, and (ii) receive spent dialysate from the dialyzer via the dialysate outlet port, recycle the spent dialysate, and supply the recycled dialysate to the dialyzer via the dialysate inlet port.

23 Claims, 43 Drawing Sheets

(51) Int. Cl.
  *A61M 1/34* (2006.01)
  *A61M 1/36* (2006.01)
  *A61M 39/22* (2006.01)
(52) U.S. Cl.
  CPC ............ *A61M 1/154* (2022.05); *A61M 1/155* (2022.05); *A61M 1/1561* (2022.05); *A61M 1/1565* (2022.05); *A61M 1/159* (2022.05); *A61M 1/166* (2014.02); *A61M 1/1696* (2013.01); *A61M 1/3434* (2014.02); *A61M 1/3643* (2013.01); *A61M 39/223* (2013.01); *A61M 2205/128* (2013.01); *A61M 2205/3317* (2013.01); *A61M 2205/3331* (2013.01); *A61M 2205/3368* (2013.01); *A61M 2205/3584* (2013.01); *A61M 2205/3592* (2013.01); *A61M 2205/3653* (2013.01); *B01D 2313/18* (2013.01); *B01D 2313/243* (2013.01)

(56) References Cited

U.S. PATENT DOCUMENTS

| | | | |
|---|---|---|---|
| 4,001,556 A | 1/1977 | Folchi et al. | |
| 4,035,115 A | 7/1977 | Hansen | |
| 4,183,723 A | 1/1980 | Hansen et al. | |
| 4,211,597 A | 7/1980 | Lipps et al. | |
| 4,229,136 A | 10/1980 | Panissidi | |
| 4,231,871 A | 11/1980 | Lipps et al. | |
| 4,274,802 A | 6/1981 | Inaba et al. | |
| 4,287,059 A | 9/1981 | Kume et al. | |
| 4,363,585 A | 12/1982 | Keller et al. | |
| 4,575,324 A | 3/1986 | Sommer et al. | |
| 4,687,941 A | 8/1987 | Laserberg et al. | |
| 4,762,480 A | 8/1988 | Winkler et al. | |
| 4,936,744 A | 6/1990 | Dosch et al. | |
| 5,011,380 A | 4/1991 | Kovacs | |
| 5,087,070 A | 2/1992 | O'Loughlin et al. | |
| 5,111,997 A | 5/1992 | Ikuta et al. | |
| 5,302,929 A | 4/1994 | Kovacs | |
| 5,308,314 A | 5/1994 | Fukui et al. | |
| 5,322,413 A | 6/1994 | Vescovini et al. | |
| 5,328,461 A | 7/1994 | Utterberg | |
| 5,330,425 A | 7/1994 | Utterberg | |
| 5,360,317 A | 11/1994 | Clausen et al. | |
| 5,458,459 A | 10/1995 | Hubbard et al. | |
| 5,520,640 A | 5/1996 | Utterberg | |
| 5,540,668 A | 7/1996 | Wilson, Jr. et al. | |
| 5,575,630 A | 11/1996 | Nakazawa et al. | |
| 5,622,468 A | 4/1997 | Viollet | |
| 5,679,906 A | 10/1997 | Van Cleve et al. | |
| 5,683,231 A | 11/1997 | Nakazawa et al. | |
| 5,695,471 A | 12/1997 | Wampler | |
| 5,725,357 A | 3/1998 | Nakazeki et al. | |
| 5,728,951 A | 3/1998 | Van Cleve et al. | |
| 5,769,815 A | 6/1998 | Utterberg | |
| 5,770,149 A | 6/1998 | Raible | |
| 5,810,758 A | 9/1998 | Yamazaki et al. | |
| 5,840,070 A | 11/1998 | Wampler | |
| 5,895,571 A | 4/1999 | Utterberg | |
| 5,941,813 A | 8/1999 | Sievers et al. | |
| 5,980,741 A | 11/1999 | Schnell et al. | |
| 5,983,947 A | 11/1999 | Utterberg | |
| 6,010,623 A | 1/2000 | Schnell et al. | |
| 6,019,824 A | 2/2000 | Schnell | |
| 6,051,134 A | 4/2000 | Schnell et al. | |
| 6,068,455 A | 5/2000 | Cowans | |
| 6,074,180 A | 6/2000 | Khanwilkar et al. | |
| 6,080,133 A | 6/2000 | Wampler | |
| 6,093,001 A | 7/2000 | Burgreen et al. | |
| 6,100,618 A | 8/2000 | Schoeb et al. | |
| 6,117,342 A | 9/2000 | Schnell et al. | |
| 6,158,984 A | 12/2000 | Cao et al. | |
| 6,183,220 B1 | 2/2001 | Ohara et al. | |
| 6,224,829 B1 | 5/2001 | Piplani et al. | |
| 6,227,797 B1 | 5/2001 | Watterson et al. | |
| 6,227,817 B1 | 5/2001 | Paden | |
| 6,234,998 B1 | 5/2001 | Wampler | |
| 6,250,880 B1 | 6/2001 | Woodard et al. | |
| 6,251,292 B1 | 6/2001 | Zuk, Jr. | |
| 6,274,055 B1 | 8/2001 | Zuk, Jr. | |
| 6,302,661 B1 | 10/2001 | Khanwilkar et al. | |
| 6,368,083 B1 | 4/2002 | Wampler | |
| 6,368,557 B1 | 4/2002 | Piplani et al. | |
| 6,379,618 B1 | 4/2002 | Piplani et al. | |
| 6,394,769 B1 | 5/2002 | Bearnson et al. | |
| 6,398,955 B1 | 6/2002 | Fumiyama et al. | |
| 6,402,818 B1 | 6/2002 | Sengupta | |
| 6,428,747 B1 | 8/2002 | Dueri et al. | |
| 6,431,826 B1 | 8/2002 | Schober | |
| 6,454,999 B1 | 9/2002 | Farhangnia et al. | |
| 6,468,041 B2 | 10/2002 | Ozaki | |
| 6,478,962 B1 | 11/2002 | Brockhoff et al. | |
| 6,503,450 B1 | 1/2003 | Afzal et al. | |
| 6,517,508 B1 | 2/2003 | Utterberg et al. | |
| 6,517,732 B1 | 2/2003 | Brockhoff et al. | |
| 6,547,530 B2 | 4/2003 | Ozaki et al. | |
| 6,575,717 B2 | 6/2003 | Ozaki et al. | |
| 6,589,030 B2 | 7/2003 | Ozaki | |
| 6,595,762 B2 | 7/2003 | Khanwilkar et al. | |
| 6,596,058 B2 | 7/2003 | Gerner et al. | |
| 6,609,883 B2 | 8/2003 | Woodard et al. | |
| 6,638,011 B2 | 10/2003 | Woodard et al. | |
| 6,688,861 B2 | 2/2004 | Wampler | |
| 6,718,827 B1 | 4/2004 | Lee et al. | |
| 6,725,726 B1 | 4/2004 | Adolfs et al. | |
| 6,746,416 B2 | 6/2004 | Hubbard et al. | |
| 6,820,490 B2 | 11/2004 | Mittelstein et al. | |
| 6,840,735 B2 | 1/2005 | Yaegashi et al. | |
| 6,866,625 B1 | 3/2005 | Ayre et al. | |
| 6,880,404 B2 | 4/2005 | Uberreiter | |
| 6,884,210 B2 | 4/2005 | Nose et al. | |
| 6,887,214 B1 | 5/2005 | Levin et al. | |
| 6,939,111 B2 | 9/2005 | Huitt et al. | |
| 6,942,447 B2 | 9/2005 | Ikeya | |
| 6,966,748 B2 | 11/2005 | Woodard et al. | |
| 7,021,148 B2 | 4/2006 | Kuhn et al. | |
| 7,022,099 B2 | 4/2006 | Litzie et al. | |
| 7,025,750 B2 | 4/2006 | Brugger et al. | |
| 7,033,147 B2 | 4/2006 | Yanai et al. | |
| 7,156,802 B2 | 1/2007 | Woodard et al. | |
| 7,160,242 B2 | 1/2007 | Yanai | |
| 7,162,884 B2 | 1/2007 | Alles | |
| 7,216,672 B1 | 5/2007 | Chen | |
| 7,220,354 B2 | 5/2007 | McLaughlin et al. | |
| 7,357,858 B2 | 4/2008 | Schoeb | |
| 7,422,565 B2 | 9/2008 | Delnevo et al. | |
| 7,462,019 B1 | 12/2008 | Allarie et al. | |
| 7,470,246 B2 | 12/2008 | Mori et al. | |
| 7,476,077 B2 | 1/2009 | Woodard et al. | |
| 7,513,163 B2 | 4/2009 | Fukutomi et al. | |
| 7,556,611 B2 | 7/2009 | Kolenbrander et al. | |
| 7,575,423 B2 | 8/2009 | Wampler | |
| 7,603,907 B2 | 10/2009 | Reiter et al. | |
| 7,648,627 B2 | 1/2010 | Beden et al. | |
| 7,748,275 B2 | 7/2010 | Kouda et al. | |
| 7,748,964 B2 | 7/2010 | Yaegashi et al. | |
| 7,767,447 B2 | 8/2010 | Breidenthal et al. | |
| 7,776,006 B2 | 8/2010 | Childers et al. | |
| 7,780,336 B2 | 8/2010 | Breidenthal et al. | |
| 7,798,985 B2 | 9/2010 | Engelhardt et al. | |
| 7,803,628 B2 | 9/2010 | Glocker | |
| 7,871,391 B2 | 1/2011 | Folden et al. | |
| 7,871,462 B2 | 1/2011 | Yardimci et al. | |

(56) References Cited

U.S. PATENT DOCUMENTS

| | | | |
|---|---|---|---|
| 7,892,331 | B2 | 2/2011 | Childers et al. |
| 7,892,332 | B2 | 2/2011 | Prisco et al. |
| 7,901,579 | B2 | 3/2011 | Brugger et al. |
| 7,921,723 | B2 | 4/2011 | Reiter et al. |
| 7,976,271 | B2 | 7/2011 | LaRose et al. |
| 7,988,768 | B2 | 8/2011 | Yardimci et al. |
| 7,997,854 | B2 | 8/2011 | LaRose et al. |
| 8,002,518 | B2 | 8/2011 | Woodard et al. |
| 8,025,714 | B2 | 9/2011 | Prisco et al. |
| 8,025,716 | B2 | 9/2011 | Prisco et al. |
| 8,029,454 | B2 | 10/2011 | Kelly et al. |
| 8,034,161 | B2 | 10/2011 | Gura et al. |
| 8,038,639 | B2 | 10/2011 | Lo et al. |
| 8,043,074 | B2 | 10/2011 | Tada |
| 8,048,209 | B2 | 11/2011 | Dannenmaier et al. |
| 8,048,375 | B2 | 11/2011 | Breidenthal et al. |
| 8,052,929 | B2 | 11/2011 | Breidenthal et al. |
| 8,096,186 | B2 | 1/2012 | Butterfield |
| 8,104,352 | B2 | 1/2012 | Evering et al. |
| 8,105,265 | B2 | 1/2012 | Demers et al. |
| 8,113,060 | B2 | 2/2012 | Jonsson et al. |
| 8,114,276 | B2 | 2/2012 | Childers et al. |
| 8,123,503 | B2 | 2/2012 | Shinshi et al. |
| 8,142,383 | B2 | 3/2012 | Dannenmaier et al. |
| 8,162,152 | B2 | 4/2012 | Omori et al. |
| 8,167,593 | B2 | 5/2012 | Gohean et al. |
| 8,192,388 | B2 | 6/2012 | Hogard |
| 8,206,580 | B2 | 6/2012 | Dannenmaier et al. |
| 8,221,529 | B2 | 7/2012 | Childers et al. |
| 8,221,705 | B2 | 7/2012 | Breidenthal et al. |
| 8,226,373 | B2 | 7/2012 | Yaegashi |
| 8,282,359 | B2 | 10/2012 | Ayre et al. |
| 8,282,366 | B2 | 10/2012 | Hilber et al. |
| 8,323,492 | B2 | 12/2012 | Childers et al. |
| 8,329,030 | B2 | 12/2012 | Childers et al. |
| 8,333,118 | B2 | 12/2012 | Blankenship |
| 8,353,686 | B2 | 1/2013 | Cook |
| 8,366,381 | B2 | 2/2013 | Woodard et al. |
| 8,382,711 | B2 | 2/2013 | Dudar et al. |
| 8,403,150 | B2 | 3/2013 | Dannenmaier et al. |
| 8,414,686 | B2 | 4/2013 | Gura et al. |
| 8,419,709 | B2 | 4/2013 | Haddad et al. |
| 8,430,652 | B2 | 4/2013 | Yaegashi et al. |
| 8,444,586 | B2 | 5/2013 | Beck |
| 8,480,976 | B2 | 7/2013 | Breidenthal et al. |
| 8,485,999 | B2 | 7/2013 | Holmer et al. |
| 8,491,178 | B2 | 7/2013 | Breidenthal et al. |
| 8,496,874 | B2 | 7/2013 | Gellman et al. |
| 8,512,013 | B2 | 8/2013 | LaRose et al. |
| 8,540,477 | B2 | 9/2013 | LaRose et al. |
| 8,545,427 | B2 | 10/2013 | Holmer et al. |
| 8,555,926 | B2 | 10/2013 | MacDuff et al. |
| 8,561,471 | B2 | 10/2013 | Blankenship |
| 8,568,347 | B2 | 10/2013 | Brieske et al. |
| 8,580,110 | B2 | 11/2013 | Jonsson et al. |
| 8,596,999 | B2 | 12/2013 | Shinshi et al. |
| 8,640,547 | B2 | 2/2014 | Winkler et al. |
| 8,641,657 | B2 | 2/2014 | Ribolzi et al. |
| 8,652,082 | B2 | 2/2014 | Jonsson et al. |
| 8,657,733 | B2 | 2/2014 | Ayre et al. |
| 8,672,611 | B2 | 3/2014 | LaRose et al. |
| 8,708,943 | B2 | 4/2014 | Caleffi et al. |
| D705,432 | S | 5/2014 | Lura et al. |
| 8,735,055 | B2 | 5/2014 | Breidenthal et al. |
| 8,765,367 | B2 | 7/2014 | Breidenthal et al. |
| 8,770,945 | B2 | 7/2014 | Ozaki et al. |
| 8,784,083 | B2 | 7/2014 | Dippel |
| 8,784,745 | B2 | 7/2014 | Nelson et al. |
| 8,803,044 | B2 | 8/2014 | Kienman et al. |
| 8,821,365 | B2 | 9/2014 | Ozaki et al. |
| 8,827,661 | B2 | 9/2014 | Mori |
| 8,827,663 | B2 | 9/2014 | Cook |
| 8,828,654 | B2 | 9/2014 | Nelson et al. |
| 8,834,403 | B2 | 9/2014 | Kelly et al. |
| 8,834,719 | B2 | 9/2014 | Childers et al. |
| D714,944 | S | 10/2014 | Gerber et al. |
| 8,858,487 | B2 | 10/2014 | Suzuki |
| 8,858,488 | B2 | 10/2014 | Kelly et al. |
| 8,870,552 | B2 | 10/2014 | Ayre et al. |
| 8,870,804 | B2 | 10/2014 | Jonsson |
| 8,876,685 | B2 | 11/2014 | Crosby et al. |
| 8,882,692 | B2 | 11/2014 | Lo et al. |
| 8,888,470 | B2 | 11/2014 | Demers et al. |
| 8,894,600 | B2 | 11/2014 | Kelly et al. |
| D720,462 | S | 12/2014 | Lura et al. |
| 8,906,300 | B2 | 12/2014 | Wang et al. |
| D721,815 | S | 1/2015 | Lura et al. |
| 8,926,540 | B2 | 1/2015 | Lo et al. |
| 8,926,544 | B2 | 1/2015 | Hogard |
| 8,932,006 | B2 | 1/2015 | LaRose et al. |
| 8,932,469 | B2 | 1/2015 | Childers et al. |
| 8,939,926 | B2 | 1/2015 | Wieting et al. |
| 8,945,037 | B2 | 2/2015 | Hasegawa et al. |
| 8,951,220 | B2 | 2/2015 | Brieske et al. |
| 8,968,232 | B2 | 3/2015 | Kamen et al. |
| 8,974,405 | B2 | 3/2015 | Folden et al. |
| 8,985,969 | B2 | 3/2015 | Hoshi et al. |
| 8,992,075 | B2 | 3/2015 | Kamen et al. |
| 8,992,463 | B2 | 3/2015 | Hogard et al. |
| 9,005,152 | B2 | 4/2015 | Kelly et al. |
| 9,028,436 | B2 | 5/2015 | Lo et al. |
| 9,028,691 | B2 | 5/2015 | Grant et al. |
| 9,032,818 | B2 | 5/2015 | Campbell et al. |
| 9,039,595 | B2 | 5/2015 | Ayre et al. |
| 9,039,648 | B2 | 5/2015 | Kelly et al. |
| 9,044,535 | B2 | 6/2015 | Garzaniti et al. |
| 9,050,405 | B2 | 6/2015 | LaRose et al. |
| 9,050,411 | B2 | 6/2015 | Kelly et al. |
| 9,050,417 | B2 | 6/2015 | Fini et al. |
| 9,067,005 | B2 | 6/2015 | Ozaki et al. |
| 9,068,572 | B2 | 6/2015 | Ozaki et al. |
| 9,072,830 | B2 | 7/2015 | Kelly et al. |
| 9,072,831 | B2 | 7/2015 | Kelly et al. |
| 9,072,843 | B2 | 7/2015 | Kelly et al. |
| 9,089,635 | B2 | 7/2015 | Reichenbach et al. |
| 9,109,601 | B2 | 8/2015 | Mori |
| 9,127,680 | B2 | 9/2015 | Yanai et al. |
| 9,132,215 | B2 | 9/2015 | Ozaki et al. |
| 9,133,847 | B2 | 9/2015 | Hijikata et al. |
| 9,133,854 | B2 | 9/2015 | Okawa et al. |
| 9,144,641 | B2 | 9/2015 | Kelly et al. |
| 9,155,825 | B2 | 10/2015 | Kelly et al. |
| 9,164,008 | B2 | 10/2015 | Fukano et al. |
| 9,168,333 | B2 | 10/2015 | Kelly et al. |
| D742,527 | S | 11/2015 | Gerber et al. |
| 9,173,986 | B2 | 11/2015 | Heide et al. |
| 9,173,987 | B2 | 11/2015 | Meyer et al. |
| 9,180,237 | B2 | 11/2015 | Giordano et al. |
| 9,216,246 | B2 | 12/2015 | Kelly et al. |
| 9,239,057 | B2 | 1/2016 | Hoshi et al. |
| 9,242,032 | B2 | 1/2016 | LaRose et al. |
| 9,272,082 | B2 | 3/2016 | Demers et al. |
| 9,278,168 | B2 | 3/2016 | Gellman et al. |
| 9,302,039 | B2 | 4/2016 | Kelly et al. |
| 9,360,003 | B2 | 6/2016 | Oerter |
| 9,364,599 | B2 | 6/2016 | Giordano et al. |
| 9,364,602 | B2 | 6/2016 | Kelly et al. |
| 9,371,826 | B2 | 6/2016 | Yanai et al. |
| 9,381,285 | B2 | 7/2016 | Ozaki et al. |
| 9,382,908 | B2 | 7/2016 | Ozaki et al. |
| 9,387,286 | B2 | 7/2016 | Kelly et al. |
| 9,403,126 | B2 | 8/2016 | Fissell et al. |
| 9,404,825 | B2 | 8/2016 | Katz et al. |
| 9,410,549 | B2 | 8/2016 | Ozaki et al. |
| 9,415,150 | B2 | 8/2016 | Hogard et al. |
| 9,421,313 | B2 | 8/2016 | Kelly et al. |
| 9,429,160 | B2 | 8/2016 | Tanaka et al. |
| 9,433,880 | B2 | 9/2016 | Lean et al. |
| 9,435,706 | B2 | 9/2016 | Fini et al. |
| 9,446,181 | B2 | 9/2016 | Jonsson et al. |
| 9,458,451 | B2 | 10/2016 | Heinz et al. |
| 9,468,557 | B2 | 10/2016 | Wang et al. |
| 9,480,784 | B2 | 11/2016 | Kelly et al. |
| 9,512,852 | B2 | 12/2016 | Wampler et al. |

(56) References Cited

U.S. PATENT DOCUMENTS

| | | | |
|---|---|---|---|
| 9,526,822 | B2 | 12/2016 | Meyer et al. |
| 9,550,019 | B2 | 1/2017 | Buck et al. |
| 9,550,020 | B2 | 1/2017 | Kelly et al. |
| 9,555,182 | B2 | 1/2017 | Wieting et al. |
| 9,556,873 | B2 | 1/2017 | Yanai et al. |
| 9,572,919 | B2 | 2/2017 | Kelly et al. |
| 9,592,326 | B2 | 3/2017 | Takatani et al. |
| 9,597,442 | B2 | 3/2017 | Wilt |
| 9,603,985 | B2 | 3/2017 | Wilt et al. |
| 9,623,164 | B2 | 4/2017 | Meyer et al. |
| 9,638,202 | B2 | 5/2017 | Ozaki et al. |
| 9,642,961 | B2 | 5/2017 | Kelly et al. |
| 9,649,419 | B2 | 5/2017 | Giordano et al. |
| 9,649,420 | B2 | 5/2017 | Giordano et al. |
| 9,675,745 | B2 | 6/2017 | Kelly et al. |
| 9,700,662 | B2 | 7/2017 | Strohhoefer et al. |
| 9,709,061 | B2 | 7/2017 | Yanai et al. |
| 9,713,665 | B2 | 7/2017 | Meyer et al. |
| 9,717,837 | B2 | 8/2017 | Vincent |
| 9,744,506 | B2 | 8/2017 | Fan et al. |
| 9,764,074 | B1 | 9/2017 | Childers et al. |
| 9,777,732 | B2 | 10/2017 | LaRose et al. |
| 9,795,728 | B2 | 10/2017 | Grant et al. |
| 9,801,992 | B2 | 10/2017 | Giordano et al. |
| 9,802,158 | B2 | 10/2017 | Fissell et al. |
| 9,827,361 | B2 | 11/2017 | Pudil et al. |
| 9,835,158 | B2 | 12/2017 | Schob |
| 9,839,733 | B2 | 12/2017 | Reichenbach et al. |
| 9,850,906 | B2 | 12/2017 | Ozaki et al. |
| 9,855,377 | B2 | 1/2018 | Childers et al. |
| 9,872,949 | B2 | 1/2018 | Meyer et al. |
| 9,872,950 | B2 | 1/2018 | Kelly et al. |
| 9,877,476 | B2 | 1/2018 | Levesque et al. |
| 9,884,144 | B2 | 2/2018 | Lo et al. |
| 9,889,243 | B2 | 2/2018 | Kelly et al. |
| 9,901,666 | B2 | 2/2018 | Cotter |
| 9,925,320 | B2 | 3/2018 | Childers et al. |
| 9,931,447 | B2 | 4/2018 | Layser et al. |
| 9,945,838 | B2 | 4/2018 | Doyle |
| 9,962,629 | B2 | 5/2018 | Taylor et al. |
| 9,968,132 | B2 | 5/2018 | Hon |
| 9,987,407 | B2 | 6/2018 | Grant et al. |
| 9,995,310 | B2 | 6/2018 | Graichen |
| 10,010,663 | B2 | 7/2018 | Meyer et al. |
| 10,016,550 | B2 | 7/2018 | Giordano et al. |
| 10,030,664 | B2 | 7/2018 | Lin et al. |
| 10,058,694 | B2 | 8/2018 | Norris et al. |
| 10,080,834 | B2 | 9/2018 | Federspiel et al. |
| 10,086,342 | B2 | 10/2018 | Heinz et al. |
| 10,092,716 | B2 | 10/2018 | Velzy et al. |
| 10,098,998 | B2 | 10/2018 | Wilt |
| 10,143,787 | B2 | 12/2018 | Kumano |
| 10,143,790 | B2 | 12/2018 | Schiller et al. |
| 10,145,376 | B2 | 12/2018 | Kumano |
| 10,155,078 | B2 | 12/2018 | Giordano et al. |
| 10,155,080 | B2 | 12/2018 | Lo et al. |
| 10,166,318 | B2 | 1/2019 | Yu et al. |
| 10,172,989 | B2 | 1/2019 | Giordano et al. |
| 10,177,627 | B2 | 1/2019 | Noh et al. |
| 10,183,103 | B2 | 1/2019 | Wiktor et al. |
| 10,183,109 | B2 | 1/2019 | Kelly et al. |
| 10,188,784 | B2 | 1/2019 | Katz et al. |
| 10,226,565 | B2 | 3/2019 | Fini et al. |
| 10,245,361 | B2 | 4/2019 | Yanai et al. |
| 10,245,369 | B2 | 4/2019 | Kelly et al. |
| 10,245,370 | B2 | 4/2019 | Kelly et al. |
| 10,258,729 | B2 | 4/2019 | Gellman et al. |
| 10,265,449 | B2 | 4/2019 | Wampler et al. |
| 10,293,096 | B2 | 5/2019 | Kelly et al. |
| 10,300,184 | B2 | 5/2019 | Cotter |
| 10,357,599 | B2 | 7/2019 | Strohhoefer et al. |
| 10,369,265 | B2 | 8/2019 | Wieting et al. |
| 10,371,152 | B2 | 8/2019 | Yanai et al. |
| 10,389,207 | B2 | 8/2019 | Schoeb |
| 10,420,872 | B2 | 9/2019 | Meyer et al. |
| 10,426,883 | B2 | 10/2019 | Kelly et al. |
| 10,426,884 | B2 | 10/2019 | Labib et al. |
| 10,428,828 | B2 | 10/2019 | Canatella et al. |
| 10,441,697 | B2 | 10/2019 | Kamen et al. |
| 10,449,280 | B2 | 10/2019 | Wilt et al. |
| 10,473,105 | B2 | 11/2019 | Lin et al. |
| 10,500,327 | B2 | 12/2019 | Grant et al. |
| 10,532,141 | B2 | 1/2020 | Meyer et al. |
| 10,543,052 | B2 | 1/2020 | Meyer et al. |
| 10,543,301 | B2 | 1/2020 | Timms |
| 11,085,552 | B2 | 8/2021 | Moss et al. |
| 2003/0098270 | A1 | 5/2003 | Thompson |
| 2004/0221904 | A1 | 11/2004 | Usher et al. |
| 2005/0274658 | A1 | 12/2005 | Rosenbaum et al. |
| 2006/0222533 | A1 | 10/2006 | Reeves et al. |
| 2007/0272311 | A1 | 11/2007 | Trocki et al. |
| 2008/0172006 | A1 | 7/2008 | Hicks |
| 2008/0214979 | A1 | 9/2008 | Brugger et al. |
| 2009/0101552 | A1 | 4/2009 | Fulkerson et al. |
| 2010/0198129 | A1 | 8/2010 | Sternby et al. |
| 2010/0268145 | A1 | 10/2010 | Caleffi et al. |
| 2010/0312174 | A1 | 12/2010 | Hoffman |
| 2010/0326531 | A1 | 12/2010 | Oltman et al. |
| 2011/0283878 | A1 | 11/2011 | Romanin |
| 2012/0193563 | A1 | 8/2012 | Croci |
| 2012/0258545 | A1* | 10/2012 | Ash .................... A61M 1/1656 |
| | | | 210/85 |
| 2013/0126404 | A1 | 5/2013 | Gronau et al. |
| 2013/0177459 | A1 | 7/2013 | Weatherley |
| 2013/0180339 | A1 | 7/2013 | Brugger |
| 2013/0233798 | A1 | 9/2013 | Wiktor et al. |
| 2013/0269416 | A1 | 10/2013 | Myrick et al. |
| 2014/0088482 | A1 | 3/2014 | Schlaeper et al. |
| 2014/0097371 | A1 | 4/2014 | Huynh |
| 2014/0150559 | A1 | 6/2014 | Ishihara et al. |
| 2014/0217020 | A1 | 8/2014 | Meyer et al. |
| 2015/0247503 | A1 | 9/2015 | Seiss et al. |
| 2015/0285258 | A1 | 10/2015 | Foster |
| 2015/0343127 | A1 | 12/2015 | Childers et al. |
| 2016/0008529 | A1 | 1/2016 | Hoffman |
| 2016/0058995 | A1 | 3/2016 | Schriver et al. |
| 2016/0101226 | A1 | 4/2016 | Beiriger |
| 2016/0131141 | A1 | 5/2016 | Sato et al. |
| 2016/0239025 | A1 | 8/2016 | van der Merwe et al. |
| 2017/0106131 | A1 | 4/2017 | Hornig |
| 2017/0143886 | A1 | 5/2017 | Wilt et al. |
| 2017/0189598 | A1 | 7/2017 | Slade |
| 2017/0232173 | A1 | 8/2017 | Perry et al. |
| 2017/0319086 | A1 | 11/2017 | Masuda et al. |
| 2018/0024022 | A1 | 1/2018 | Beden |
| 2018/0080843 | A1 | 3/2018 | Funamura et al. |
| 2018/0185567 | A1 | 7/2018 | Madhani et al. |
| 2018/0207345 | A1 | 7/2018 | Peters |
| 2018/0229021 | A1 | 8/2018 | Donlon et al. |
| 2018/0280604 | A1 | 10/2018 | Hobro et al. |
| 2019/0105436 | A1 | 4/2019 | Uchida |
| 2019/0125946 | A1 | 5/2019 | Gartner et al. |
| 2019/0134289 | A1 | 5/2019 | Pudil et al. |
| 2019/0262523 | A1 | 8/2019 | Gomes, II |
| 2019/0356195 | A1 | 11/2019 | Holenstein |
| 2020/0030518 | A1 | 1/2020 | Brugger et al. |
| 2020/0033897 | A1 | 1/2020 | Jensen et al. |
| 2020/0041021 | A1 | 2/2020 | Moss et al. |
| 2020/0179674 | A1 | 6/2020 | Moss et al. |
| 2020/0271232 | A1 | 8/2020 | Nakagami et al. |
| 2020/0405941 | A1 | 12/2020 | Ikuma |
| 2021/0299340 | A1 | 9/2021 | Adams et al. |
| 2021/0341073 | A1 | 11/2021 | Moss et al. |

FOREIGN PATENT DOCUMENTS

| | | |
|---|---|---|
| CN | 103998909 | 8/2014 |
| CN | 104069558 | 10/2014 |
| CN | 204699119 | 10/2015 |
| CN | 105268214 | 1/2016 |
| CN | 105408671 | 3/2016 |
| CN | 105476069 | 4/2016 |
| CN | 105805395 | 7/2016 |
| CN | 107073190 | 8/2017 |

(56)                References Cited

FOREIGN PATENT DOCUMENTS

| | | | |
|---|---|---|---|
| DE | 3923692 | 1/1991 | |
| DE | 3923692 A1 * | 1/1991 | ............ A61M 1/262 |
| EP | 0129345 | 12/1984 | |
| EP | 1027898 | 8/2000 | |
| EP | 0749345 | 1/2003 | |
| EP | 1344542 A1 * | 9/2003 | ........... B01D 63/034 |
| EP | 1398047 | 3/2004 | |
| EP | 1509261 | 3/2005 | |
| EP | 1529545 | 5/2005 | |
| EP | 1529545 A2 * | 5/2005 | ............ B01D 61/30 |
| EP | 2488226 | 11/2013 | |
| EP | 2694127 | 2/2014 | |
| EP | 2697515 | 2/2014 | |
| EP | 1509260 | 4/2014 | |
| EP | 2719403 | 4/2014 | |
| EP | 2735358 | 5/2014 | |
| EP | 3018352 | 5/2016 | |
| EP | 2906265 | 7/2016 | |
| EP | 3263150 | 1/2018 | |
| EP | 3326670 | 5/2018 | |
| EP | 2600917 | 10/2018 | |
| EP | 3530301 | 8/2019 | |
| EP | 2750732 | 10/2019 | |
| EP | 2761265 | 11/2019 | |
| EP | 3578211 | 12/2019 | |
| EP | 2207966 | 2/2020 | |
| EP | 3606577 | 2/2020 | |
| EP | 3416702 | 3/2020 | |
| EP | 3362121 | 4/2020 | |
| GB | 2458572 | 9/2009 | |
| JP | 6571234 | 9/2019 | |
| WO | WO 2002/043859 | 6/2002 | |
| WO | WO 2002/090671 | 11/2002 | |
| WO | WO 2003/099355 | 12/2003 | |
| WO | WO 2006/053384 | 5/2006 | |
| WO | WO 2009/064984 | 5/2009 | |
| WO | WO 2011/017215 | 2/2011 | |
| WO | WO 2013/017181 | 2/2013 | |
| WO | WO 2015/013273 | 1/2015 | |
| WO | WO 2016/039821 | 3/2016 | |
| WO | WO 2018/187576 | 10/2018 | |
| WO | WO 2019/143623 | 7/2019 | |
| WO | WO 2019/189036 | 10/2019 | |
| WO | WO-2020174097 A1 * | 9/2020 | ......... B01D 61/0022 |

OTHER PUBLICATIONS

International Preliminary Report on Patentability in International Appln. No. PCT/US2019/042967, dated Feb. 11, 2021, 7 pages.
International Preliminary Report on Patentability in International Appln. No. PCT/US2019/043023, dated Feb. 11, 2021, 7 pages.
International Preliminary Report on Patentability in International Appln. No. PCT/US2019/044306, dated Feb. 11, 2021, 8 pages.
International Preliminary Report on Patentability in International Appln. No. PCT/US2019/057775, dated Jun. 17, 2021, 9 pages.
International Preliminary Report on Patentability in International Appln. No. PCT/US2020/044751, dated Feb. 17, 2022, 11 pages.
International Preliminary Report on Patentability in International Appln. No. PCT/US2020/058281, dated May 27, 2022, 9 pages.
International Search Report and Written Opinion in International Appln. No. PCT/US2019/042967, dated Oct. 8, 2019, 8 pages.
International Search Report and Written Opinion in International Appln. No. PCT/US2019/043023, dated Oct. 8, 2019, 12 pages.
International Search Report and Written Opinion in International Appln. No. PCT/US2019/044306, dated Oct. 24, 2019, 13 pages.
International Search Report and Written Opinion in International Appln. No. PCT/US2019/057775, dated Apr. 2, 2020, 17 pages.
International Search Report and Written Opinion in International Appln. No. PCT/US2020/044751, dated Nov. 4, 2020, 18 pages.
International Search Report and Written Opinion in International Appln. No. PCT/US2020/058281, dated Feb. 11, 2021, 14 pages.
International Search Report and Written Opinion in International Appln. No. PCT/US2020/064462, dated Mar. 23, 2021, 12 pages.
Invitation to Pay Additional Fees in International Appln. No. PCT/US2019/057775, dated Feb. 11, 2020, 11 pages.

* cited by examiner

Blood ----------
Substituate — — —
Dialysate · —— · ——

BLOOD TREATMENT SYSTEMS

CROSS-REFERENCE TO RELATED APPLICATIONS

The present application is the national stage entry of International Patent Application No. PCT/US2020/064462, filed on Dec. 11, 2020, and claims priority to U.S. Provisional Application No. 62/947,285, filed Dec. 12, 2019. The disclosures of which are expressly incorporated herein in its entirety by reference thereto.

TECHNICAL FIELD

This disclosure relates to blood treatment systems.

BACKGROUND

Dialysis is a medical treatment that provides life-saving support to patients with insufficient renal function. The two principal dialysis methods are hemodialysis (HD) and peritoneal dialysis (PD). During HD, the patient's blood is passed through a dialyzer of a dialysis machine, while a dialysis solution (or, dialysate) is also passed through the dialyzer, generally in an opposite or countercurrent direction. A semi-permeable membrane within the dialyzer separates the blood from the dialysate and allows fluid exchanges to take place between the dialysate and the blood stream via diffusion, osmosis, and convective flow. These exchanges across the membrane result in the removal of waste products (e.g., such as solutes, like urea and creatinine) from the blood. These exchanges also help regulate the levels of other substances (e.g., sodium and water) in the blood. In this way, the dialyzer and dialysis machine act as an artificial kidney for cleansing the blood.

During PD, the patient's peritoneal cavity is periodically infused with dialysate. The membranous lining of the patient's peritoneum acts as a natural semi-permeable membrane that allows diffusion and osmosis exchanges to take place between the solution within the peritoneal cavity and the blood stream. Like HD, these exchanges across the patient's peritoneum result in the removal of waste products from the blood and help regulate the levels of other substances (e.g., sodium and water) in the blood.

Automated PD machines (e.g., PD cyclers) are designed to control the entire PD process so that it can be performed at home, usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other.

SUMMARY

This disclosure relates to blood treatment systems.

In one aspect, a system includes a blood treatment machine; a dialyzer configured to be coupled to the blood treatment machine, the dialyzer including a dialyzer housing defining a blood inlet and a blood outlet; a bundle of hollow fibers within an interior of the dialyzer housing; a pumping device drivable to force blood received from the blood inlet through lumens of the bundle of hollow fibers and out the blood outlet; a dialysate inlet port in fluid communication with a dialysate flow path that includes space in the interior of the dialyzer housing between the bundle of hollow fibers; and a dialysate outlet port in fluid communication with the dialysate flow path. The system further includes a fluid conditioning system configured to (i) prepare and supply fresh dialysate to the dialyzer via the dialysate inlet port, and (ii) receive spent dialysate from the dialyzer via the dialysate outlet port, recycle the spent dialysate, and supply the recycled dialysate to the dialyzer via the dialysate inlet port.

In another aspect, a system includes a blood treatment machine including a treatment module including a structure for releasably coupling with a dialyzer, the treatment module including: (i) a first pressure transducer positioned to abut against a first membrane of a first pressure detection chamber of the dialyzer while the dialyzer is coupled with the treatment module and (ii) a second pressure transducer positioned to abut against a second membrane of a second pressure detection chamber of the dialyzer while the dialyzer is coupled with the treatment module; and a fluid conditioning system configured to (i) prepare and supply fresh dialysate to the dialyzer, and (ii) receive spent dialysate from the dialyzer, recycle the spent dialysate, and supply the recycled dialysate to the dialyzer.

Embodiments may include one or more of the following features.

In some embodiments, the fluid conditioning system is a standalone unit configured to be connected via fluid lines to the blood treatment machine.

In some embodiments, the fluid conditioning system is a standalone unit configured to be connected via fluid lines directly to the dialyzer.

In some embodiments, the fluid conditioning system is part of the blood treatment machine.

In some embodiments, the fluid conditioning system includes a dialysis fluid cassette including an inlet fluid line; a plurality of outlet fluid lines; and a valve comprising an actuation feature by which the valve can be rotated to fluidly communicate the inlet fluid line with a selected fluid line of the plurality of outlet fluid lines.

In some embodiments, the actuation feature of the dialysis fluid cassette comprises a surface profile that is formed to be engaged by an actuator for rotating the valve. In some embodiments, the actuation feature of the dialysis fluid cassette has a polygonal shape. In some embodiments, the valve of the dialysis fluid cassette further includes a valve body defining an internal fluid pathway that can fluidly communicate the inlet fluid line with the selected fluid line; and a spring that is configured to move the valve body to enable or disable an operation of the valve.

In some embodiments, the valve body of the dialysis fluid cassette is movable to: a first position at which the internal fluid pathway is aligned with the inlet fluid line and the plurality of outlet fluid lines to enable the operation of the valve, and a second position at which the internal fluid pathway is offset from the inlet fluid line and the plurality of outlet fluid lines to disable the operation of the valve.

In some embodiments, the dialysis fluid cassette further includes a plurality of inlet fluid lines that includes the inlet fluid line, wherein the valve comprises a valve body defining an internal fluid conduit that can fluidly communicate the inlet fluid line of the plurality of inlet fluid lines with the selected fluid line of the plurality of outlet fluid lines to define a fluid pathway of a plurality of fluid pathways within the dialysis fluid cassette.

In some embodiments, the internal fluid conduit is a first internal fluid conduit, the inlet fluid line is a first selected inlet fluid line, the selected fluid line is a first selected outlet fluid line, and the fluid pathway is a first fluid pathway, the valve body further defining a second internal fluid conduit that can fluidly communicate a second selected inlet fluid line of the plurality of inlet fluid lines with a second selected outlet fluid line of the plurality of outlet fluid lines to define a second fluid pathway of the plurality of fluid pathways within the dialysis fluid cassette.

In some embodiments, the dialyzer further includes a first end cap that defines the blood inlet and a second end cap that defines the blood outlet.

In some embodiments, the dialyzer further includes a venous pressure detection chamber arranged between the bundle of hollow fibers and the blood outlet, the venous pressure detection chamber comprising a first flexible surface attached to the second end cap.

In some embodiments, the dialyzer further includes an arterial pressure detection chamber arranged between the blood inlet and the bundle of hollow fibers, the arterial pressure detection chamber having a second flexible surface attached to the first end cap.

In some embodiments, the first end cap defines the dialysate outlet port and the second end cap defines the dialysate inlet port.

In some embodiments, the first end cap defines a substituate liquid inlet port in fluid communication with the lumens of the bundle of hollow fibers.

In some embodiments, the second end cap defines a substituate liquid outlet port in fluid communication with the lumens of the bundle of hollow fibers.

In some embodiments, the pumping device includes a pump rotor within the first end cap. In some embodiments, the dialyzer further includes one or more magnets encased within the pump rotor, the pump rotor being magnetically-drivable to force blood through the lumens of the hollow fibers. In some embodiments, the dialyzer further includes one or more magnets attached to the pump rotor, the pump rotor being magnetically-drivable to force blood through the lumens of the hollow fibers. In some embodiments, the pump rotor is magnetically levitated during operation.

In some embodiments, the dialyzer housing includes a deaeration chamber. In some embodiments, the deaeration chamber is defined in an end cap of the dialyzer housing.

In some embodiments, the pumping device is contained at a fixed location relative to the hollow fibers.

In some embodiments, the fluid conditioning system is located inside a housing of the blood treatment machine.

In some embodiments, the first and second pressure transducers are positioned to abut opposite ends of the dialyzer while the dialyzer is coupled with the treatment module.

In some embodiments, the first and second pressure transducers are reconfigurable between: (i) a first position in which the first and second pressure transducers are retracted and (ii) a second position in which the first and second pressure transducers are extended to abut against the first and second membranes respectively.

In some embodiments, the treatment module further includes a first pair of conduits configured to connect with a first substitute liquid port and a first dialysate port defined by the dialyzer while the dialyzer is coupled with the treatment module; and a second pair of conduits configured to connect with a second substitute liquid port and a second dialysate port defined by the dialyzer while the dialyzer is coupled with the treatment module, wherein the first and second pair of conduits are fluidly connected with the fluid conditioning system.

Embodiments may provide one or more of the following advantages.

As discussed above, the system can include a fluid conditioning system capable of recycling dialysate. This means less water is used, less waste is generated, and less dialysis fluid concentrate is required as compared to most conventional dialysis machines. This is beneficial for home hemodialysis since less storage space is required.

Another advantage is the incorporation of various components into dialyzer can make it easier to set up the machine because the dialyzer and its various components can be connected to the machine in fewer steps that would be required to connect more complicated blood line sets. In some embodiments, for example, the dialyzer and its components can be connected to the machine in a single action. This is again beneficial for home hemodialysis since the user may not be a trained clinician.

Additionally, the incorporation of certain components, such as a pump, pressure sensors, an air release chamber, etc., into the dialyzer which allows for a simpler and shorter blood line set to be used, and provides an overall a more compact hemodialysis machine.

Other aspects, features, and advantages will be apparent from the description, the drawings, and the claims.

DETAILED DESCRIPTION

Figure 19:
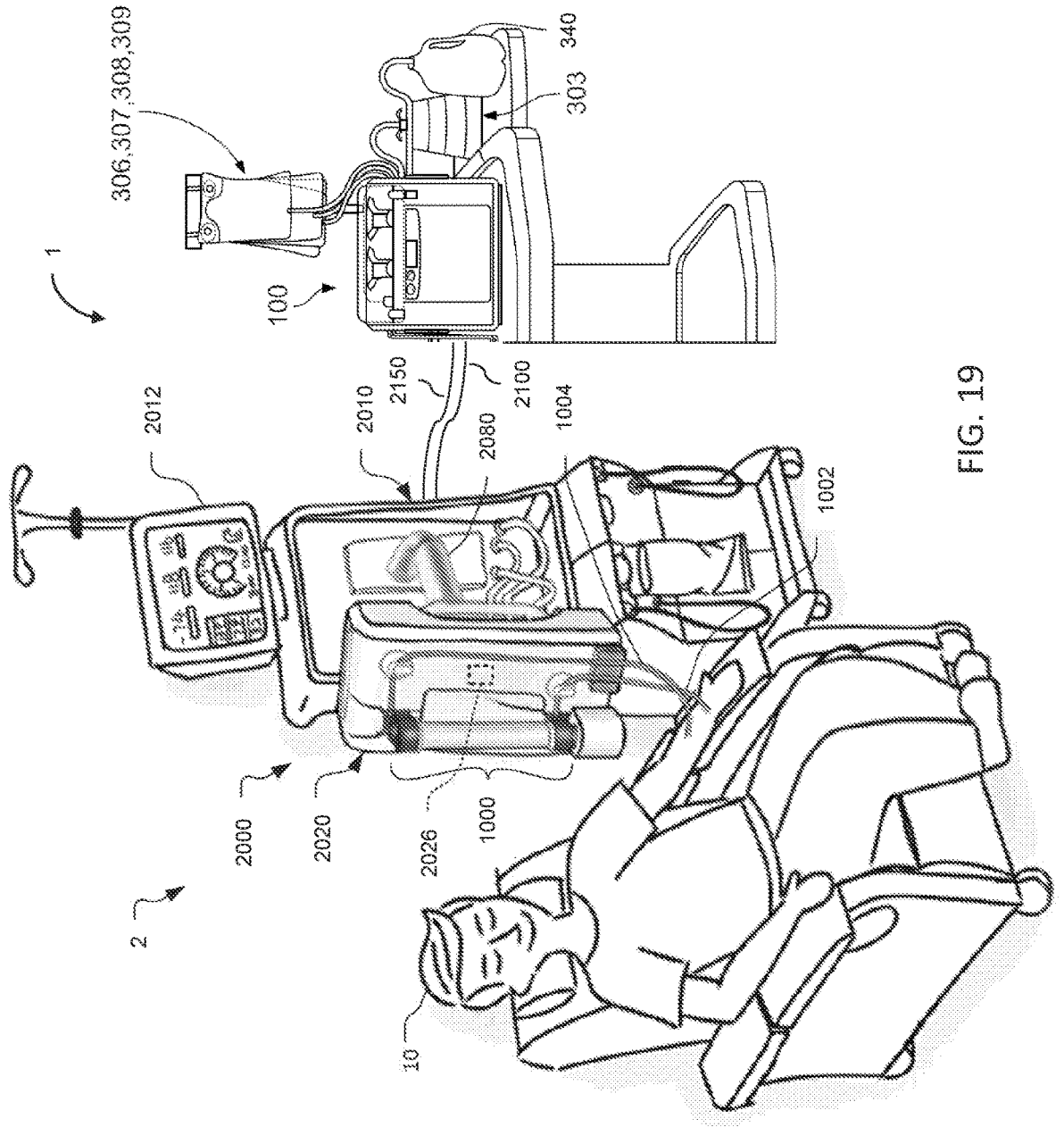
FIG. 19 depicts a patient receiving an extracorporeal blood treatment using a hemodialysis system connected to the fluid conditioning system of FIG. 1.

FIG. 19 shows a system 1 including a hemodialysis system 2 connected to a fluid conditioning system 100 via fluid lines 324 and 325. During a hemodialysis treatment, the fluid conditioning system 100 delivers fresh dialysate to a hemodialysis machine 2000 of the hemodialysis system 2, and the hemodialysis machine 2000 pumps the fresh dialysate through a dialysate chamber of a dialyzer 1000 via a fresh dialysate line. While the fresh dialysate is being pumped through the dialysate chamber of the dialyzer 1000, the hemodialysis machine 2000 withdraws blood from a patient 10 via an arterial line 1002, passes the blood through a blood chamber of the dialyzer 1000, and then returns the filtered blood to the patient 10 via a venous line 1004. As the blood passes through the dialyzer 1000, the blood is separated from the flowing fresh dialysate by semi-permeable membranes (e.g., hollow fibers). Due to the composition of the dialysate and/or a pressure differential across the semi-permeable membranes, waste and toxins from the blood flow across the membranes and are carried by the dialysate (now referred to as used or spent dialysate) out of the dialyzer 1000. The spent dialysate flows back to the hemodialysis machine 2000 via a spent dialysate line and is then pumped from the hemodialysis machine 2000 to the fluid conditioning system 100 where it is recycled to become fresh dialysate. That fresh dialysate is then returned to the hemodialysis machine 2000 to be passed through the dialyzer 1000 for further treatment of the patient's blood.

As shown in FIG. 19, the hemodialysis system 2 includes a disposable set connected to the hemodialysis machine 2000. The disposable set includes the dialyzer 1000 that is configured to be coupled to a treatment module 2020 of the hemodialysis machine 2000, as well as the arterial and venous lines 1002, 1004 that are connected to the dialyzer 1000 and are configured to be placed in fluid communication with the patient 10 during the treatment. The dialyzer 1000 is a single-use disposable item, whereas the hemodialysis machine 2000 is a reusable system.

As will be explained in greater detail below, the dialyzer 1000 includes certain components, such as a blood pump, a pressure sensor chamber, and an air release chamber, that are typically found in blood line sets that are used with dialyzers. Incorporating such features into the dialyzer 1000 can make it easier for a user to set up the hemodialysis system 2 because the user can simply plug the dialyzer 1000 into the hemodialysis machine 2000 rather than having to connect various separate components arranged along the arterial and venous lines 1002, 1004 to the hemodialysis machine 2000. As a result, the hemodialysis system 2 can be particularly advantageous for home dialysis patients who often times set up the system themselves or have a care taker who is not a trained clinician set up the system for them.

As explained above, the fluid conditioning system 100 is fluidly connected to the hemodialysis machine 2000 of the hemodialysis system 2 to deliver "fresh" (e.g., cleaned, conditioned) dialysate to the hemodialysis system 2, collect "spent" (e.g., contaminated, unconditioned) dialysate from the hemodialysis system 2, and recycle the spent dialysate. The fluid conditioning system 100 may also be used to generate fresh dialysate prior to treatment. Generating and reusing dialysate in this way can significantly reduce the amount of pre-packaged dialysate and/or dialysate concentrates that are required to carry out a dialysis treatment. This can be particularly beneficial to home dialysis patients because it allows them to carry out treatments without have to receive and store large volumes of fluids in their homes. The fluid conditioning system 100 will now be described in greater detail. As shown in FIGS. 1-4, the fluid conditioning system 100 includes a housing 101 that contains or supports components of the fluid conditioning system 100, a fluid cassette 102 that includes multiple fluid lines defining various fluid pathways, two relatively high capacity pumps 103 that can circulate fluid within the fluid lines of the fluid cassette 102, and two relatively low capacity pumps 104 that can deliver (e.g., infuse) conditioning agents into the fluid circulating within the fluid lines of the fluid cassette 102. The fluid conditioning system 100 has a compact footprint that facilitates lifting and transport of the fluid conditioning system 100. For example, the fluid conditioning system 100 typically has a length of about 30 cm to about 50 cm, a width of about 30 cm to about 50 cm, a height of about 30 cm to about 50 cm, and a weight of about 15 kg to about 20 kg.

The housing 101 includes left and right side panels 105, 106, handles 107 positioned along the side panels 105, 106 for carrying the fluid conditioning system 100, a door assembly 108 that can be opened and closed to insert a heater bag, a front panel 109 to which the door assembly 108 is secured, rear and bottom panels 110, 111 that further enclose the interior components, an upper panel 112 that supports the fluid cassette 102 and the pumps 103, 104, and a cover 113 that protects the fluid cassette 102 and the pumps 103, 104. Example materials from which the exterior panels of the housing 101 may be made include plastics, such as acrylonitrile butadiene styrene (ABS) and polycarbonate blends, among others.

The cover 113 is typically made of ABS or polycarbonate and is transparent or translucent to allow visualization of the fluid cassette 102 and the pumps 103, 104. The cover 113 can be pivoted at a rear hinge 114 disposed along the upper panel 112 to open or close the cover 113. The upper panel 112 carries two latches 115 that can be closed upon a front edge 116 of the cover 113 to secure the cover 113 in a closed position. The latches 115 can also be pulled up and apart from the cover 113 to release the cover 113 from the closed position for accessing the fluid cassette 102 and the pumps 103, 104.

Figure 1:
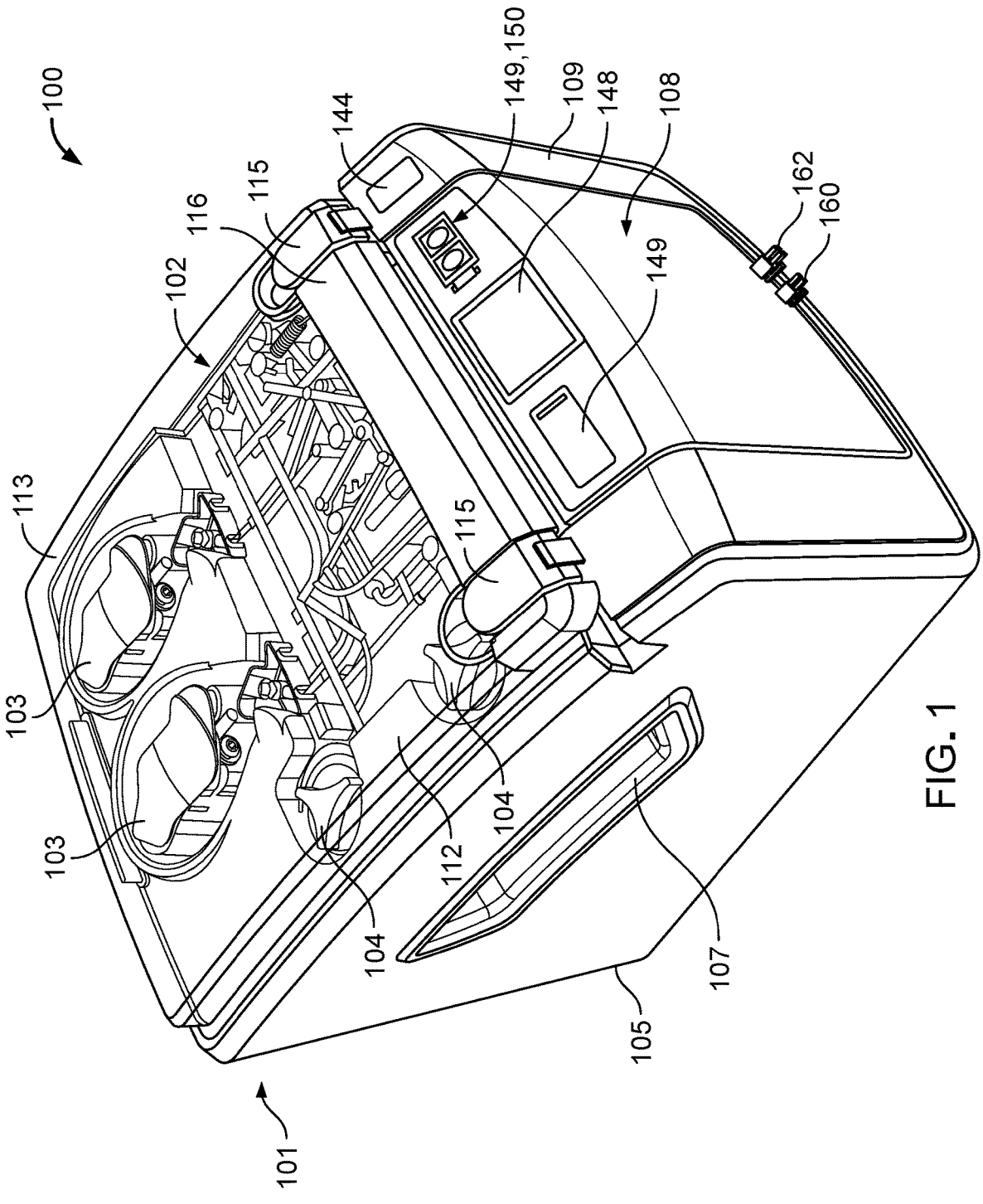
FIG. 1 is a perspective view of a fluid conditioning system that can cooperate with a dialysis system to carry out a fluid conditioning cycle during a dialysis treatment.
Figure 2:
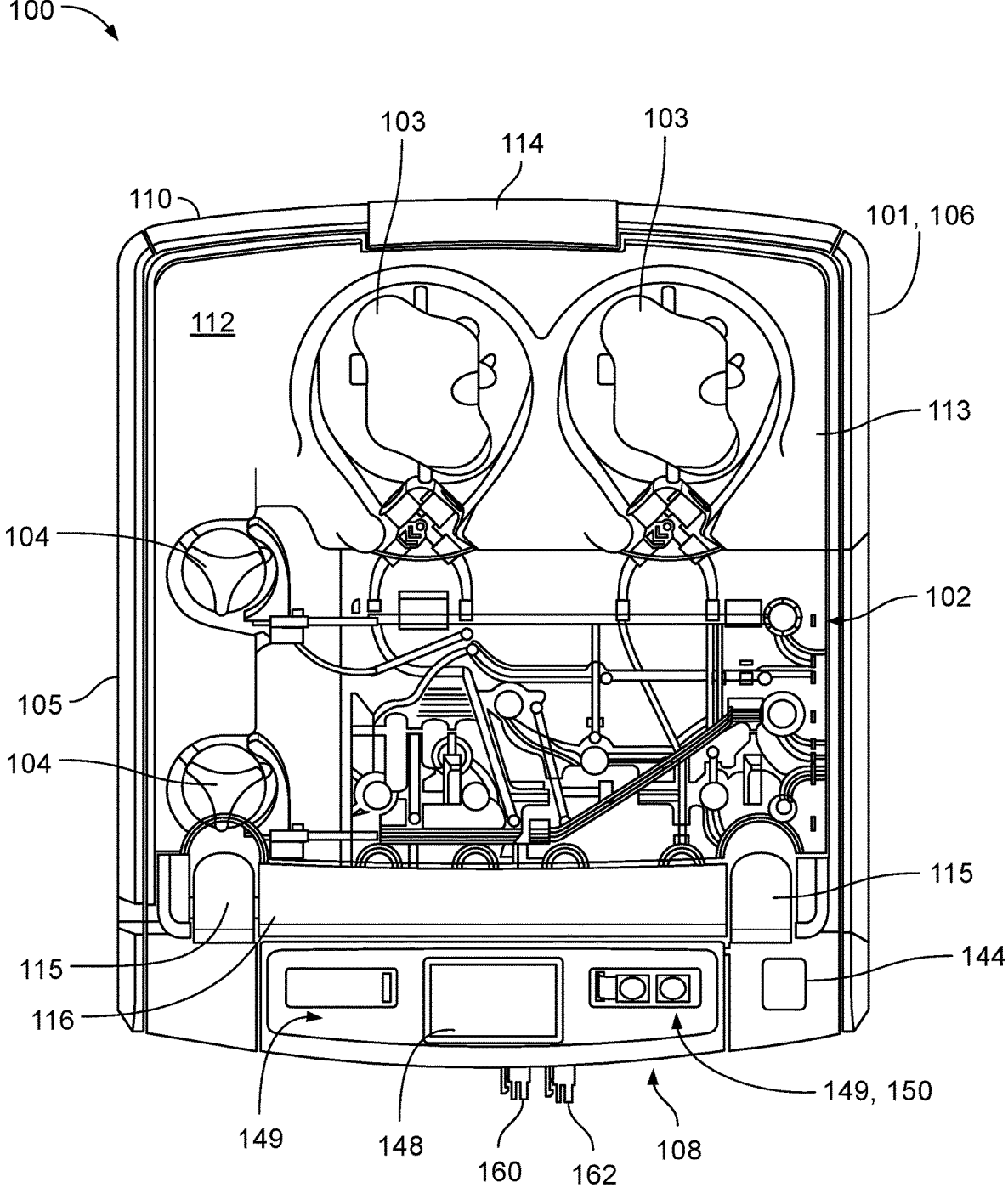
FIG. 2 is a top view of the fluid conditioning system of FIG. 1.
Figure 3:
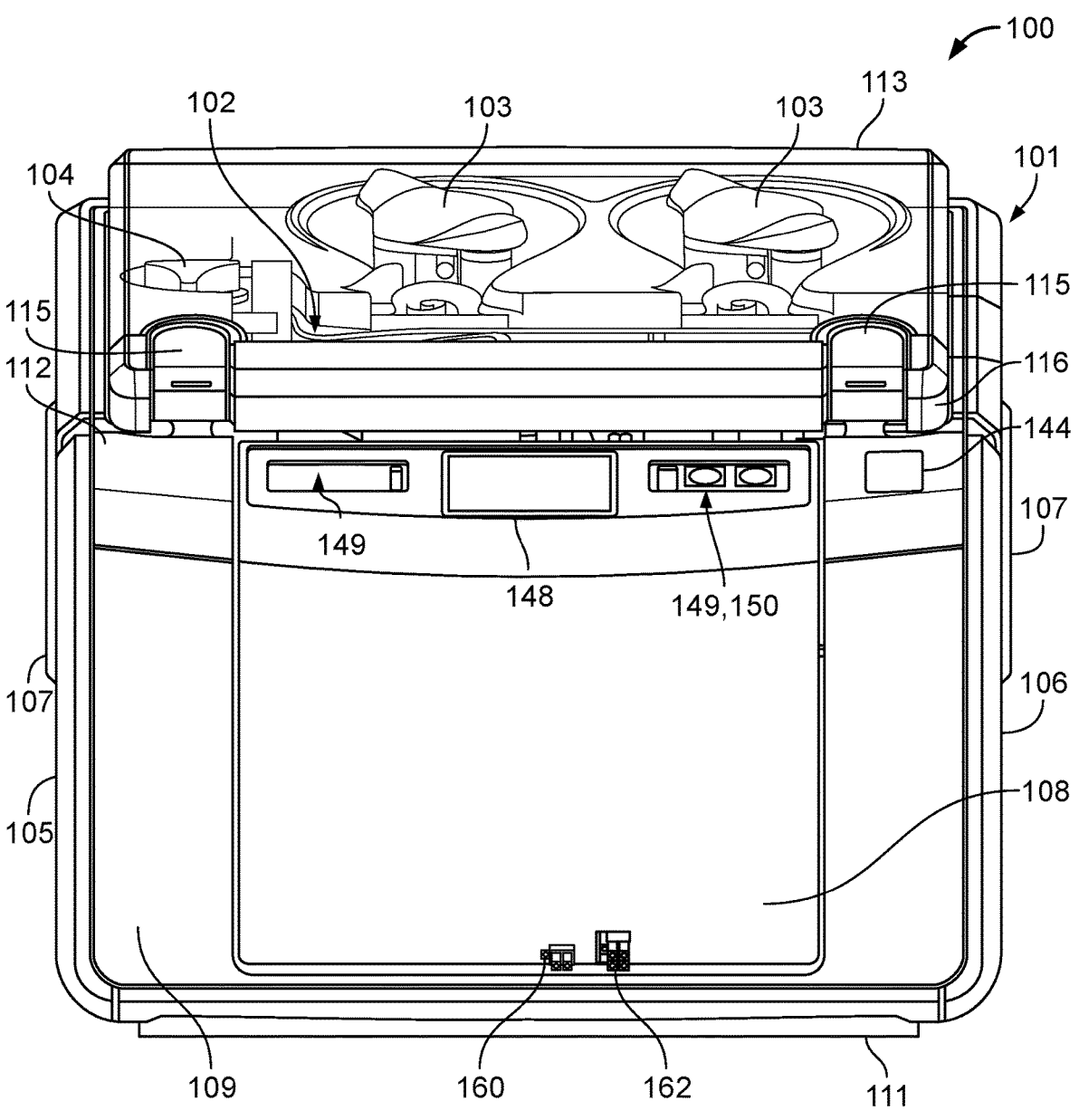
FIG. 3 is a front view of the fluid conditioning system of FIG. 1.
Figure 4:
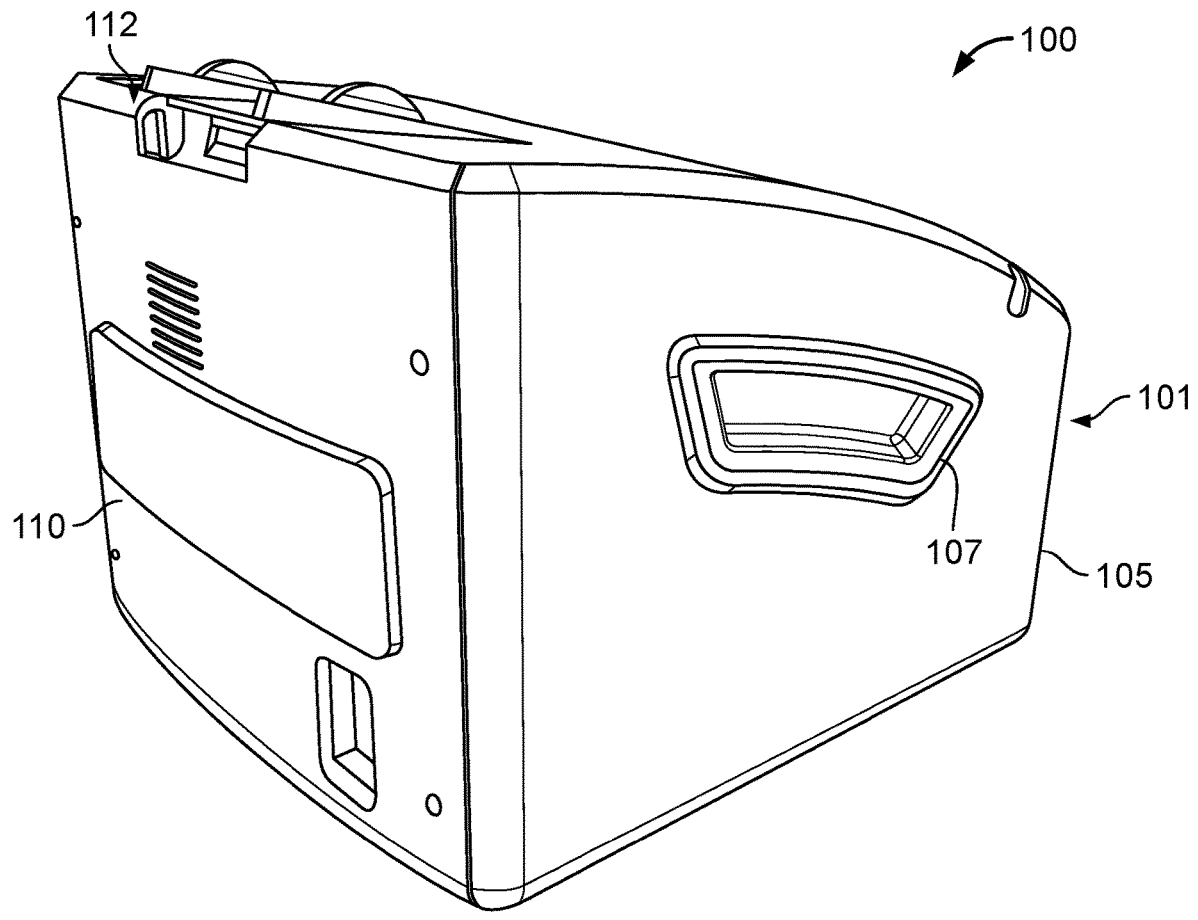
FIG. 4 is a rear view of the fluid conditioning system of FIG. 1.
Figure 5:
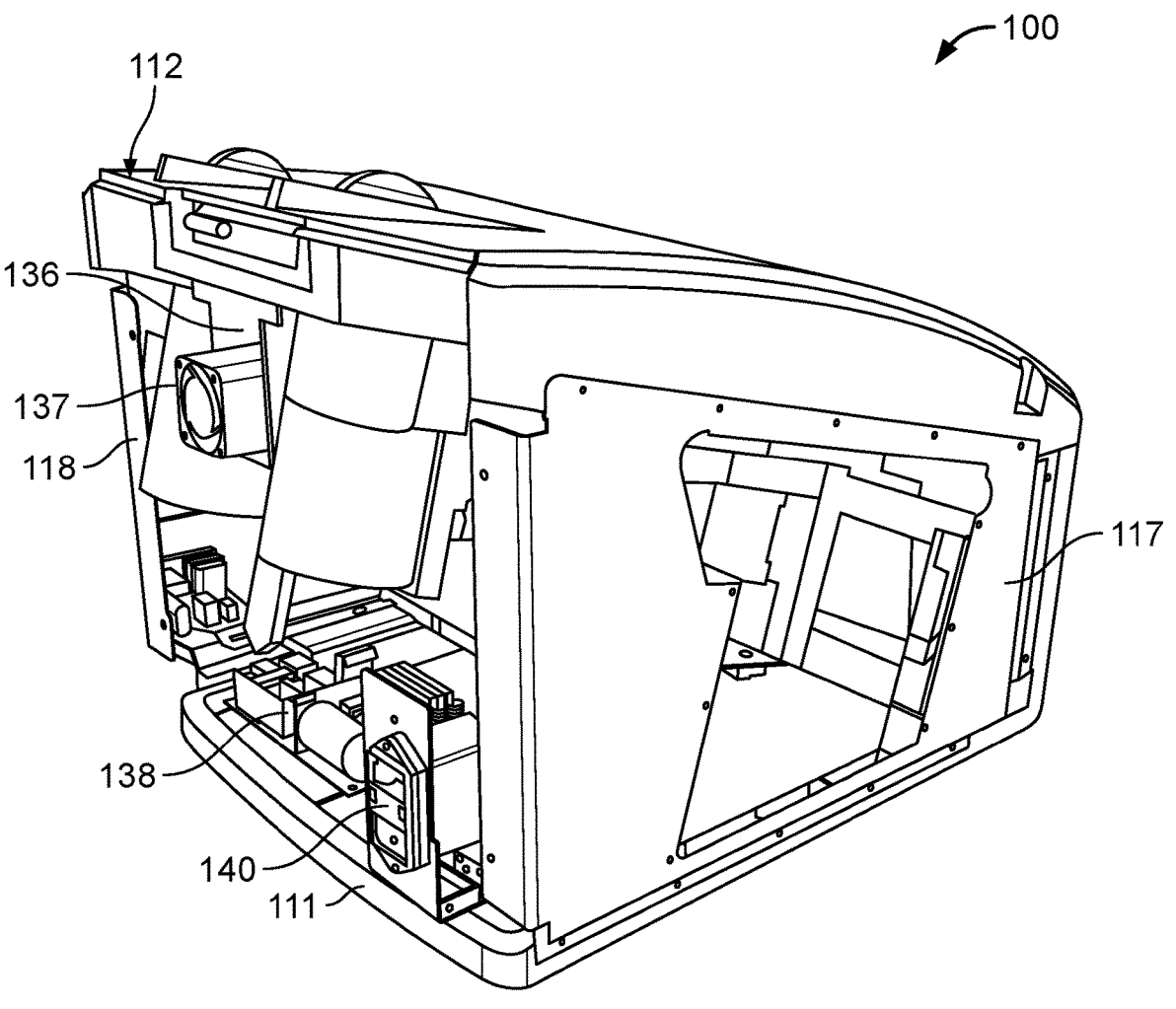
FIG. 5 is a rear view of the fluid conditioning system of FIG. 1, with certain exterior components omitted to expose certain interior components.

Referring to FIG. 5, the fluid conditioning system 100 also includes left and right side interior support frames 117, 118 to which the left side, right side, front, rear, bottom, and upper panels 105, 106, 109, 110, 111, 112 are attached. The interior support frames 117, 118 are typically formed from sheet metal.

Each pump 103, 104 is a peristaltic pump that includes multiple rollers positioned about the circumference of a rotatable frame (e.g., a motor) that carries a fluid line extending from the fluid cassette 102. As the rotatable frame is rotated, the rolling members apply pressure to the fluid line, thereby forcing fluid to flow through the fluid line.

Figure 6:
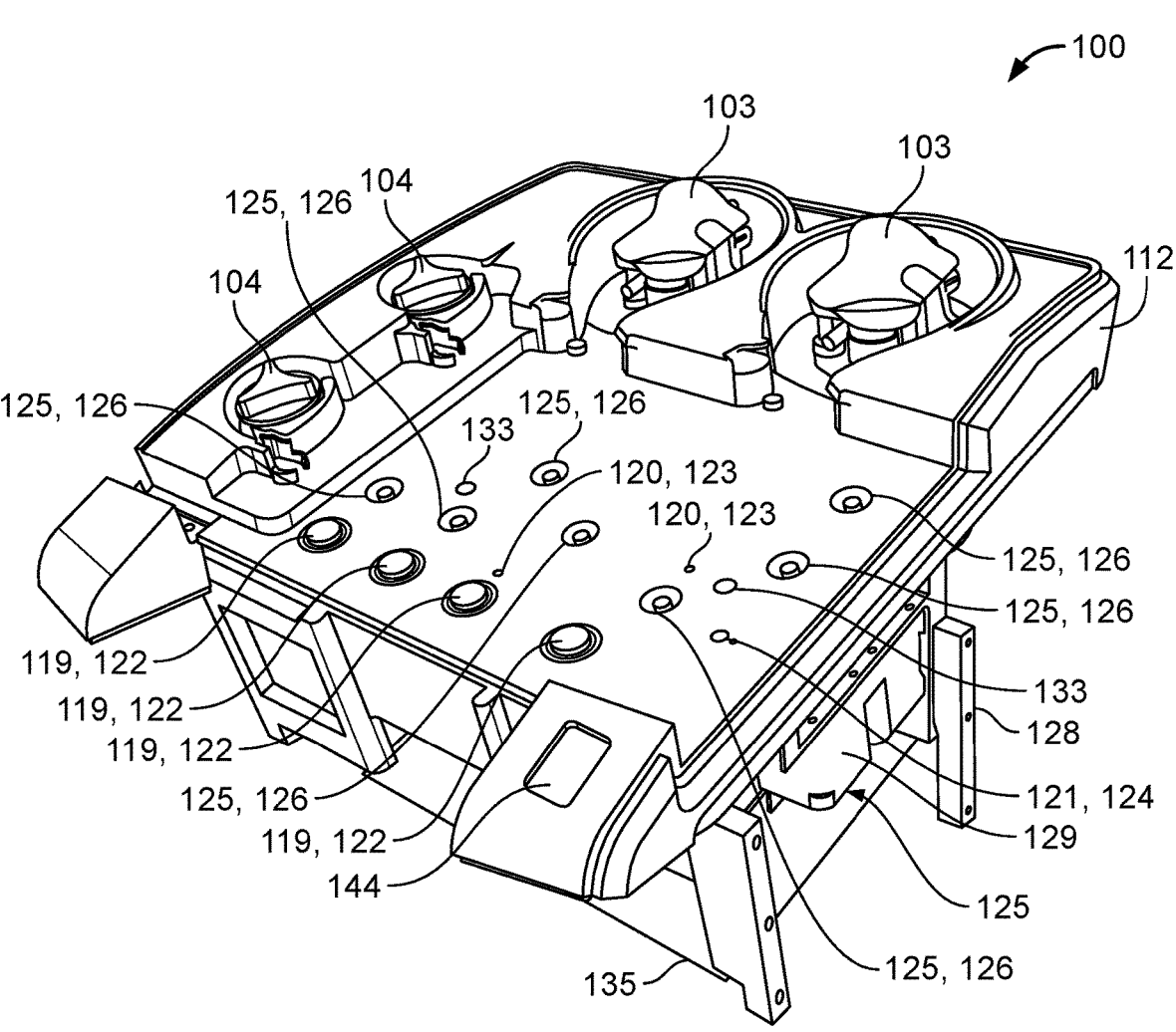
FIG. 6 is a perspective view of the fluid conditioning system of FIG. 1, with certain exterior components omitted to expose certain interior components.
Figure 7:
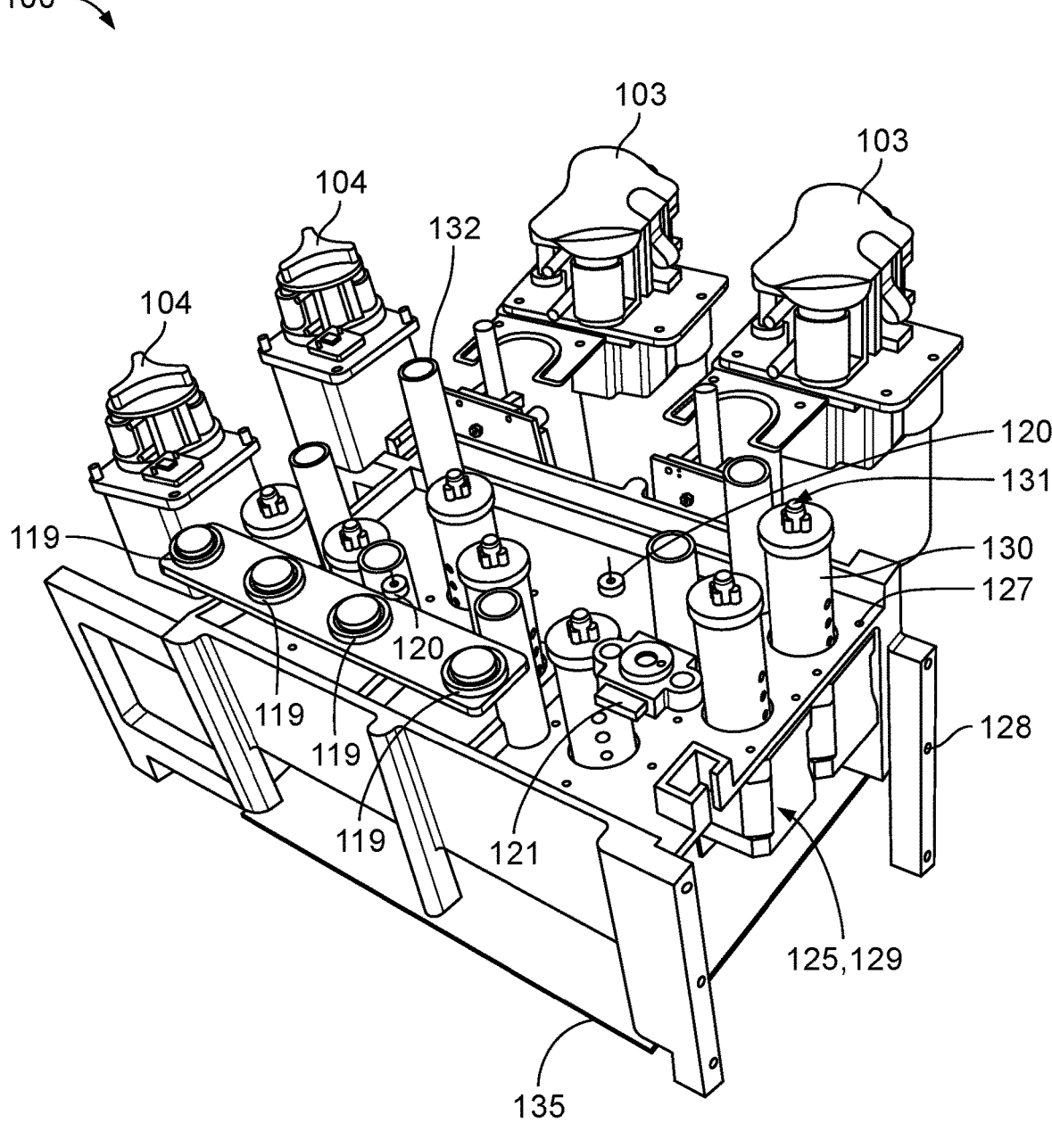
FIG. 7 is a perspective view of the fluid conditioning system of FIG. 1, with certain exterior components omitted to expose certain interior components.
Figure 8:
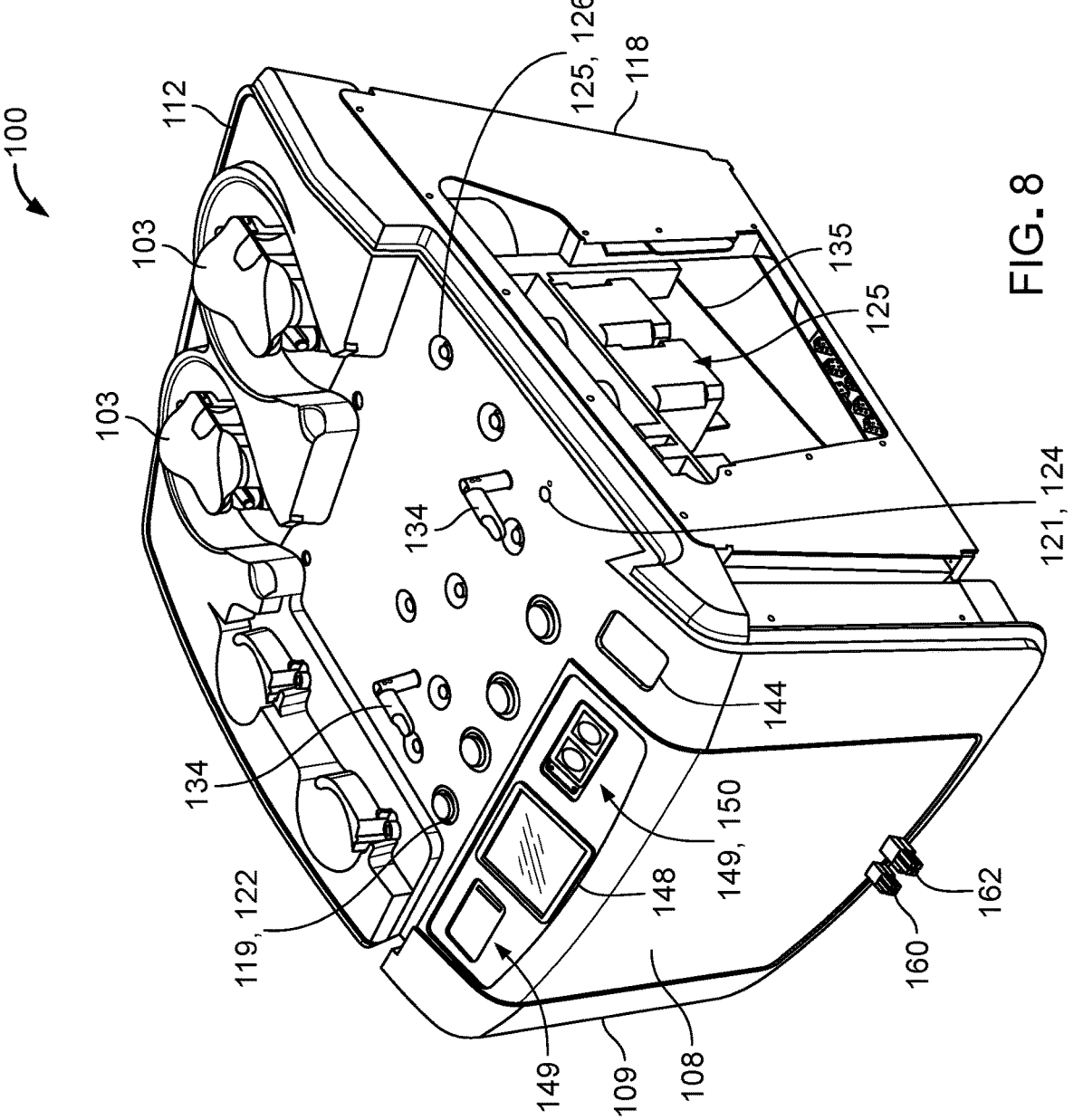
FIG. 8 is a perspective view of the fluid conditioning system of FIG. 1, with certain exterior components omitted to expose certain interior components.

FIGS. 6-8 illustrate certain interior components of the fluid conditioning system 100. For example, the fluid conditioning system 100 further includes multiple pressure transducers 119, two temperature sensors 120, and an ammonia detector 121 that are respectively positioned within holes 122, 123, 124 in the upper panel 112 for engagement with the fluid cassette 102. The pressure transducers 119 are embodied as thin, flexible membranes that contact corresponding thin, flexible membranes 164 within the fluid cassette 102 (refer to FIG. 15) for detecting fluid pressures within certain fluid pathways of the fluid cassette 102. The temperature sensors 120 are infrared (IR) sensors that detect temperatures of the dialysate flowing through certain points of the fluid pathways of the fluid cassette 102. The ammonia detector 121 is a red-green-blue (RGB) color sensor that can detect color changes on a paper strip within the fluid cassette 102 for determining a concentration of ammonium (e.g., which generates ammonia) within the dialysate flowing through a certain fluid pathway of the fluid cassette 102. The fluid conditioning system 100 also includes circuitry that acquires and conditions signals generated by conductivity sensors that are provided on the fluid cassette 102, which will be discussed in more detail below.

The fluid conditioning system 100 also includes multiple actuators 125 that are aligned with holes 126 in the upper panel 112 for respectively and selectively moving multiple valves of the fluid cassette 102. Each actuator 125 is mounted to a platform 127 of an internal frame 128 of the fluid conditioning system 100 and includes a motor 129 and a drive unit 130 that can be moved (e.g., rotated or otherwise manipulated) by the motor 129. The drive unit 130 is equipped with a coupling member 131 that is formed to engage a respective valve of the fluid cassette 102 such that movement of the drive unit 130 produces movement of the valve. The internal frame 128 also includes columnar support members 132 that support and locate the upper panel 112 of the housing 101. The upper panel 112 further defines holes 133 that are positioned and sized to receive locating pins 134 for appropriately positioning the fluid cassette 102 with respect to the upper panel 112. With the fluid cassette 102 in place, the locating pins 134 can be snapped down toward the upper panel 112 to lock the position of the fluid cassette 102. The fluid conditioning system 100 also includes a circuit board 135 equipped with electronics for operating the various electromechanical components of the fluid conditioning system 100. For example, the electronics execute codes for carrying out the various stages of a fluid conditioning cycle (as discussed below with reference to FIGS. 18-20), operating the pumps 103, 104, turning valves for the fluid cassette 102, processing sensor signals, operating the actuators 125, operating a heater assembly 151, and running control loops (e.g., control loops for regulating dialysate temperature, regulating pump speeds to achieve desired flow rates, regulating pump speeds to achieve desired dialysate chemical compositions, and ensuring device safety).

Referring again to FIG. 5, the fluid conditioning system 100 further includes a support bracket 136 and a fan 137 carried therein for cooling the circuit board 135 and other internal components of the fluid conditioning system 100. The fluid conditioning system 100 also includes a power supply 138, as well as a support bracket 139 that carries an A/C-in port 140.

Figure 10:
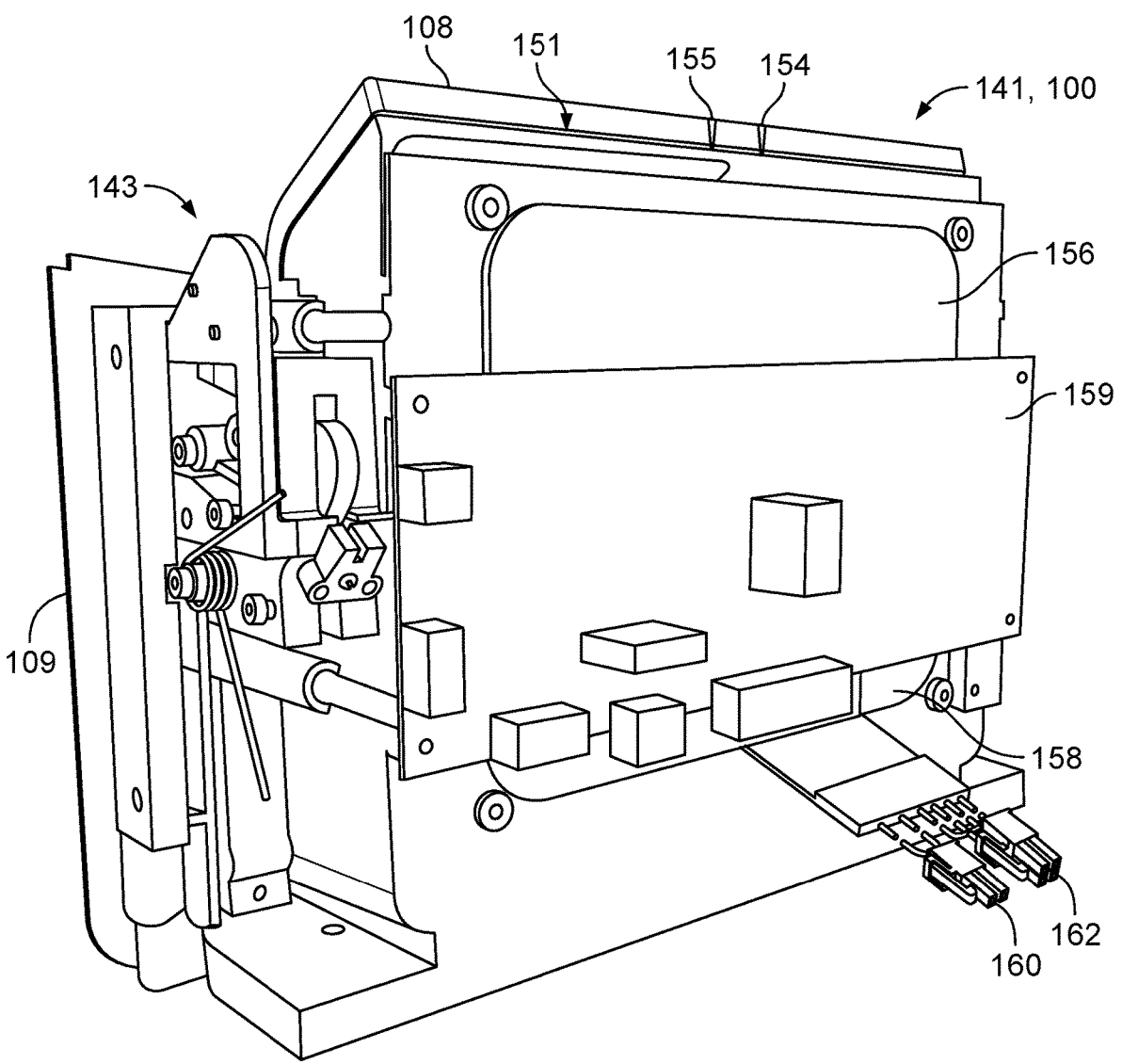
FIG. 10 is a rear perspective view of the front assembly of FIG. 9.
Figure 11:
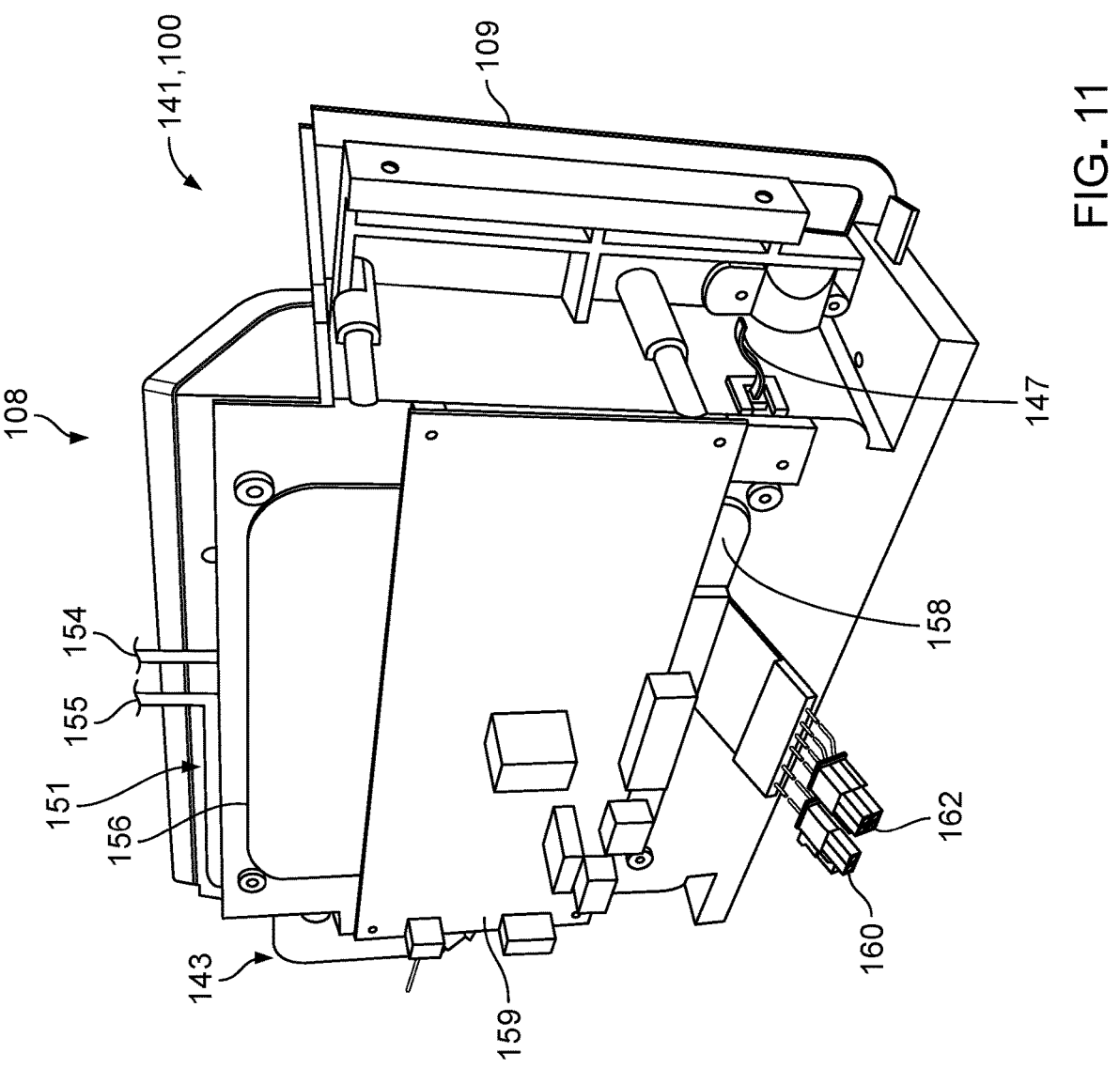
FIG. 11 is a rear perspective view of the front assembly of FIG. 9.
Figure 12:
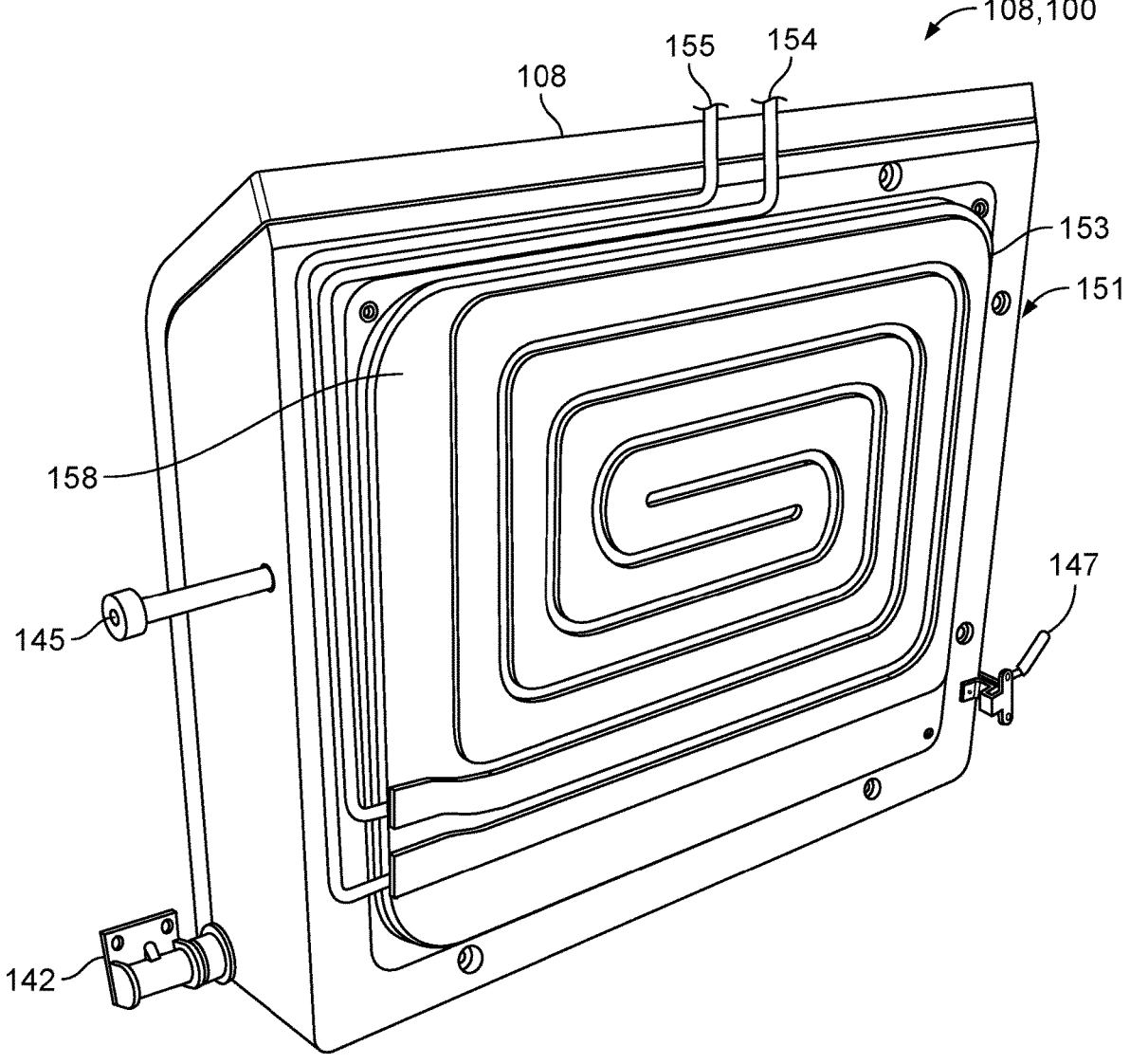
FIG. 12 is a rear perspective view of a heater bag of a door assembly of the front assembly of FIG. 9.

FIGS. 9-13 illustrate various views of a front assembly 141 of the fluid conditioning system 100. The front assembly 141 includes the door assembly 108 and the front panel 109 of the housing 101. The door assembly 108 is pivotable at hinges 142 with respect to the front panel 109 to allow loading of the heater bag 153 into the fluid conditioning system 100. The hinges 142 are friction hinges located along opposite sides of the door assembly 108, as shown in FIG. 12.

Figure 13:
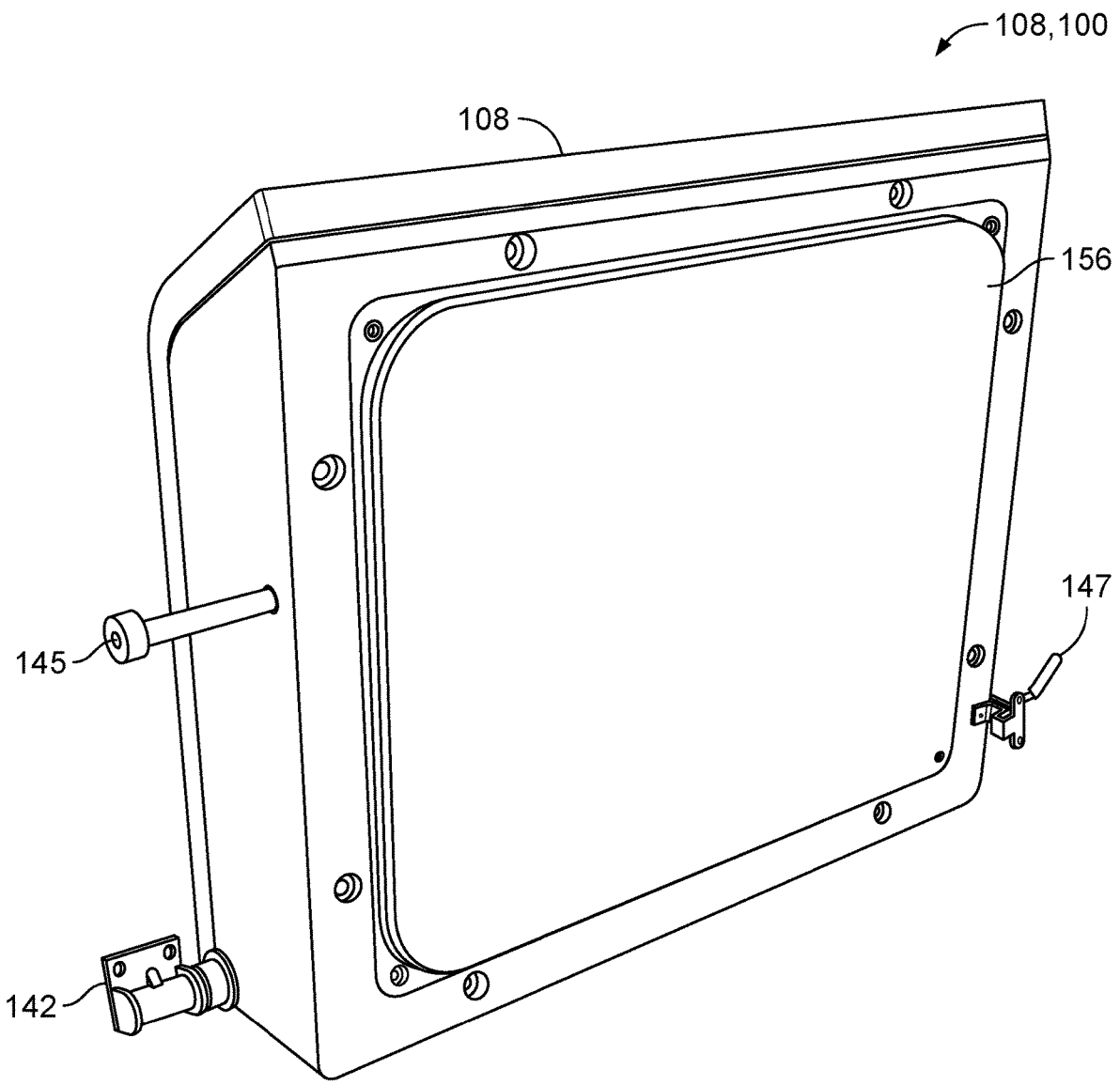
FIG. 13 is a rear perspective view of a heater plate of a door assembly of the front assembly of FIG. 9.

The front panel 109 carries a latch assembly 143 that cooperates with a button 144 carried by the upper panel 112 (shown in FIGS. 1-4) to releasably secure the door assembly 108 to the front panel 109 in a closed position. For example, depression of the button 144 adjusts the latch assembly 143 so that the door assembly 108 can be unlocked from a closed position and pivoted to an open position. The door assembly 108 can alternatively be pivoted inward from an open configuration until oppositely positioned screws 145 (e.g., shoulder screws, shown in FIG. 12) engage the latch assembly 143 to lock the door assembly 108 in the closed position. The latch assembly 143 has a contact switch for determining whether the door assembly 108 is open or closed. Referring particularly to FIGS. 11 and 13, the door assembly 108 includes an optical switch 147 that indicates whether or not the heater bag is inserted. In some embodiments, the fluid conditioning system 100 may be inoperable when the door assembly 108 is open.

Figure 9:
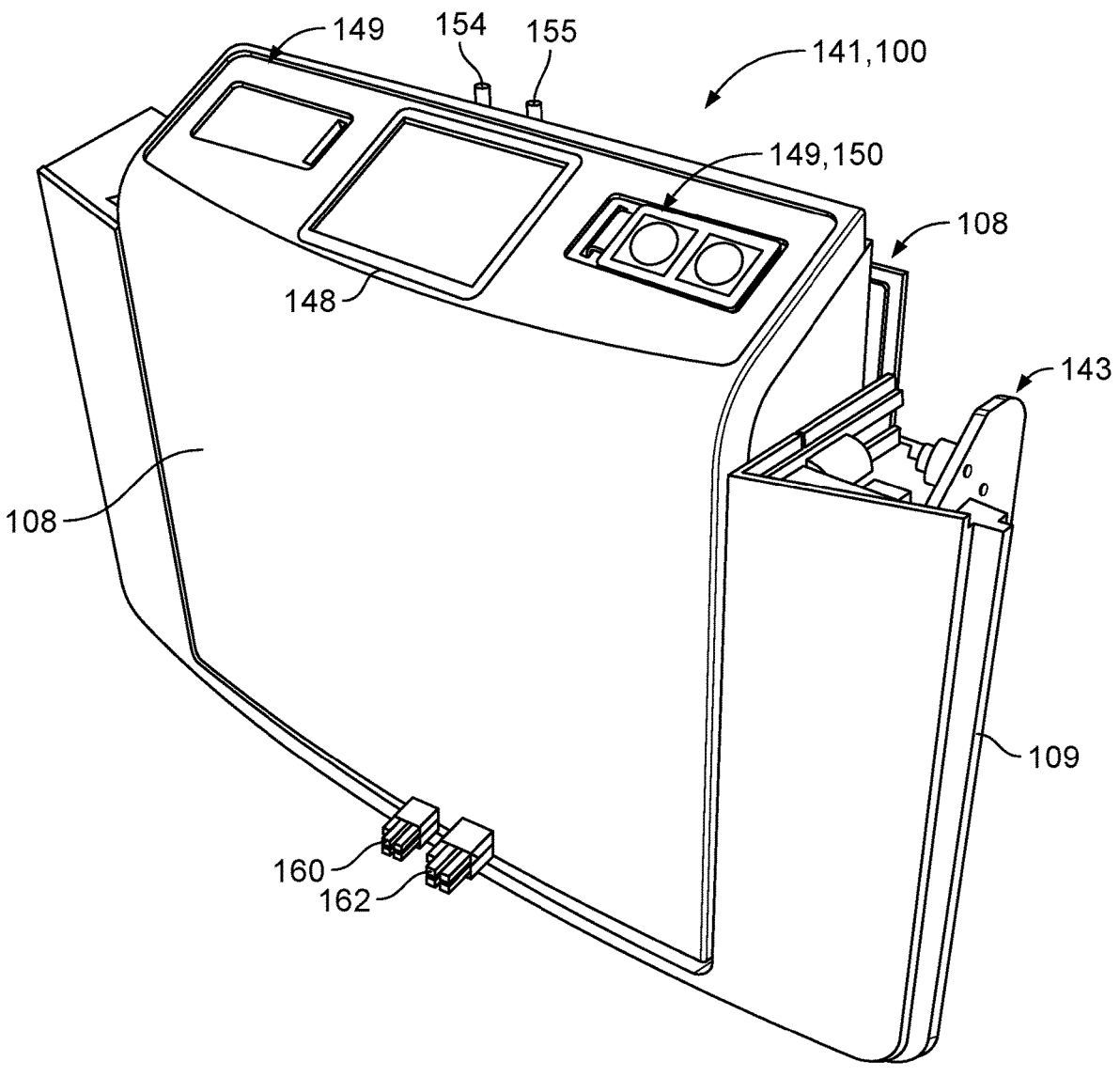
FIG. 9 is a perspective view of a front assembly of the fluid conditioning system of FIG. 1.

Referring particularly to FIG. 9, the door assembly 108 supports a display screen 148 (e.g., a touchscreen display) on which graphical user interfaces (GUIs) can be displayed and two control panels 149 that can each be equipped with selectors 150 (e.g., buttons) for providing inputs at the GUIs to operate the fluid conditioning system 100. Example parameters and processes that may be controlled by a user via the display screen 148 using the selectors 150 include starting and stopping a treatment, initiating a drain cycle, changing a flowrate, initiating a priming stage of a fluid conditioning cycle, initiating system preparation to start a fluid conditioning cycle, adjusting a temperature according to patient comfort, confirming correct placement of the fluid cassette 102, or confirming correct placement of fluid lines that interface with the pumps 103, 104.

Referring to FIGS. 10-13, the front assembly 141 includes components of a heater assembly 151 that is designed to regulate fluid temperatures of dialysate transported along the fluid pathways of the fluid cassette 102. Referring particularly to FIG. 12, the heater assembly 151 includes a heater bag 153 that is equipped with an input connection 154 and an output connection 155 that can interface with the fluid cassette 102 for allowing dialysate to circulate through the heater bag 153 to be warmed. The heater bag 153 is formed as a plastic channel that has a generally flat, collapsed shape when empty, that inflates upon filling with fluid, and that transfers heat from an exterior surface to dialysate flowing through the heater bag 153.

Figure 14:
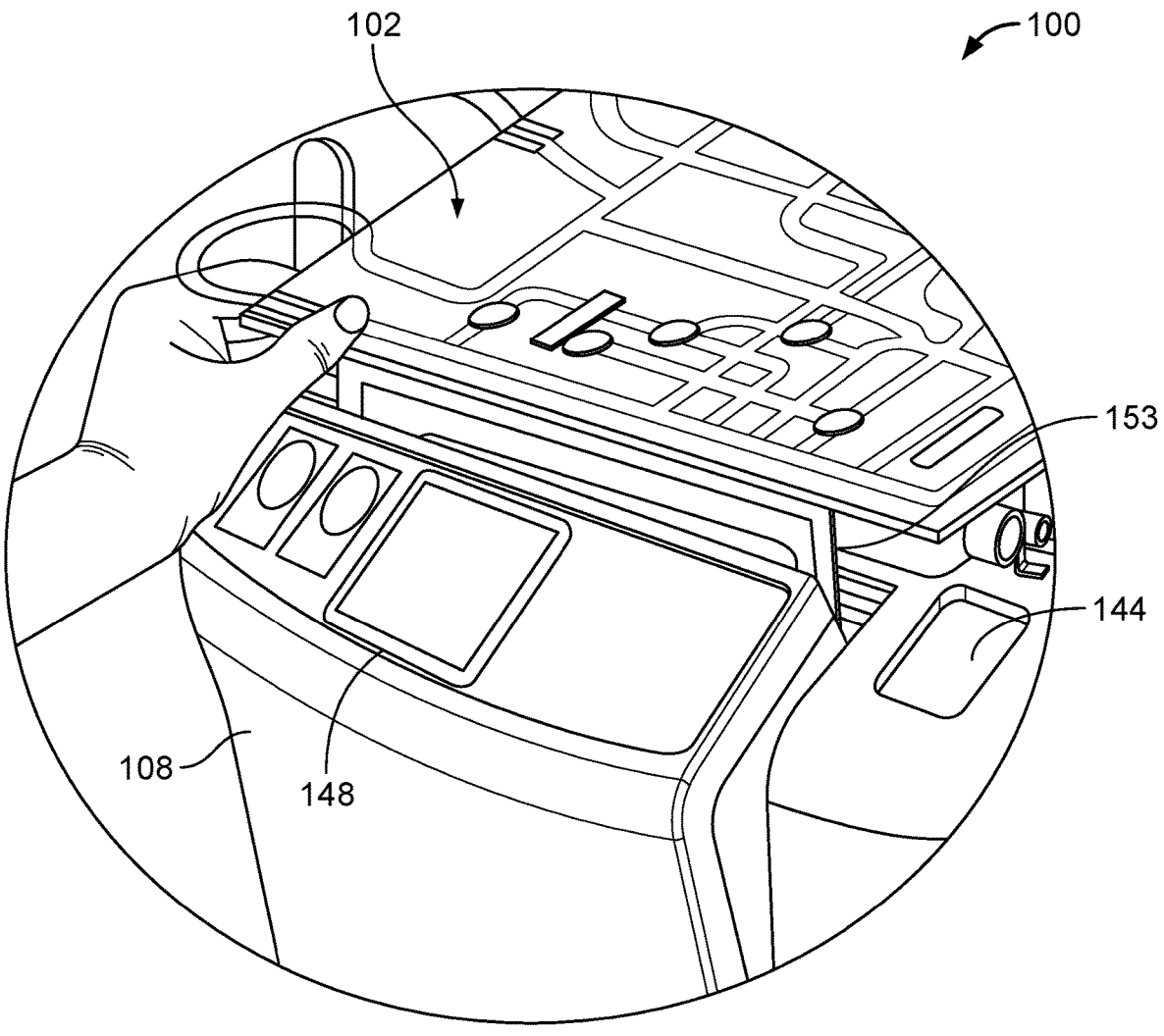
FIG. 14 is a perspective view illustrating installation of the heater bag of FIG. 12 and a fluid cassette of the fluid conditioning system of FIG. 1.

Referring particularly to FIG. 13, the heater assembly 151 further includes two plates 156 (e.g., aluminum plates) that position and support the heater bag 153 and that are heated for transferring heat to fluid within the heater bag 153. Referring particularly to FIG. 14, the heater bag 153 can be slid between the two heater plates 156 (not visible in FIG. 14) within the door assembly 108 when the door assembly 108 is in the open configuration. Referring particularly to FIGS. 10-12, the heater assembly 151 further includes one or more heating elements (for example, resistive type heating elements that are not shown) by which fluid in the heater bag 153 can be warmed and two insulation pads 158 disposed on opposite sides of the heater bag 153. The one or more heating elements are carried by or otherwise attached to one or both of the plates. The heater assembly 151 also includes a circuit board 159 that provides electronics for operating the heater assembly 151, a feed line 160 for each heating plate 156 that provides power, and thermocouple connections 162 for determining a temperature of the respective heating plates 156.

Figure 15:
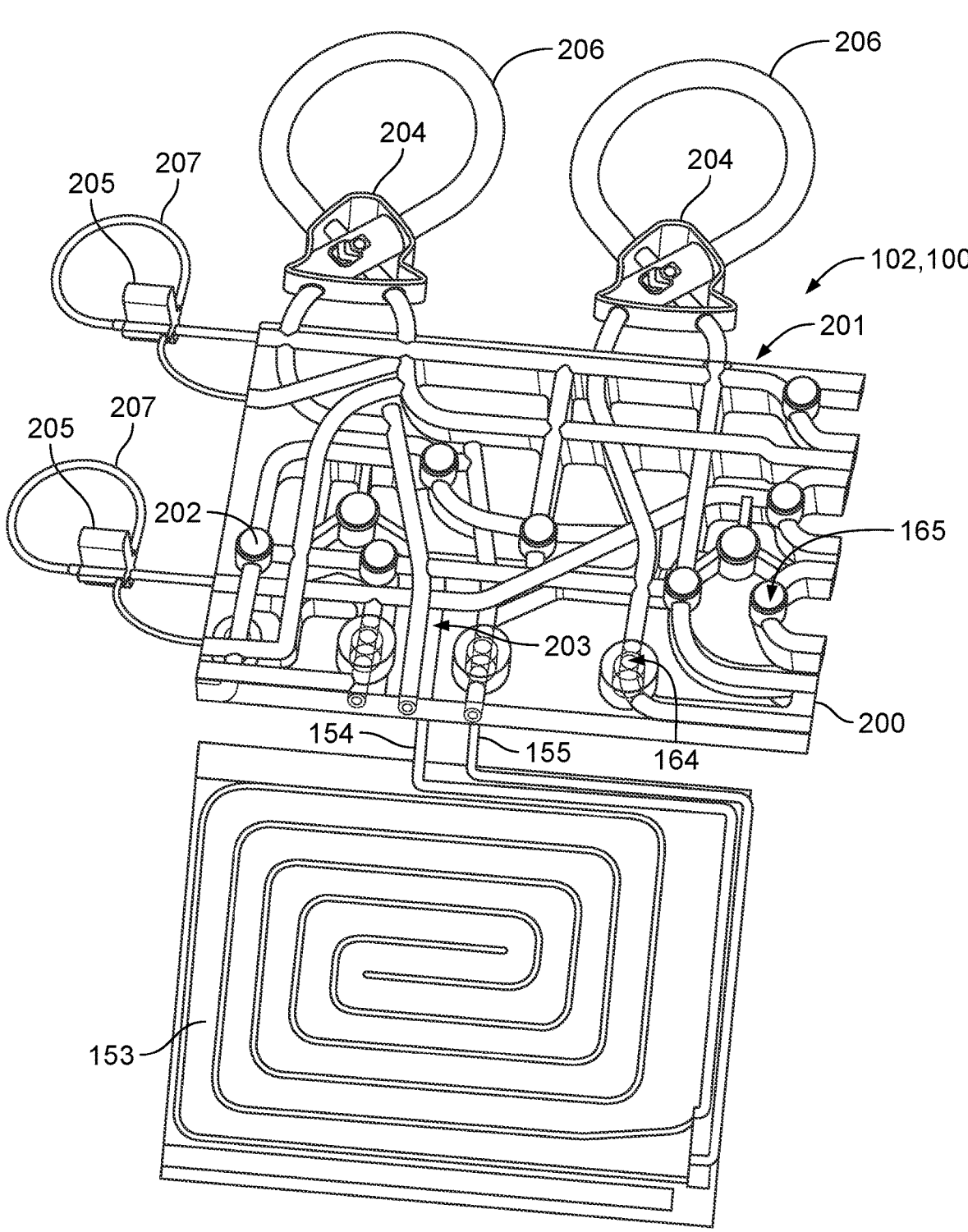
FIG. 15 is a perspective view of the fluid cassette of FIG. 14, along with the heater bag of FIG. 12.
Figure 16:
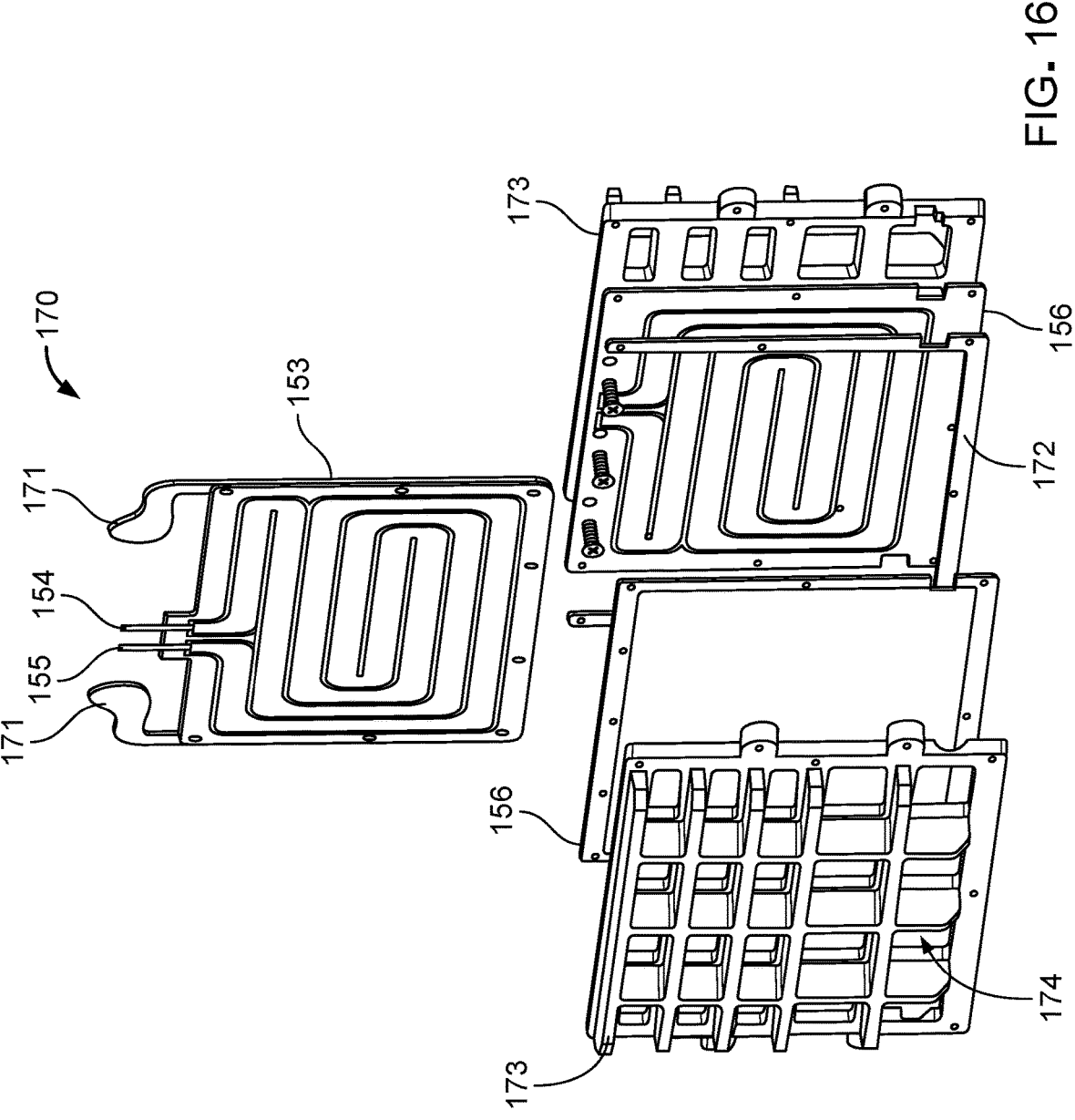
FIG. 16 is a full exploded perspective view of an embodiment of a heater assembly that may be included within the fluid conditioning system of FIG. 1.
Figure 17:
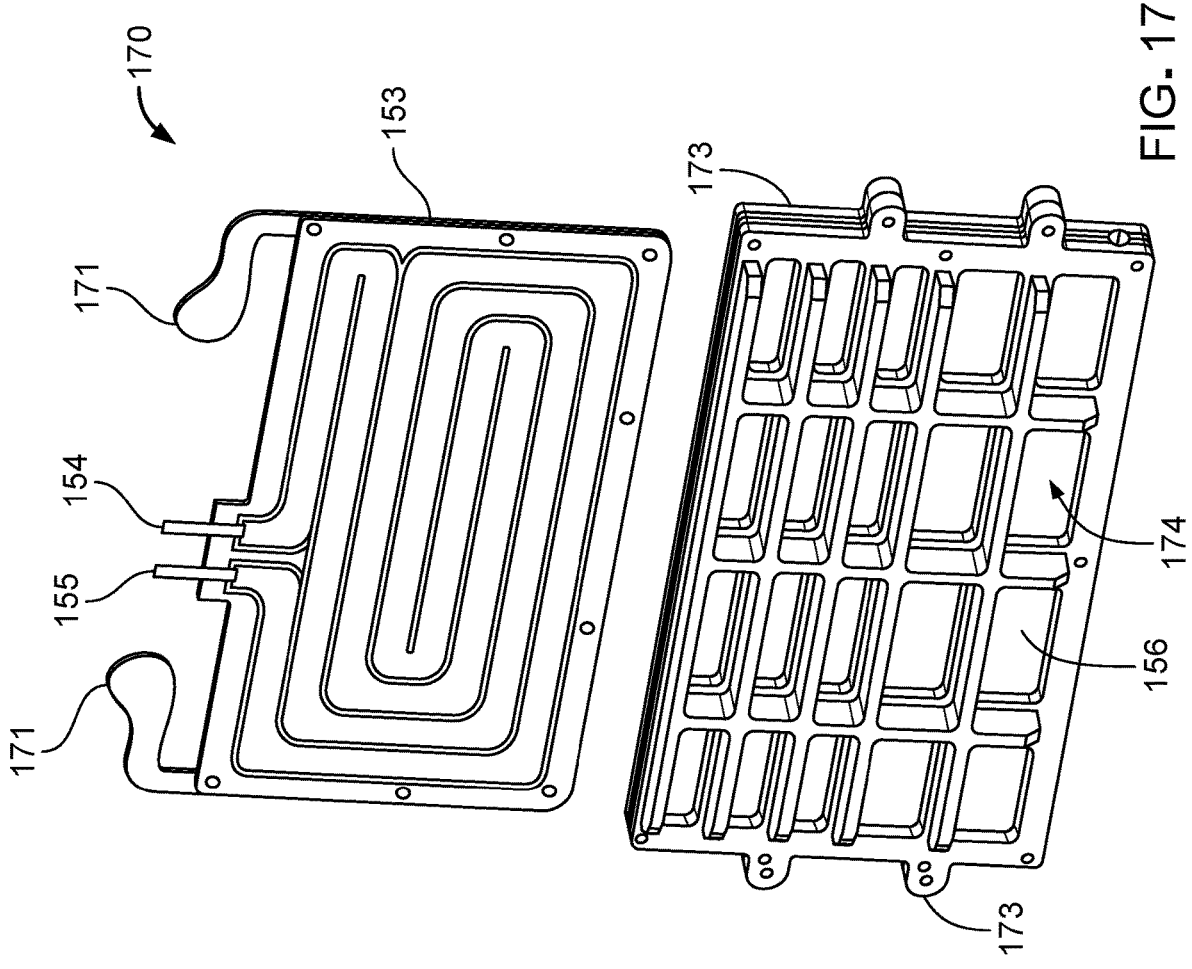
FIG. 17 is a partially exploded perspective view of the heater assembly of FIG. 16.

FIGS. 15 and 16 illustrate another embodiment of a heater assembly 170 that may be included in the fluid conditioning system 100 instead of the heater assembly 151. The heater assembly 170 is similar in construction and function to the heater assembly 151 and accordingly includes the heater bag 153 sandwiched between the two heater plates 156. The heater assembly 170 further includes two handles 171 attached to the heater bag 153 for easy placement of the heater bag 153, a u-shaped heater frame 172 that supports the heater bag 153, and two support members 173 of a generally matrix construction that support the heater plates 156. The support members 173 further serve to insulate the heater bag 153 and the heater plates 156 from surrounding components via air gaps 174 defined by the matrix construction that are disposed between the heater plates 156 and such components.

Referring to FIG. 15, the fluid cassette 102 is a single-use, disposable cartridge that includes a housing 200, multiple fluid lines 201 arranged within the housing 200, multiple valves 202 positioned along the fluid lines 201, two conductivity sensors 203 positioned along the fluid lines 201, an ammonia sensor 165 positioned along the fluid lines 201 for cooperation with the ammonia detector 121, two fluid line connectors (e.g., pump segment clips) 204, and two fluid line connectors (e.g., pump segment clips) 205. The fluid lines 201 cooperate with the heater bag 153 and a dialysis system to form a fluid circuit 350 for carrying out a fluid conditioning cycle. For example, the fluid lines 201 include ports to which the input and output connections 154, 155 of the heater bag 153 can be connected for providing fluid communication between the fluid lines 201 and the heater bag 153. The fluid line connectors 204 locate fluid line segments 206 about the high-capacity pumps 103, and the fluid line connectors 205 locate fluid line segments 207 about the low-capacity pumps 104. The fluid cassette 102 also includes additional fluid lines that extend from the fluid cassette 102 to various fluid containers, as illustrated in FIG. 19.

The valves 202 are three-way valves by which two alternative fluid pathways can be selected by a control system of the fluid conditioning system 100. Lower portions of the valves 202 are formed to engage with the coupling members 131 of the actuators 125 for movement of the valves 202. Example types of valves 202 that may be included in the fluid cassette 102 include rotary valves, push-pull valves, sliding valves, and shuttle valves.

In addition to the components discussed above with respect to FIGS. 1-17, the fluid conditioning system 100 also includes a control system 161 (e.g., including the circuit boards 135, 159, as well as additional circuit boards for sensor circuitry) for controlling various operations of the fluid conditioning system 100 and several other, peripheral components positioned along the fluid circuit 350. These components include a prime tank 302 for collecting water to produce dialysate (e.g., sometimes referred to as dialysis fluid), a sorbent cartridge 303 for filtering tap water to provide purified water suitable for creating dialysate and for cleansing dialysate exiting the hemodialysis system 1, a primary reservoir 304 for collecting fluid (e.g., uncondi-tioned water or dialysate) exiting the sorbent cartridge 303, a secondary reservoir 305 for collecting fluid that exceeds a capacity of the primary reservoir 304, a bag 306 for con-taining an electrolyte solution, a bag 307 for containing a salt-dextrose (SD) solution, a bag 308 for containing dilu-tion water (DW), and a bag 309 for containing a bicarbonate (BC) solution that are positioned along the fluid flow path arrangement 300.

Figure 23:
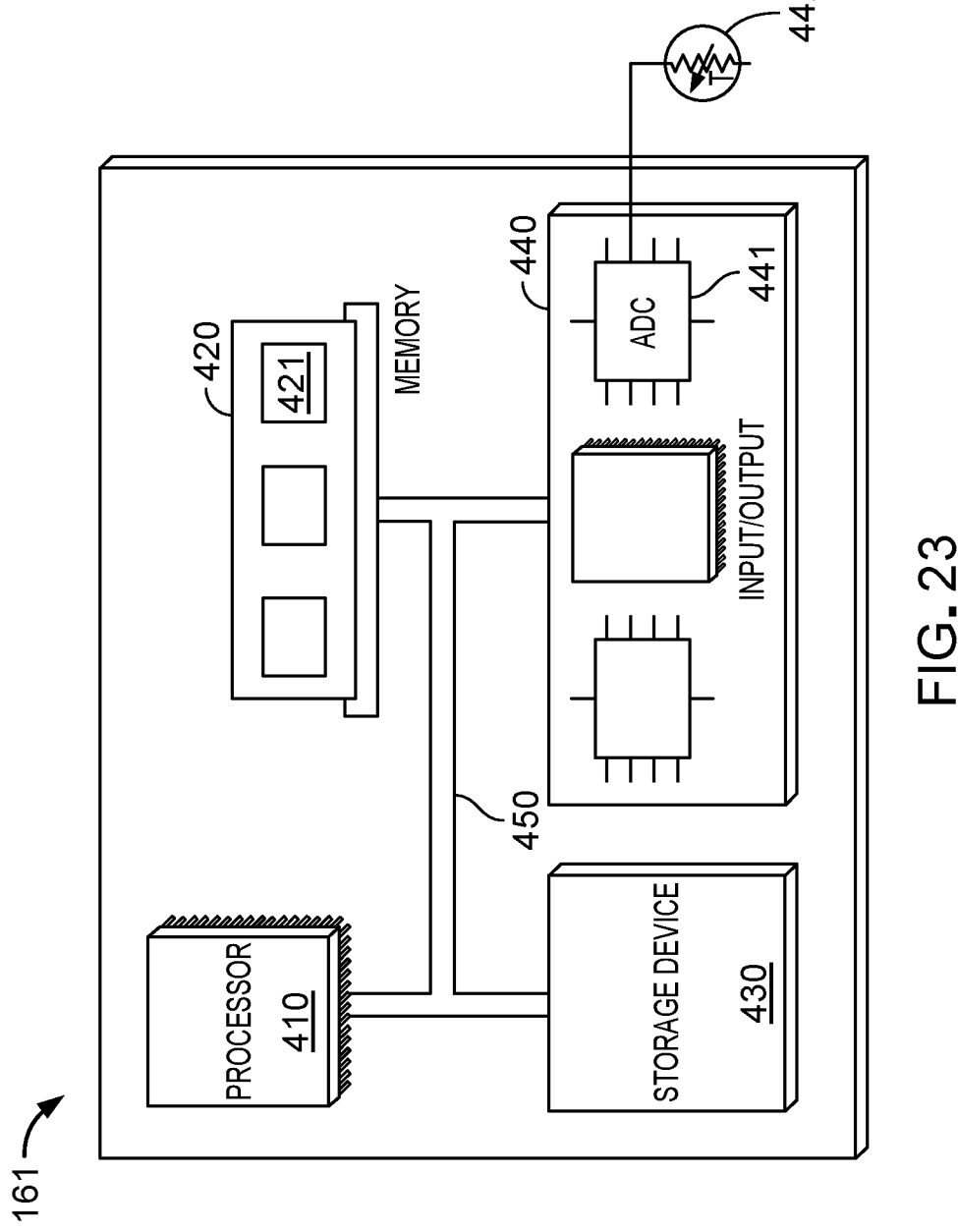
FIG. 23 provides a block diagram of a control system of the fluid conditioning system of FIG. 1.

FIG. 23 provides a block diagram of the control system 161 for the fluid conditioning system 100. The control system 161 includes a processor 410, a memory 420, a storage device 430, and an input/output interface 440. In some embodiments, the control system 161 includes more than one processor 410, memory 420, storage device 430, and/or input/output interface 440. Each of the components 410, 420, 430, and 440 can be interconnected, for example, using a system bus 450. The processor 410 is capable of processing instructions for execution within the control system 161. The processor 410 can be a single-threaded processor, a multi-threaded processor, or a quantum com-puter. The processor 410 is capable of processing instruc-tions stored in the memory 420 or on the storage device 430.

The memory 420 stores information within the control system 161. In some implementations, the memory 420 is a computer-readable medium. The memory 420 can, for example, be a volatile memory unit or a non-volatile memory unit. The storage device 430 is capable of providing mass storage for the control system 161. In some imple-mentations, the storage device 430 is a non-transitory com-puter-readable medium.

The storage device 430 can include, for example, a hard disk device, an optical disk device, a solid-state drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the control system 161. In some implemen-tations, the input/output interface 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementa-tions, the input/output device includes driver devices con-figured to receive input data and send output data to other input/output devices, e.g., keyboard, printer and display devices (e.g., the display screen 148). In some implemen-tations, mobile computing devices, mobile communication devices, and other devices are used.

In some implementations, the input/output interface 440 includes at least one analog-to-digital converter 441. An analog-to-digital converter converts analog signals to digital signals, e.g., digital signals suitable for processing by the processor 410. In some implementations, one or more sens-ing elements are in communication with the analog-to-digital converter 441, as will be discussed in more detail below.

In some implementations, the control system 161 is a microcontroller. A microcontroller is a device that contains multiple elements of a computer system in a single elec-tronics package. For example, the single electronics package could contain the processor 410, the memory 420, the storage device 430, and input/output interfaces 440.

Figures 24, 25:
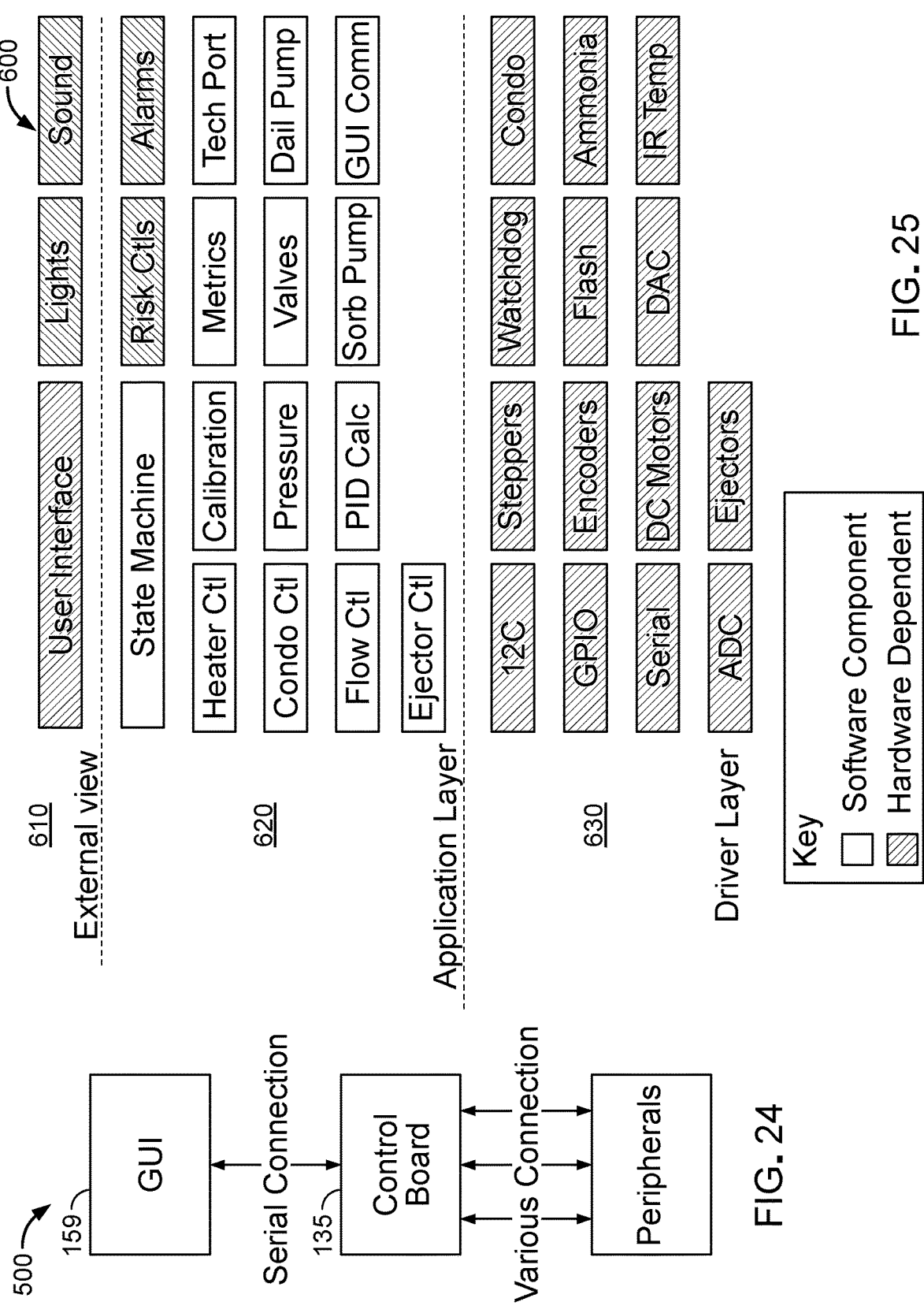
FIG. 24 provides a block diagram of a hardware system of the fluid conditioning system of FIG. 1.
FIG. 25 provides a block diagram of a software system of the fluid conditioning system of FIG. 1.

FIGS. 24 and 25 provide block diagrams of a hardware system 500 and a software system 600 of the fluid condi-tioning system 100 that are provided by the control system 161. As shown in FIG. 24, the hardware system 500 is provided by a circuit board for generating GUIs for display on the display screen 148 and one or more circuit boards 135 for controlling the electromechanical peripheral components of the fluid conditioning system 100, and the various elec-tromechanical peripheral components. The software system 600 can be broken down into an external view 610, an application layer 620, and a driver layer 630. The external view 610 includes user interfaces provided by the GUIs, lights, sounds, and debug ports. The application layer 620 includes business logic, and the driver layer 630 is config-ured to implement peripheral-specific code (e.g., communi-cation protocols and stepper motor drivers).

Referring back to FIG. 19, the hemodialysis system 2 will now be described in greater detail. As discussed above, the hemodialysis system 2 includes the hemodialysis machine 2000 and the disposable set that couples to the hemodialysis machine 2000.

The hemodialysis machine 2000 includes a hemodialysis machine console 2010, a treatment module 2020, and an arm 2080 that connects the treatment module 2020 to the hemo-dialysis machine console 2010. The arm 2080 extends from the hemodialysis machine console 2010, and the treatment module 2020 is mounted to the other end of the arm 2080. In other words, the treatment module 2020 is cantilevered from the hemodialysis machine console 2010 by the arm 2080.

Figure 43:
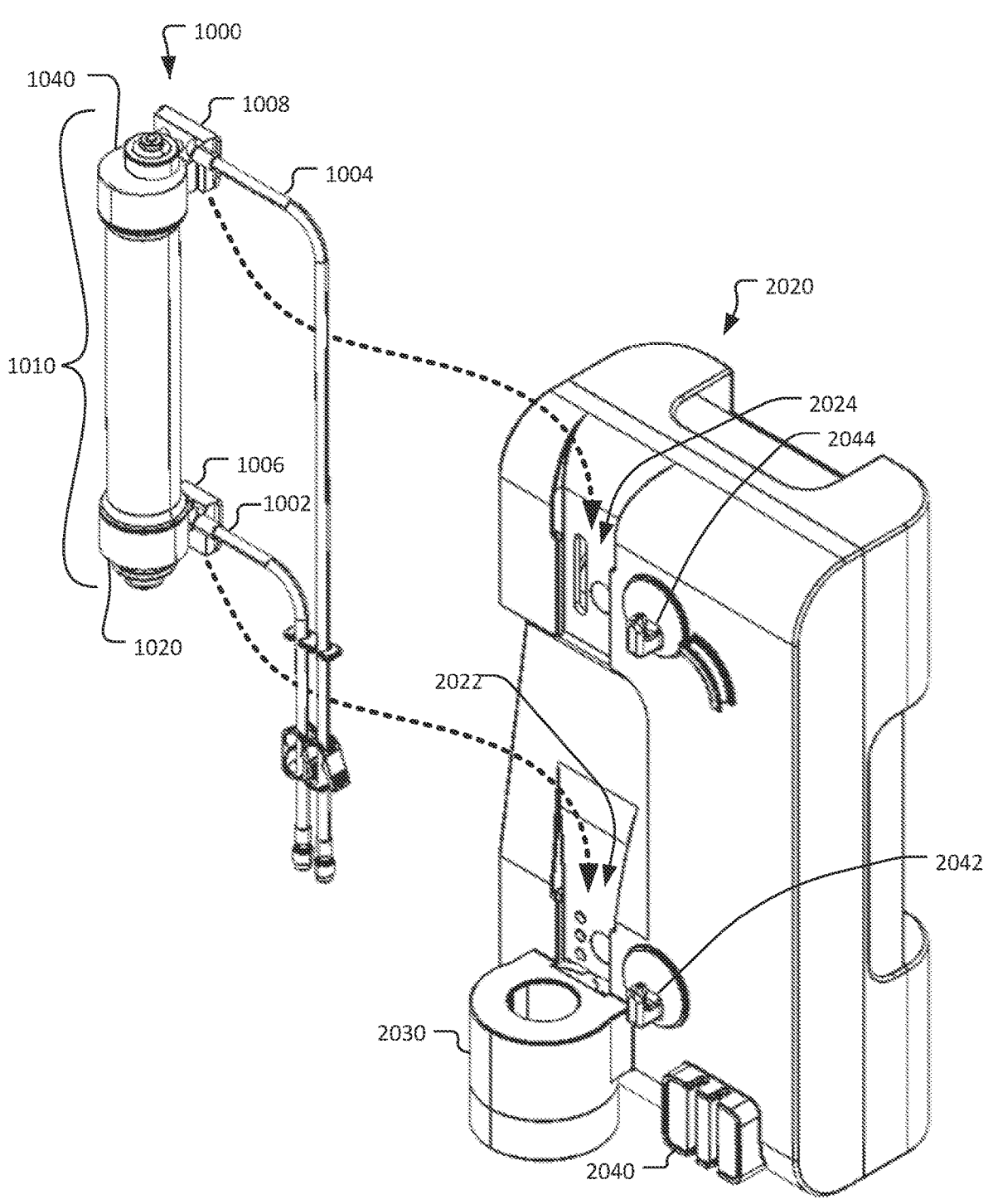
FIG. 43 is an exploded perspective view of a dialyzer and treatment module of the hemodialysis system of FIG. 19.
Figure 44:
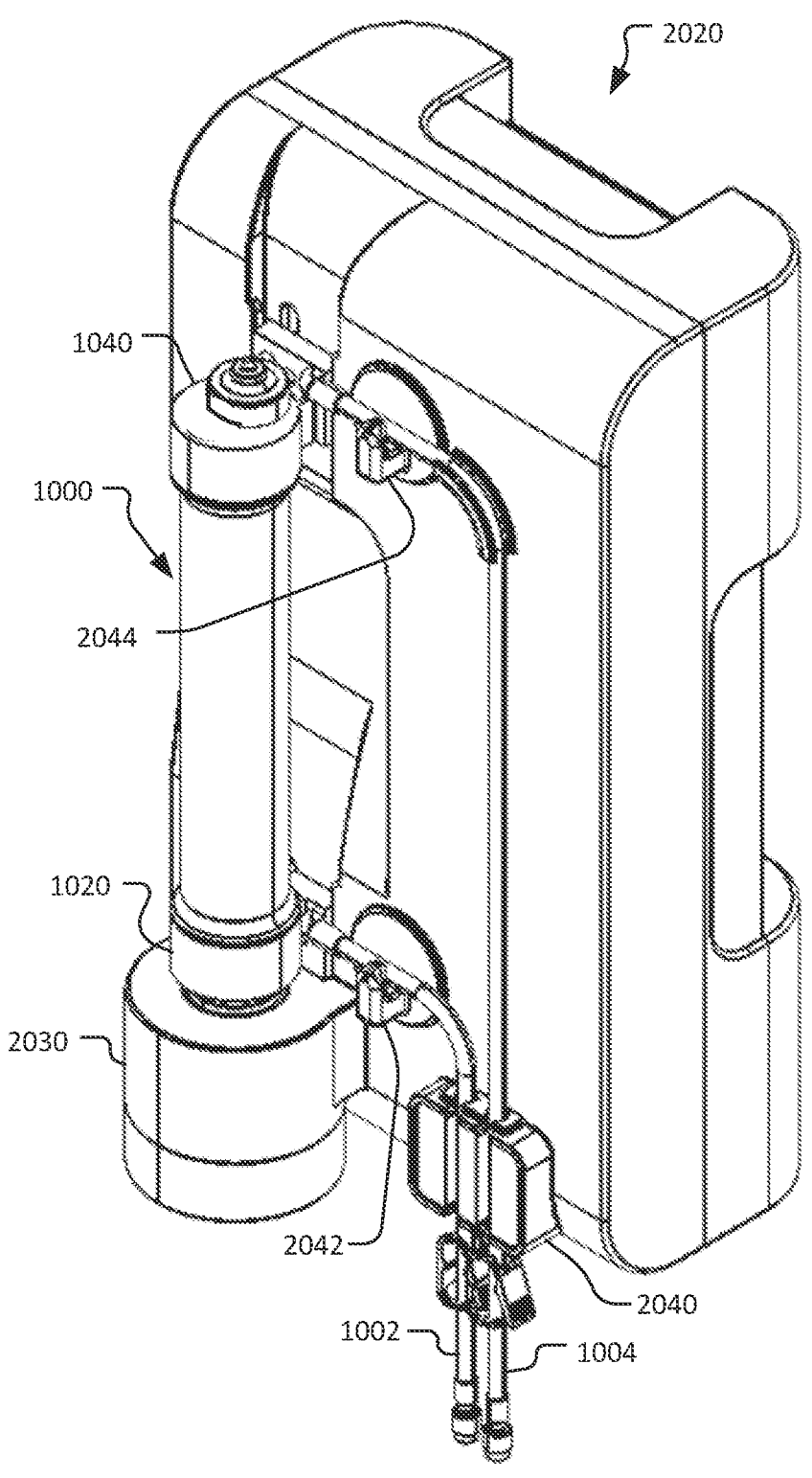
FIG. 44 is a perspective view of the dialyzer and the treatment module of FIG. 43 in a coupled configuration.

Referring to FIGS. 43 and 44, the dialyzer 1000 is releasably coupleable to the treatment module 2020 in a convenient manner. For example, in the depicted embodi-ment, the dialyzer 1000 is slidably coupleable with the treatment module 2020. Accordingly, the dialyzer 1000 and the treatment module 2020 include complementary struc-tural features to facilitate slidable coupling. That is, the dialyzer 1000 includes a first projection 1006 that is slidably coupleable with a first complementarily shaped slot 2022 of the treatment module 2020, and the dialyzer 1000 includes a second projection 1008 that is slidably coupleable with a second complementarily shaped slot 2024 of the treatment module 2020. In some embodiments, other mechanisms for of releasably connecting the dialyzer 1000 to the treatment module 2020 can be used. For example, in some embodi-ments a connection style such as a snap-in connection, a thumb screw connection, a clamp connection, a suction connection, and the like can be used.

The dialyzer 1000 includes a housing 1010 that defines an interior space. A bundle of hollow fiber semi-permeable membranes (or simply "hollow fibers") are disposed within the interior of the housing 1010. The arterial line 1002 and the venous line 1004 each extend from the housing 1010 (e.g., from opposite ends of the housing 1010) and are in fluid communication with the interior of the housing 1010, and with lumens of the hollow fibers.

The housing 1010 includes a first end cap 1020 and a second end cap 1040. The first end cap 1020 includes the first projection 1006 and the second end cap 1040 includes the second projection 1008. Moreover, the arterial line 1002 is coupled to the first end cap 1020 and the venous line 1004 is coupled to the second end cap 1040.

The treatment module 2020 includes a pump drive unit 2030 that is configured to releasably receive a portion of the first end cap 1020. As described further below, the pump drive unit 2030 generates dynamic magnetic fields to levitate and rotate a pump rotor that is housed within the portion of the first end cap 1020. In some embodiments, the pump drive unit 2030 includes no moving parts.

The pump rotor is configured such that rotation of the pump rotor forces blood of the patient 10 through the lumens of the hollow fibers of the dialyzer 1000 in the direction from the first end cap 1020 toward the second end cap 1040. Accordingly, blood from the patient 10 flows into the dialyzer 1000 via the arterial line 1002, flows through the lumens of the hollow fibers, and flows out of the dialyzer 1000 via the venous line 1004.

The treatment module 2020 also includes other devices that interface with the arterial line 1002 and/or the venous line 1004. For example, the depicted treatment module 2020 includes a tubing interface module 2040 configured to releasably receive a portion of the arterial line 1002 and/or a portion of the venous line 1004. The tubing interface module 2040 can include devices that can perform functions such as flow rate detection, gaseous bubble detection, and the like. That is, the tubing interface module 2040 can include sensors for detecting one or more parameters such as a flow rate of the blood within the arterial line 1002 and/or the venous line 1004, hematocrit (Hct) and other blood properties, and/or for detecting gaseous bubbles (e.g., air bubbles) in the blood within the arterial line 1002 and/or the venous line 1004. In some embodiments, the flow rate detection and/or the bubble detection are performed using sensors such as ultrasonic sensors, optical sensors, or other suitable types of sensors. In certain embodiments, sensors for detecting gaseous bubbles can be located at or in an end cap of the disposable of the dialyzer 1000.

The treatment module 2020 also includes an arterial line clamp 2042 and a venous line clamp 2044. The clamps 2042 and 2044 are used to either fully restrict or fully un-restrict (e.g., in an on/off valve fashion) the flow of blood within the arterial line 1002 and/or the venous line 1004, respectively.

The treatment module 2020 also includes devices for interfacing with the dialyzer 1000 to measure pressure at particular locations within the dialyzer 1000, as described further below. Additionally, as described further below, the treatment module 2020 includes conduits that can selectively interface with the dialyzer 1000 to facilitate flow of liquids such as substituate and/or dialysate between the dialyzer 1000 and the treatment module 2020.

Figure 45:
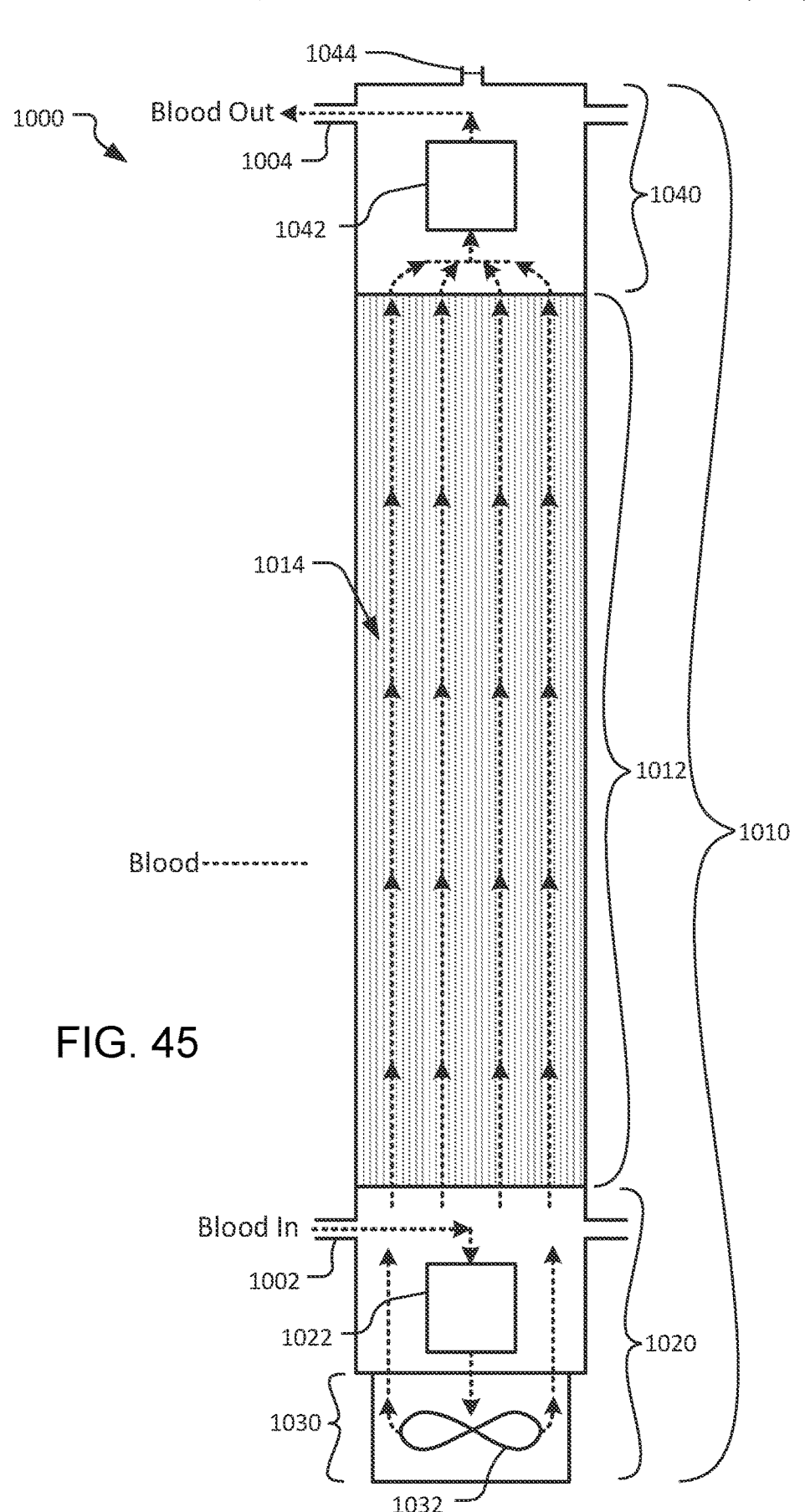
FIG. 45 is a schematic depiction of the dialyzer of the hemodialysis system of FIG. 19, showing the blood flow path through the dialyzer.
Figure 46:
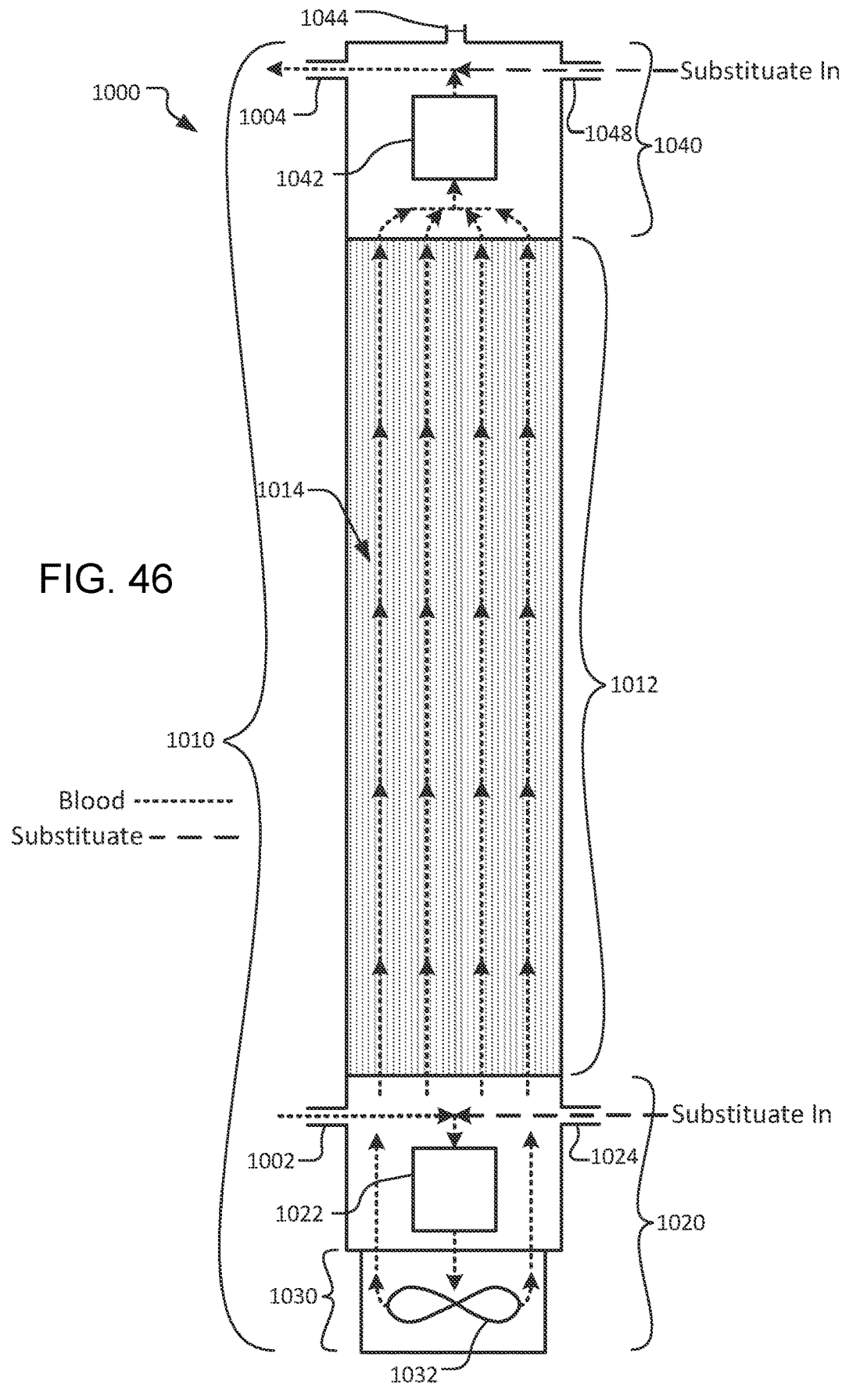
FIG. 46 is another schematic depiction of the dialyzer of the hemodialysis system of FIG. 19, showing the blood flow path through the dialyzer and substituate addition locations.
Figure 47:
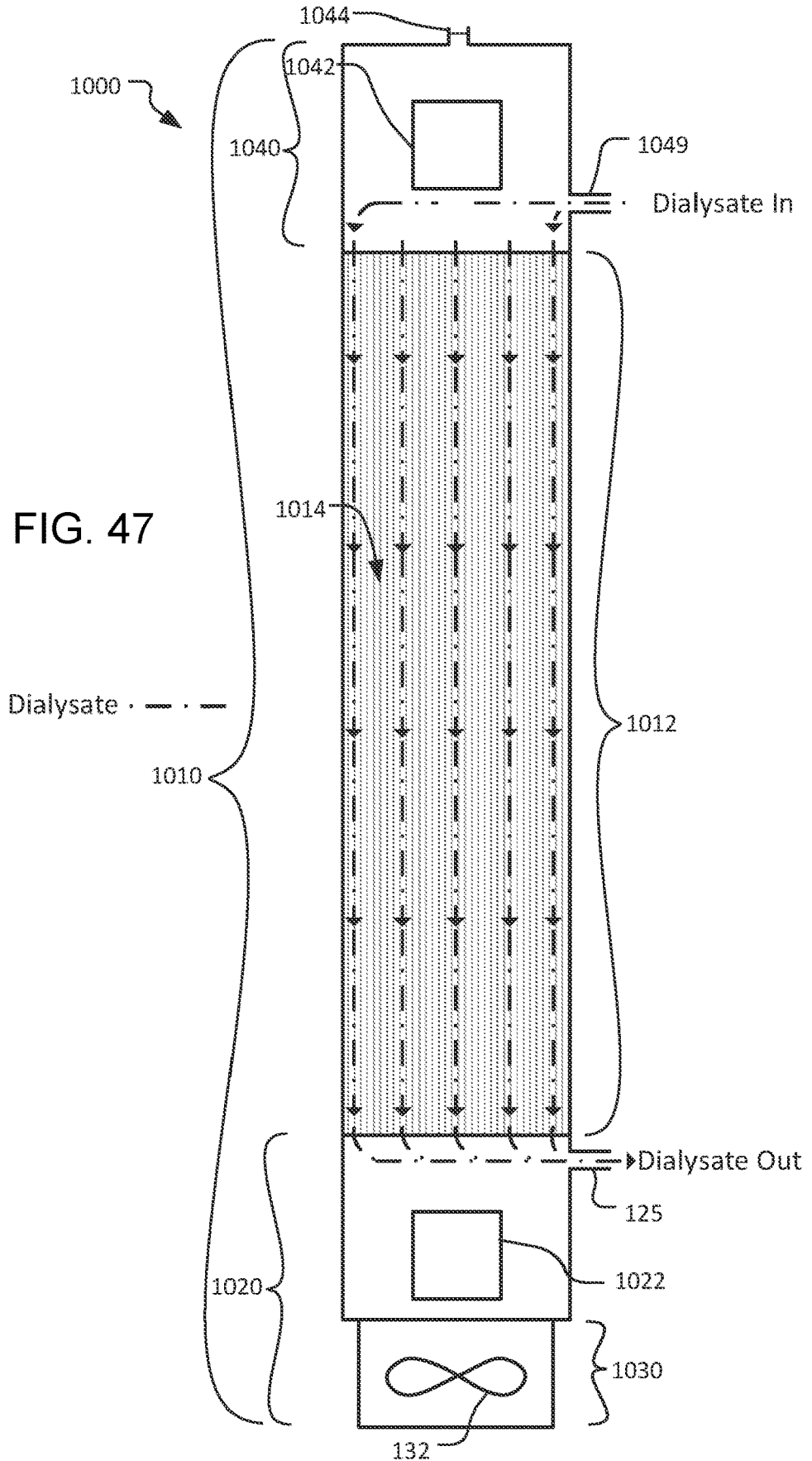
FIG. 47 is another schematic depiction of the dialyzer of the hemodialysis system of FIG. 19, showing the dialysate flow path through the dialyzer.
Figure 48:
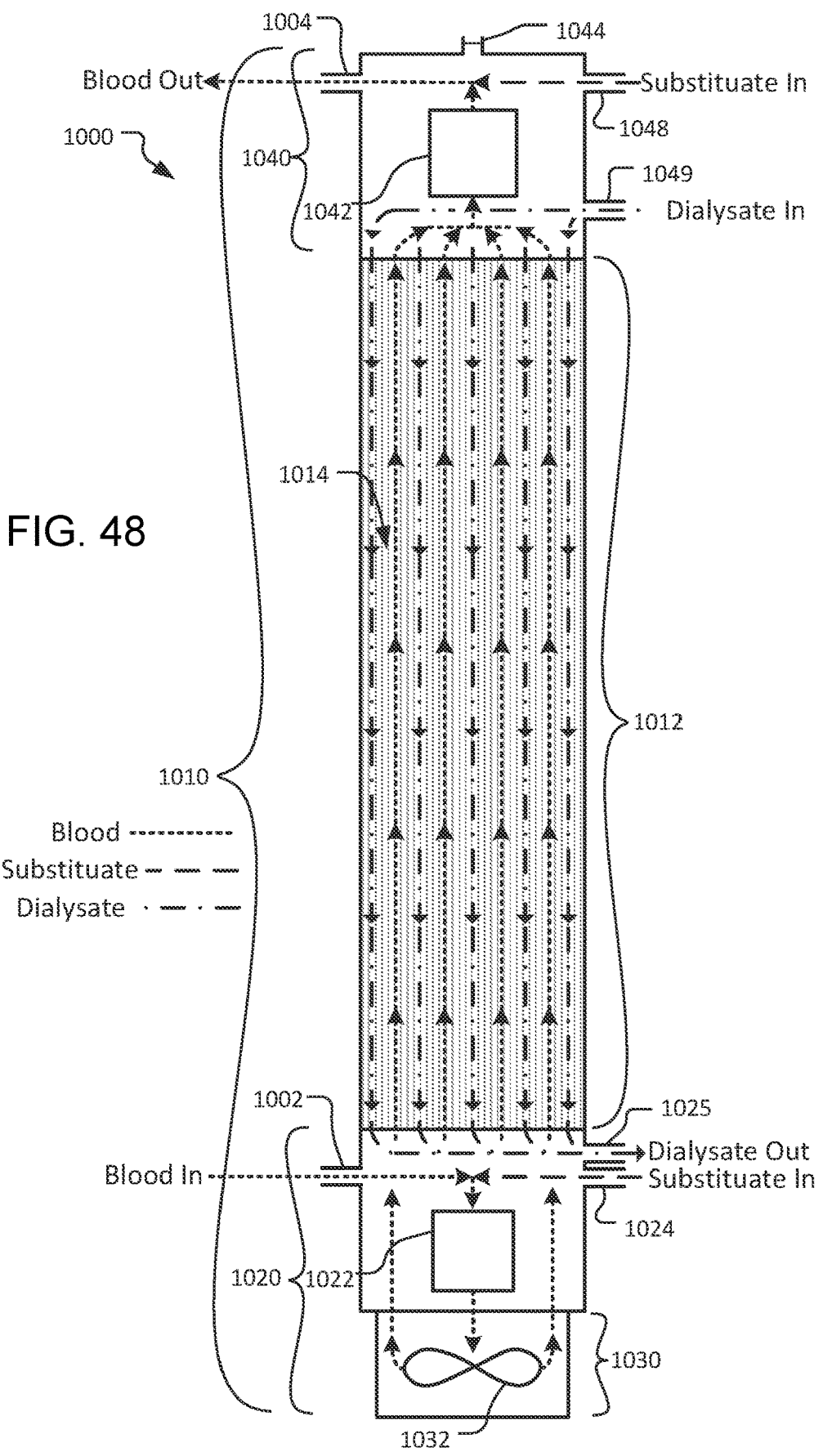
FIG. 48 is another schematic depiction of the dialyzer of the hemodialysis system of FIG. 19, showing the blood and dialysate flow paths and the substituate addition locations.

FIGS. 45-48 are schematic diagrams of the dialyzer 1000. For ease of understanding, FIG. 45 depicts exclusively the flow of blood through the dialyzer 1000; FIG. 46 depicts the flow of blood and substituate; FIG. 47 depicts exclusively the flow of dialysate; and FIG. 48 depicts the flow of blood, substituate, and dialysate.

FIGS. 45-48 are simplified to show general flow relationships in the dialyzer 1000. For example, a first potting and a second potting, which secure the two respective ends of each of the fibers of the bundle of hollow fibers 1014, are omitted to simplify the illustration. In addition to securing the bundle of hollow fibers, these pottings, maintain a barrier between the blood and the dialysate.

Referring to FIG. 45, the housing 1010 of the dialyzer 1000 includes the first end cap 1020, the second end cap 1040, and a middle housing portion 1012 that extends between the first end cap 1020 and the second end cap 1040. The middle housing portion 1012 contains the majority of the length of the bundle of hollow fibers 1014.

The first end cap 1020 includes a pump housing 1030. A rotatable centrifugal pump rotor 1032 is located within the pump housing 1030. The pump rotor 1032 is enclosed or encased within the pump housing 1030. Accordingly, the pump rotor 1032 is contained in a pumping chamber that is at a fixed position relative to the bundle of hollow fibers 1014. However, the pump rotor 1032 levitates in response to the magnetic field created by the pump drive unit 2030 so the pump rotor 1032 can move.

In accordance with some embodiments, the pump rotor 1032 is a radially pumping pump wheel with a hollow central volume. The blades (or vanes) of the pump wheel of the pump rotor 1032 are arranged so that they project or extend at least partially radially. In some cases, the blades are arranged to project or extend entirely radially. In some cases, the blades are arranged to project or extend partially radially and partially tangentially.

As described further herein, the pump rotor 1032 is operated and controlled by interfacing with the pump drive unit 2030 (shown in FIGS. 43 and 44) of the treatment module 2020. That is, the pump rotor 1032 can be levitated and rotated by magnetic fields that are caused to emanate from the pump drive unit 2030 during use.

The housing 1010 defines one or more pressure detection chambers. The depicted embodiment includes an arterial pressure detection chamber 1022 and a venous pressure detection chamber 1042. The arterial pressure detection chamber 1022 is located prior to the pump rotor 1032 along the blood flow path. That is, the arterial pressure detection chamber 1022 is arranged to facilitate measuring pre-pump arterial pressure. Additionally or alternatively, in some embodiments, pressure can be measured post-pump (but prior to the hollow fibers 1014). The pressure detection chambers 1022 and 1042 are each configured to interface with a respective pressure transducer of the treatment module 2020 to measure the pressure of the blood moving through the dialyzer 1000.

The flow path of blood through the dialyzer 1000 will now be explained in reference to the dashed lines shown in FIG. 45. Blood flows into the first end cap 1020 via the arterial line 1002 (shown in FIGS. 43 and 44). The fluid flow path entering the first end cap 1020 is transverse to a longitudinal axis of the dialyzer 1000. The arterial pressure detection chamber 1022 is located along the flow path after entering the first end cap 1020 but prior to the pump rotor 1032. The blood flow path transitions to parallel to the longitudinal axis of the dialyzer 1000 to deliver the blood to the pump rotor 1032. The blood is directed to a center of the pump rotor 1032. Rotations of the centrifugal pump rotor 1032 force the blood radially outward from the pump rotor 1032. Then, after flowing radially outward from the pump rotor 1032, the blood turns and flows longitudinally toward the middle housing portion 1012. The blood enters the lumens of the bundle of hollow fibers 1014 and continues flowing longitudinally toward the second end cap 1040. After passing through the middle housing portion 1012, the blood exits the bundle of hollow fibers 1014, enters the second end cap 1040, and flows transversely out of the second end cap 1040 via the venous line 1004. The venous pressure detection chamber 1042 is located along the blood flow path in the second end cap 1040. In some embodiments, a one-way check valve is located along the blood flow path as the blood exits the second end cap 1040 into the venous line 1004. In some embodiments, a one-way check valve is included on side-arm connections to the blood flow pathway to prevent back-fluid flow or blood entering the side arm connection.

The second end cap 1040 can also be configured to deaerate the blood as it enters and flows through the second end cap 1040. Accordingly, the second end cap 1040 includes an air purge member 1044 that allows air and other gases to exit the second end cap 1040 while preventing fluids such as blood from exiting therethrough. The air purge member 1044 can also be used as an access port. That is, the air purge member 1044 can be configured for uses such as sample extraction and administration of medicaments (e.g., heparin). The air purge member 1044 can comprise a plastic tube extending from the second end cap 1040. An elastomeric seal member located within the plastic tube is configured to open when a syringe without a needle is coupled with the air purge member 1044.

Referring to FIG. 46, the dialyzer 1000 is also configured to receive one or more additions of substituate fluid that are combined with the blood within the dialyzer 1000. For example, in the depicted embodiment, the first end cap 1020 defines a first substituate liquid port 1024 and the second end cap 1040 defines a second substituate liquid port 1048. The first substituate liquid port 1024 is in direct fluid communication with the incoming blood flow path defined by the first end cap 1020 and is confluent therewith prior to the arterial pressure detection chamber 1022. Alternatively, in some embodiments substituate fluid can be added to the blood after exiting the pump housing 1030 (i.e., after being pressurized by the pump rotor 1032) but prior to entering the lumens of the hollow fibers 1014. The second substituate liquid port 1048 is in direct fluid communication with the outgoing blood flow path defined by the second end cap 1040, and is confluent therewith after the venous pressure detection chamber 1042. Each of the substituate liquid ports 1024 and 1048 can include a respective one-way check valve therein that prevents liquid from exiting the end caps 1020 and 1040 via the substituate liquid ports 1024 and 1048.

Referring to FIG. 47, the dialyzer 1000 is also configured to receive dialysate (e.g., from the fluid conditioning system 100 shown in FIG. 19), and to direct the dialysate to flow through the housing 1010. For example, in the depicted embodiment, the second end cap 1040 defines a dialysate inlet port 1049 and the first end cap 1020 defines a dialysate outlet port 1025. The dialysate flows into the second end cap 1040 via the dialysate inlet port 1049, and then enters the middle housing portion 1012 containing the bundle of hollow fibers 1014. The dialysate flows through the middle housing portion 1012 via the spaces defined between the outer diameters of the fibers of the bundle of hollow fibers 1014. In other words, while the blood flows within the lumens of the fibers of the bundle of hollow fibers 1014, the dialysate liquid flows along the outsides of the fibers. The semi-permeable walls of the fibers of the bundle of hollow fibers 1014 separate the dialysate liquid from the blood. The dialysate liquid flows out of the middle housing portion 1012 and into the first end cap 1020. The dialysate liquid exits the first end cap 1020 via the dialysate outlet port 1025. For example, the dialysate may return to the fluid conditioning system 100 for cleaning and recycling.

Referring to FIG. 48, the flow paths of blood, substituate, and dialysate (as each are described in reference to FIGS.

45-47 above) are now shown in combination (e.g., as would occur during use of the dialyzer 1000). When substituate is added, the substituate is combined directly with the blood in the end cap(s) 1020 and/or 1040. In contrast, the dialyzer 1000 keeps the dialysate separated from the blood. However, waste products from the blood (e.g., urea, creatinine, potassium, and extra fluid) are transferred by diffusion and/or ultrafiltration (convection) from the blood to the dialysate through the semi-permeable walls of the fibers of the bundle of hollow fibers 1014 in the dialyzer 1000. The dialysate can subsequently be cleaned and recycled using a fluid conditioning system.

Additional details about the hemodialysis machine 2000 and the dialyzer 1000 can be found in U.S. Patent Application Ser. No. 62/934,274 ("Blood Treatment Systems") filed on Nov. 12, 2019, the entire contents of which are wholly incorporated by reference herein.

Figure 18:
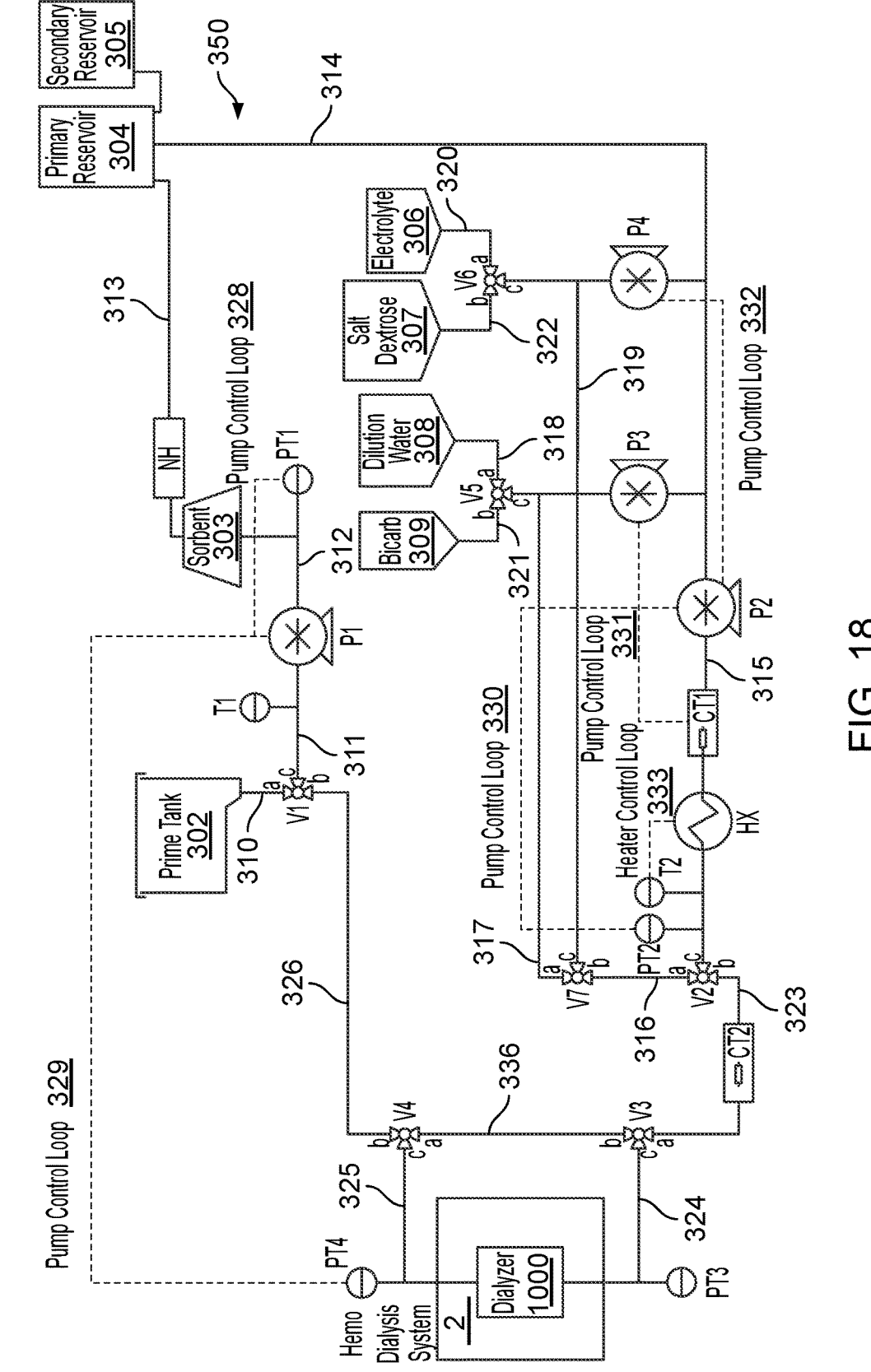
FIG. 18 provides an operational diagram by which the fluid conditioning system of FIG. 1 can cooperate with a hemodialysis system to form a fluid circuit for carrying out the fluid conditioning cycle.

The operation of the system 1 will now be described. FIG. 18 illustrates an operational diagram 300 by which the fluid conditioning system 100 cooperates with the dialyzer 1000 of the hemodialysis system 2 to form the fluid circuit 350 (indicated by solids lines) for carrying out a fluid conditioning cycle, while FIG. 19, as discussed above, illustrates the setup of the fluid conditioning system 100 connected to the hemodialysis system 2. The fluid circuit 350 incorporates components of the fluid cassette 102, as well as various other components of the fluid conditioning system 100.

The bags 306, 307, 309 are pre-loaded with appropriate amounts of dry chemicals that can be dissolved in water to produce the electrolyte solution, the salt-dextrose solution, and the bicarbonate solution. Each bag 306, 307, 309 includes a nozzle that is designed to increase a velocity of a fluid flow entering the bag 306, 307, 309 and to create turbulence needed for adequate mixing and dissolution of the dry chemicals in water.

Table 1 lists approximate capacities of the various fluid-containing components of the fluid conditioning system 100.

TABLE 1

| Capacities of fluid-containing components of the fluid conditioning system 100. | |
| --- | --- |
| Component | Capacity (mL) |
| Prime Tank (302) | 8,000 |
| Primary Reservoir (304) | 7,500 |
| Secondary Reservoir (305) | 4,500 |
| Electrolyte Bag (306) | 500 |
| Salt/Dextrose Bag (307) | 160 |
| Dilution Water Bag (308) | 4,000 |
| Bicarbonate Bag (309) | 1,000 |

The three-way valves 202 of the fluid cassette 102 are indicated as V1-V7 in the fluid circuit 350. Each valve includes three fluid ports (a), (b), (c) by which a flow path in the valve can be adjusted. A valve may be referred to as closed when two or three of its ports are closed and may be referred to as open when two or three of its ports are open. The valves include a prime valve V1, a dissolution valve V2, a bypass out valve V3, a bypass in valve V4, a BC/DW valve V5, an S/D/Electrolyte valve V6, and a fluid selector valve V7 The fluid lines 201 of the fluid cassette 102 will be referenced individually further below with respect to an operation of the fluid conditioning system 100. The high-capacity pumps 103 and the low-capacity pump 104 of the fluid conditioning system 100 are indicated respectively as P1, P2 and P3, P4 in the fluid circuit 350. The pumps include a cassette-in pump P1, a dialysate pump P2, a conductivity control pump P3, and an electrolyte/salt-dextrose pump P4. Table 2 lists approximate operational (e.g., fluid flow rate) ranges of the pumps P1-P4.

TABLE 2

| Operational ranges of pumps of the fluid conditioning system 100. | |
| --- | --- |
| Pump | Operational Range (mL/min) |
| P1 | 20-600 |
| P2 | 20-600 |
| P3 | 0.5-90 |
| P4 | 0.5-90 |

The heater assembly 151 and the ammonia sensor 165 of the fluid conditioning system 100 are respectively indicated as a heat exchanger HX and an ammonia sensor NH in the fluid circuit 350. The conductivity sensors 203 of the fluid cassette 102 are indicated as a conductivity sensor CT1 associated with a fluid temperature upstream of the heat exchanger HX and a conductivity sensor CT2 associated with a fluid temperature downstream of the heat exchanger HX. In addition to having a capability to measure fluid conductivity, conductivity sensors CT1 and CT2 also have a capability to measure fluid temperature. Given that conductivity changes with temperature, the temperatures measured by the conductivity sensors CT1 and CT2 may, in some implementations, be used to correct conductivity values measured by the conductivity sensors CT1 and CT2 to provide temperature-compensated conductivity measurements. In some implementations, a fluid temperature measured by the conductivity sensor CT2 may also provide a safety check on a final temperature of dialysate that exits the fluid conditioning system 100 to flow into the hemodialysis system 1. The temperature sensors 120 of the fluid conditioning system 100 are indicated as a cassette-in temperature sensor T1 and a heat exchanger temperature sensor T2 in the fluid circuit 350. The pressure transducers 119 of the fluid conditioning system 100 are indicated as pressure transducers PT1, PT2, PT3, and PT4 in the fluid circuit 350.

The fluid conditioning system 100 can be operated in multiple stages to cooperate with the hemodialysis system 2 (e.g., with the dialyzer 1000) for carrying out a fluid conditioning cycle in which a hemodialysis treatment is administered to a patient 10 via the hemodialysis system 2. For example, the fluid conditioning cycle includes a priming stage, an infusion stage, and a treatment stage. The fluid conditioning cycle typically has a total duration of about 135 min to about 300 min.

Figure 20:
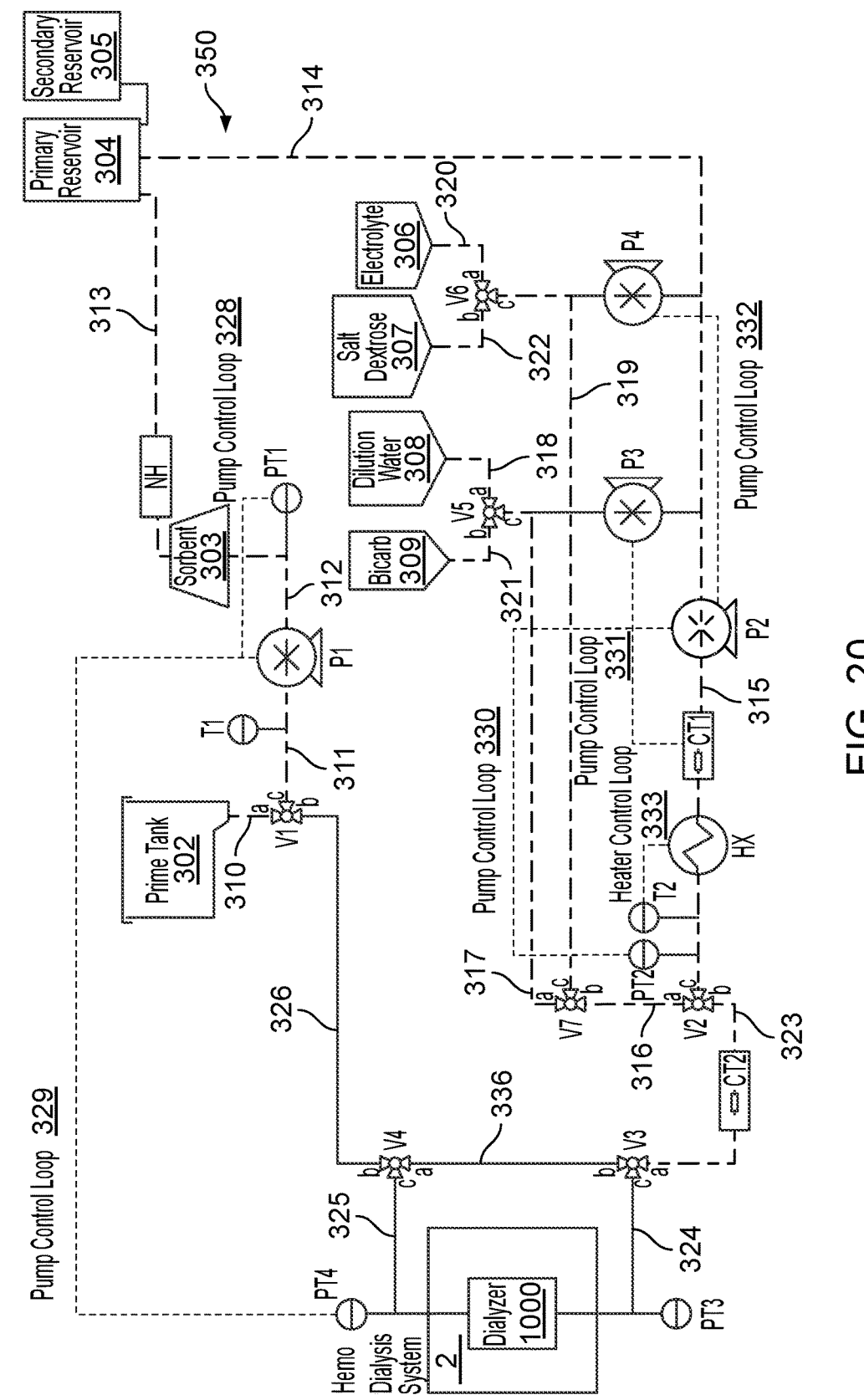
FIG. 20 illustrates a fluid flow path (indicated by highlighted fluid lines) of a priming stage of the fluid conditioning cycle carried out via the fluid circuit of FIG. 16.

FIG. 20 illustrates operation of the fluid conditioning system 100 during the priming stage, in which an initial volume of water is drawn into the fluid circuit 350 for subsequent creation of dialysate. At the beginning of the priming stage, the prime tank 302 is filled to about 7.6 L with water (e.g., tap water, bottled water, reverse osmosis water, distilled water, or drinking water) from a water source (e.g., a container 340 of water, shown in FIG. 19), pump P1 is turned on, and heat exchanger HX is turned on. The water is pumped by pump P1 from the prime tank 302 into a fluid line 310, through ports (a) and (c) of valve V1, into a fluid line 311, past temperature sensor T1, and into pump P1. At this stage of operation, pump P1 pumps water at a flow rate in a range of about 200 m/min to about 600 m/min, and heat exchanger HX is powered to maintain a fluid temperature at a set point in a range of about 15° C. to about 42° C.

If temperature sensor T1 detects a water temperature of greater than about 42° C., then a message is displayed on the display screen 148 to advise a user that the water temperature is too warm, valve V1 is closed, and pump P1 is turned off to prevent additional water from entering the fluid circuit 350. If temperature sensor T1 detects a water temperature of less than or equal to about 42° C., then ports (a) and (c) of valve V1 remain open, and pump P1 pumps the water through a fluid line 312 into the sorbent cartridge 303, into a fluid line 313, past ammonia sensor NH, and into the primary reservoir 304. At this stage of operation, the sorbent cartridge 303 purifies the water circulating in the fluid circuit 350, such that the water meets or exceeds water quality standards for drinking water as set by the Environmental Protection Agency (EPA) and water quality standards for hemodialysis water as set by the Association for the Advancement of Medical Instrumentation (AAMI) standard.

Once the primary reservoir 304 collects about 100 mL to about 500 mL of water, then pump P2 is turned on and pumps water into a fluid line 314, through pump P2, into a fluid line 315, past conductivity sensor CT1, and past the heat exchanger HX1, which heats the water in the fluid line 315 to the set point temperature. Pump P2 is controlled to pump water at a flow rate that is about equal to the flow rate at which water is pumped by pump P1. Water moves from the fluid line 315 through ports (c) and (a) of valve V2, into a fluid line 316, through ports (b) and (a) of valve V7, into a fluid line 317, through ports (c) and (a) of valve V5, into a fluid line 318, and further into the bag 308 until the bag 308 is filled to about 3.5 L to about 4.0 L with water (e.g., dilution water).

Next, ports (a) and (c) of valve V5 are closed, port (a) of valve V7 is closed, and port (c) of valve V7 is opened such that the pump P2 pumps water into a fluid line 319, through ports (c) and (a) of valve V6, into a fluid line 320, and further into the bag 306 until the bag 306 is filled to capacity with water to produce the electrolyte solution. Ports (a) and (c) of valve V6 are closed, port (c) of valve V7 is closed, port (a) of valve V7 is reopened, and ports (b) and (c) of valve V5 are opened. Pump P2 then pumps water into the fluid line 317, through ports (c) and (b) of valve V5, into a fluid line 321, and further into the bag 309 until the bag 309 is filled to capacity with water to produce the bicarbonate solution.

At this point in the priming stage, the set point temperature of the heat exchanger HX is increased to a range of about 31° C. to about 39° C. (e.g., where 39° C. is the maximum temperature achievable by heat exchanger HX), and the flow rate of pump P2 is reduced to a value within a range of about 100 mL/min to about 300 mL/min to increase an exposure time of the water within the heat exchanger HX for achieving the higher set point temperature. Ports (b) and (c) of valve V5 are closed, port (a) of valve V7 is closed, port (c) of valve V7 is opened, and ports (b) and (c) of valve V6 are opened. Accordingly, pump P2 pumps water into the fluid line 319, though ports (c) and (b) of valve V6, into a fluid line 322, and further into the bag 307 until the bag 307 is filled to capacity to produce the salt-dextrose solution. The higher set point temperature of heat exchanger HX facilitates dissolution of the salt-dextrose substance with the water flowing into the bag 309. At this point during the fluid conditioning cycle, the priming stage concludes, the prime tank 302 has substantially emptied, the pumps P1, P2 are turned off and the infusion stage can begin. The priming stage typically lasts a duration of about 10 min to about 30 min (e.g., about 20 min).

Figure 21:
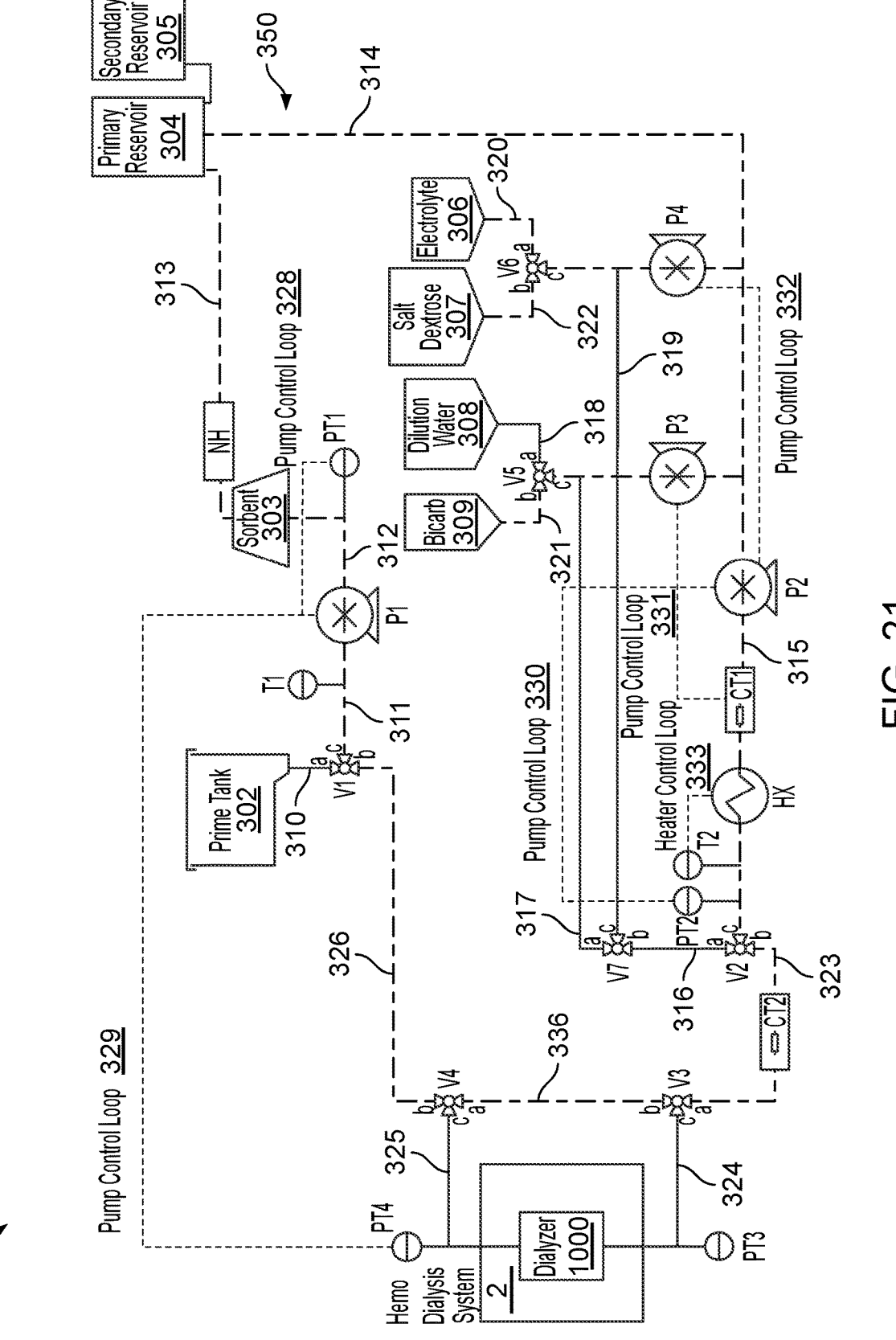
FIG. 21 illustrates a fluid flow path (indicated by highlighted fluid lines) of an infusion stage of the fluid conditioning cycle carried out via the fluid circuit of FIG. 16.

FIG. 21 illustrates operation of the fluid conditioning system 100 during the infusion stage, in which bicarbonate, salt, and dextrose are added to the water in the fluid circuit 350 to produce dialysate. In particular, bicarbonate, salt, and dextrose are added to the water in a controlled manner (e.g., under flow rate control) until the salt and dextrose reach physiologically acceptable concentrations and until the bicarbonate yields a physiologically acceptable fluid conductivity and fluid pH. During the infusion stage, heat exchanger HX is powered to maintain a fluid temperature at a set point in a range of about 35° C. to about 39° C.

At the beginning of the infusion stage, valve V7 is closed, port (a) of valve V2 closes, port (b) of valve V2 opens, ports (a) and (b) of both valves V3 and V4 open, port (b) of valve V1 opens, port (a) of valve V1 closes, ports (b) and (c) of valve V6 remain open, and ports (b) and (c) of valve V5 open. Pumps P1, P2 immediately turn on to pump water at a flow rate in a range of about 300 mL/min to about 600 m/min within the fluid circuit 350. At the same time, pumps P3 and P4 are turned on. Pump P3 pumps bicarbonate solution out of the bag 309 at a flow rate of about 10 mL/min to about 100 mL/min, into the fluid line 317, through the pump P3, and into the fluid line 314. Pump P4 pumps salt-dextrose solution out of the bag 307 at a variable flow rate into the fluid line 319, through pump P4, and into the fluid line 314. The flow rate at which P4 initially pumps fluid is in a range of about 1 mL/min to about 100 m/min. The flow rate is gradually stepped down by a factor of 2 at periodic time increments of about 1 min. The flow rates of pumps P3 and P4 are set to completely add the infusion volume respectively of the BC solution and the SD solution over a single revolution around the fluid circuit 350. Accordingly, the flow rates of pumps P3 and P4 depend on the flow rates of pumps P1 and P2 during the infusion stage. For example, if the flow rates of pumps P1 and P2 are set to 200 m/min, then the flow rates of pumps P3 and P4 will be relatively slow. Conversely, if the flow rates of pumps P1 and P2 are set to 600 mL/min, then the flow rates of pumps P3 and P4 will be relatively fast.

Once the bag 307 empties of the salt-dextrose solution, port (b) of valve V6 closes, and port (a) of valve V6 opens to allow pump P4 to pump the electrolyte solution out of the bag 306 at a flow rate of about 0.5 m/min to about 5 m/min into the fluid line 314. Once the electrolyte solution reaches valve V3, the infusion stage concludes, and the treatment stage can begin. However, if the treatment stage does not begin immediately, the fluid conditioning system 100 can be operated to continue to circulate dialysate around the fluid circuit 350 through fluid lines 311, 312, 313, 314, 315, 323, 336, 326 or to allow the dialysate to remain static (e.g., without circulation) until the treatment stage begins. The infusing stage typically lasts a duration of about 5 min to about 6 min.

Figure 22:
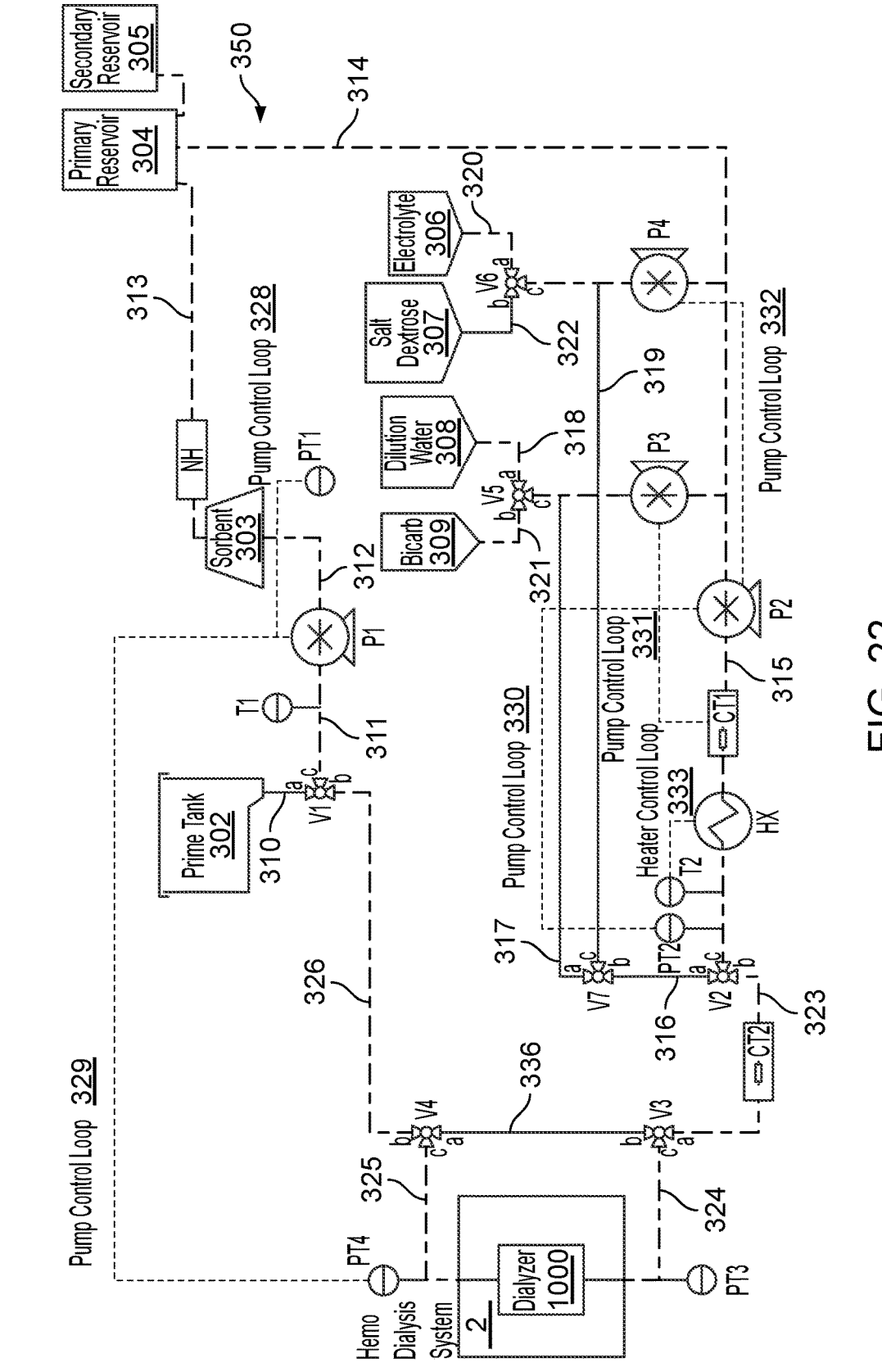
FIG. 22 illustrates a fluid flow path (indicated by highlighted fluid lines) of a treatment stage of the fluid conditioning cycle carried out via the fluid circuit of FIG. 16.

FIG. 22 illustrates operation of the fluid conditioning system 100 during the treatment stage, in which bicarbonate, salt, and dextrose are added to the water in the fluid circuit 350 to produce dialysate. The treatment stage includes a first phase in which bicarbonate solution is used to regulate a conductivity of the dialysate and a second phase in which dilution water is used to regulate a conductivity of the dialysate. Pumps P1, P2 pump dialysate at a flow rate in a range of about 200 mL/min to about 600 m/min. The set point temperature of heat exchanger HX is maintained at a physiologically acceptable temperature in an acceptable range of about 35° C. to about 39° C. (e.g., about 37° C.), as specifically selected by a user of the fluid conditioning system 100 to suit patient comfort. At any point during the treatment stage, if the dialysate fluid temperature measured at CT2 is outside of a range of about 35° C. to about 42° C., then the fluid conditioning system 100 will enter a bypass mode in which dialysate will flow through fluid line 336 to bypass flow through the hemodialysis system 2 via fluid lines 324, 325. While the fluid conditioning system 100 is operating in the bypass mode, a message will be displayed on the display screen 148 indicating that the fluid temperature is too low or too high. The fluid conditioning system 100 will remain in bypass mode until the fluid temperature stabilizes within the acceptable range.

During the first phase of the treatment stage, port (b) of valve V3 is closed, port (c) of valve V3 is opened to allow pump P2 to pump "fresh" dialysate (e.g., cleaned, conditioned dialysate) through a fluid line 324 and into the hemodialysis system 2, port (a) of valve V4 is closed, and port (c) of valve V4 is opened to allow pump P1 to pump "spent" dialysate (e.g., contaminated dialysate) through a fluid line 325 out of the hemodialysis system 2 and further into a fluid line 326. Accordingly, a bypass fluid line 336 that extends between valves V3, V4 is closed. During the treatment stage, spent dialysate is infused with ultra-filtrate from the patient's blood within the hemodialysis system 1. The ultra-filtrate carries toxic substances, such as urea, all of the small water-soluble uremic toxins, and other toxic substances (e.g., guanidosuccinic acid, methylguanidine, 1-methyladenosine, 1-methylinosine, N2,N2-dimethylguanosine, pseudouridine, arab(in)itol, mannitol, α-N-acetylarginine, orotidine, oxalate, guanidine, erythritol, creatine, orotic acid, phenylacetylglutamine, creatinine, myoinositol, γ-guanidinobutyric acid, β-guanidinopropionic acid, symmetric dimethyl-arginine (SDMA), asymmetric dimethyl-arginine (ADMA), sorbitol, uridine, and xanthosine).

From the fluid line 326, the spent dialysate is pumped through ports (b) and (c) of valve V1, the fluid line 311, pump P1, the fluid line 312, and into the sorbent cartridge 303. Within the sorbent cartridge 303, the toxic substances are removed from (e.g., filtered out of) the spent dialysate to produce "regenerated" dialysate (e.g., cleaned, unconditioned dialysate) that flows out of the sorbent cartridge 303 and into the fluid line 313, past the ammonia sensor NH, and into the primary reservoir 304. In some cases, a volume of the regenerated dialysate within the primary reservoir 304 exceeds a capacity of the primary reservoir 304 and therefore flows through a fluid line 327 into the secondary reservoir 305, which remains in fluid communication with the primary reservoir 304 throughout the treatment stage. Pump P2 pumps regenerated dialysate out of the primary reservoir 304, into the fluid line 314, and into pump P2. While the regenerated dialysate exiting the sorbent cartridge 303 has been stripped of toxic substances that were absorbed from the patient's blood in the hemodialysis system 2, the regenerated dialysate must be further conditioned to meet acceptable physiological properties before being circulated back into the dialyzer 1000 of the hemodialysis system 2 as fresh dialysate.

Accordingly, pump P4 continues to pump the electrolyte solution out of the bag 306 and into the fluid line 320, through ports (a) and (c) of valve V6, into an upper segment of the fluid line 319, through pump P4, and into the fluid line 314 at a flow rate that depends on (e.g., is a fraction of) the flow rate at which pump P2 pumps dialysate. Thus, pumps P2, P4 together form a closed pump control loop 332 that governs the flow rate at which pump P4 pumps the electrolyte solution, which is in a range of about 0.5 mL/min to about 5 mL/min. Furthermore, pump P3 continues to pump either the bicarbonate solution out of the bag 309 or the dilution water out of the bag 308, through port (c) of valve V5, into an upper segment of the fluid line 317, through pump P3, and into the fluid line 314 to further condition the dialysate.

As the dialysate passes through pump P2 and conductivity sensor CT1, the conductivity sensor CT1 detects a conductivity of the dialysate. Based on continuous measurements of the conductivity of the dialysate, either the bicarbonate solution or the dilution water will be continuously selected for addition to the dialysate through port (c) of valve V5, and the flow rate at which pump P3 pumps dialysate will be continuously adjusted to maintain a conductivity of the dialysate within a physiologically acceptable range of 13.5 mS/cm to 14.2 mS/cm. Generally, as a difference between the measured conductivity and an acceptable conductivity increases, the flow rate at which the pump P3 pumps fluid increases. Accordingly, as the difference between the measured conductivity and the acceptable conductivity decreases, the flow rate at which the pump P3 pumps fluid decreases. In this manner, the conductivity meter CT1 and the pump P3 together form a closed pump control loop 331 that regulates a flow rate at which the pump P3 pumps fluid. If the conductivity of the dialysate is too low during the first phase of the treatment stage, then bicarbonate solution is infused into the dialysate to raise the conductivity.

After passing the conductivity sensor CT1, the dialysate flows past the heat exchanger HX and temperature sensor T2. Based on a fluid temperature detected by temperature sensor T2, a power level of the heat exchanger HX will be adjusted to maintain the temperature of the dialysate at the set point temperature of the heat exchanger HX. In this way, temperature sensor T2 and heat exchanger HX form a closed heater control loop 333. The dialysate flows from the fluid line 315 through ports (c) and (b) of valve V2 into the fluid line 323 and past conductivity sensor CT2. As the dialysate passes conductivity sensor CT2, conductivity sensor CT2 performs a second check (e.g., downstream of heat exchanger HX) to detect a conductivity of the dialysate.

If the conductivity of the dialysate is outside of the acceptable range (e.g., either too low or too high), but within a predetermined range (e.g., that is broader than the acceptable range), then a safety system in electrical communication with the conductivity sensor will adjust a flow rate of infusion of the bicarbonate solution or the dilution water to achieve a conductivity within the acceptable range. If the conductivity level of the dialysate is outside of the predetermined physiologically safe range, then, in some implementations, the fluid conditioning system 100 will attempt to restore the safe fluid parameters and continue the treatment. For example, valves V3 and V4 will adjust to direct fluid through the bypass fluid line 336 and close fluid lines 324, 325 until a time at which the conductivity has again stably reached a physiologically safe range, at which time valves V3, V4 will adjust to close the bypass fluid line 336 and direct fluid to and from the hemodialysis system 2 via fluid lines 324, 325. In some implementations, a user may also be instructed to check that fluid levels of the bicarbonate solution and the dilution water are non-zero upon return of the conductivity to a physiologically safe range.

Over time, the sorbent cartridge 303 changes a composition of the regenerated dialysate exiting the sorbent cartridge 303 during the first phase of the treatment stage (e.g., an early, initial phase in which the patient's blood is initially circulated through the hemodialysis system 2). For example, during the first phase of the treatment stage, levels of toxic substances within the spent dialysate are relatively high. The sorbent cartridge 303 converts urea into ammonium and captures the ammonium within one or more filtration layers within the sorbent cartridge 303 to remove the ammonium from the dialysate. While the filtration layers capture the ammonium, the filtration layers release sodium cations and other cations into the dialysate via cation exchange, which increases the conductivity and/or decreases the pH of the regenerated dialysate exiting the sorbent cartridge 303.

Over the course of the first phase of the treatment stage, spent dialysate entering the sorbent cartridge 303 contains fewer toxic substances (e.g., as uremic toxins are removed from the patient's blood), and the sorbent cartridge 303 releases more sodium cations. Therefore, the conductivity of the dialysate exiting the sorbent cartridge 303 gradually increases over time. Once the conductivity of the dialysate reaches a predetermined value in a range of about 13.8 mS/cm to about 14.0 mS/cm, the first phase of the treatment stage in which bicarbonate is used to regulate the conductivity of the dialysate concludes, and the second phase of the treatment stage begins.

During the second (e.g., later, final) phase of the treatment stage, bicarbonate is no longer used to regulate (e.g., increase) the conductivity of the dialysate, and dilution water is the sole substance at valve V5 that is used to regulate (e.g., decrease) the conductivity of the dialysate until the end of the treatment stage (e.g., the end of the second phase). Accordingly, port (b) of valve V5 is closed, while port (a) of valve V5 is opened. If the conductivity of the dialysate is too high during the second phase of the treatment stage, then dilution water is infused into the dialysate to lower the conductivity of the dialysate.

Over the course of the second phase of the treatment stage, an amount of ammonium captured in the sorbent cartridge 303 increases, such that a capacity of the sorbent cartridge 303 to absorb additional ammonium gradually decreases, and a level of ammonia (e.g., generated by the ammonium) within the regenerated dialysate eventually increases, once the capacity of the sorbent to adsorb ammonium is exhausted. The ammonia sensor NH detects the level of ammonia within the regenerated dialysate at a location downstream of the sorbent cartridge 303.

The treatment stage (e.g., including both the first and second phases) typically lasts a duration of about 120 min to about 300 min. For example, 240 minutes (e.g., 4 hours) is a standard duration that typically achieves adequate treatment for the vast majority of patients. Furthermore, most treatment stages will end after four hours without reaching a threshold ammonium concentration of 2 mg/dL (e.g., without ever approaching exhaustion of the filtering capabilities of the sorbent cartridge 303). The fluid conditioning system 100 will sound an audio alert signifying that the treatment completed successfully and that the patient 10 can disconnect himself or herself from the dialyzer 1000. However, if the ammonium level in the dialysate (e.g., as detected by the ammonia sensor NH) indicates that the sorbent cartridge 303 is no longer absorbing enough ammonium from the spent dialysate to maintain the ammonium level at or below an acceptable value of about 2 mg/dL prior to the standard treatment duration, then the treatment stage will conclude prematurely. Such conditions may occur occasionally for larger patients that have very high blood urea nitrogen (BUN) levels.

Once the treatment stage concludes, the fluid circuit 350 can be drained of spent dialysate, and the spent dialysate can be disposed of as waste. In some examples, the bags 306, 307, 308, 309 and the various fluid lines can be manually removed and discarded while still containing dialysate. In some examples, the patient 10 may disconnect from the hemodialysis system 2 and drain the fluid lines 323, 326 to a waste receptacle to empty the various components of the fluid conditioning system 100. In some examples, the fluid conditioning system 100 may be operated to run either or both of pumps P1, P2 in a forward direction or a reverse direction to drain any of the bags 306, 307, 308, 309, the sorbent cartridge 303, the prime tank 302, the primary reservoir 304, and the secondary reservoir 305. In some examples, the fluid conditioning system 100 may be operated to run pumps P4 and P3 in a forward direction to drain the bags 306, 307 and 308, 309. In some examples, such operation of pumps P4, P3 may be carried out based on readings at conductivity meter CT1. For example, upon detection of a sufficiently low threshold conductivity, the electrolyte bag 306 may be assumed to have been emptied, such that a next bag or fluid line can be drained.

Throughout the fluid conditioning cycle, pressure transducers PT1, PT2, PT3, PT4 detect fluid pressures to regulate pump flow rates. For example, during all stages (e.g., the priming, infusion, and treatment stages) of the fluid conditioning cycle, pressure transducer PT1 forms a closed pump control loop 328 with pump P1 by detecting a fluid pressure of the dialysate within the fluid line 312 (e.g., located downstream of pump P1) and providing a feedback signal to pump P1 indicative of the fluid pressure. Based on the fluid pressure of the dialysate, an angular speed (e.g., an RPM level) of pump P1 is adjusted to maintain the flow rate within a desired range. During the treatment stage of the fluid conditioning cycle, pressure transducer PT4 forms an additional closed pump control loop 329 with pump P1 by detecting a fluid pressure of the dialysate exiting the hemodialysis system 2 (e.g., upstream of pump P1) and providing a forward signal to pump P1 indicative of the fluid pressure. Based on the fluid pressure of the dialysate, the angular speed of pump P1 is adjusted to closely match the flow rate at pump P1 with that of the dialysate exiting the hemodialysis system 2. Accordingly, the fluid pressure of the dialysate within the fluid line 312 (e.g., downstream of pump P1) is at least in part affected by the fluid pressure of the dialysate exiting the hemodialysis system 2 (e.g., upstream of pump P1).

Similarly, during all stages (e.g., the priming, infusion, and treatment stages) of the fluid conditioning cycle, pressure transducer PT2 forms a closed pump control loop 330 with pump P2 by detecting a fluid pressure of the dialysate within the fluid line 315 (e.g., located downstream of pump P2) and providing a feedback signal to pump P2 indicative of the fluid pressure. Based on the fluid pressure of the dialysate, an angular speed of pump P2 is adjusted to maintain the flow rate within a desired range. During the treatment stage of the fluid conditioning cycle, the flow rate at which pump P3 pumps fluid is regulated by a feedback signal from conductivity meter CT1 to form the pump control loop 331, and the flow rate at which pump P4 pumps the electrolyte solution is regulated by a feedback signal from pump P2 to form the pump control loop 332, as discussed above.

During all stages of the fluid conditioning cycle, pressure transducers PT3 and PT4 detect operation of the dialyzer 1000. If measurements at pressure transducers PT3 and PT4 indicate that there is no fluid flow through the dialyzer 1000, then the fluid conditioning system 100 will enter the bypass mode to flow dialysate through fluid line 336 and to avoid delivering dialysate to the hemodialysis system 1 via fluid lines 324, 325.

Figure 49:
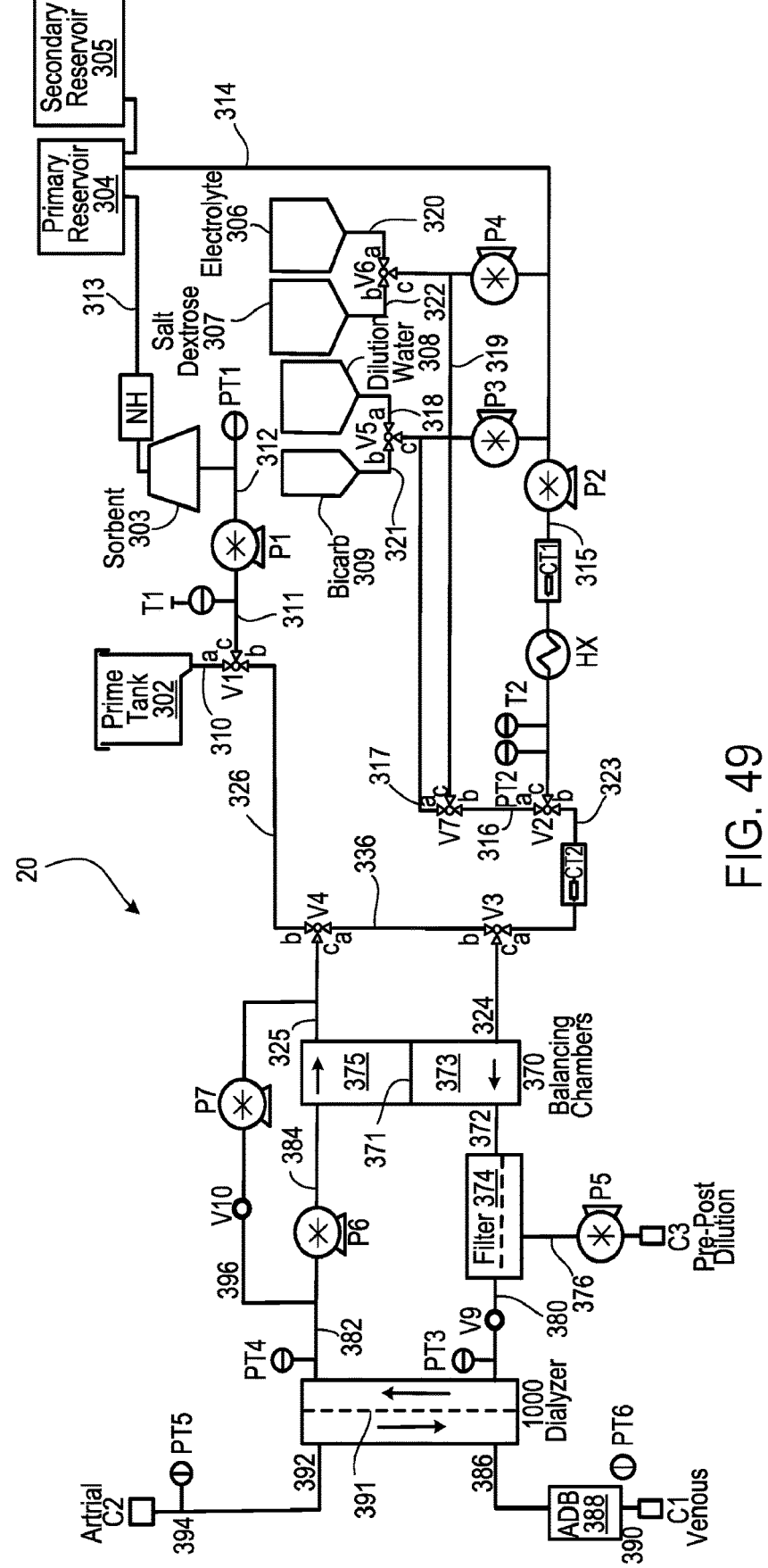
FIG. 49 is an operational diagram of a system including a hemodialysis machine having an integrated fluid conditioning system similar to the fluid conditioning system of FIG. 1 such that the hemodialysis machine is capable of carrying out a fluid conditioning cycle and a hemodialysis treatment.

While the fluid conditioning system 100 has been described as a standalone unit that can be connected to a hemodialysis machine, in some embodiments, the components and functionality of the fluid conditioning system 100 are incorporated into the hemodialysis system and the functionality of the dialysis system are included in a single system. Such a hemodialysis system 20 is shown in FIG. 49. FIG. 49 provides an operational diagram of the hemodialysis system 20. Much of this hemodialysis system 20 includes the same components and works in the same way as the fluid conditioning system 100 discussed above. We will focus on the portions of the hemodialysis system 20 that differ from the fluid conditioning system 100.

Referring to FIG. 49, during hemodialysis, the warm dialysate entering port (a) of V3 is drawn through port (b) of valve V3 and into a balancing device 370. The balancing device 370 is divided by a flexible membrane 371 into a first chamber half 373 and a second chamber half 375. As fluid flows into the first chamber half 373, fluid is forced out of the second chamber half 375, and vice versa. For example, as fresh dialysate flows into first chamber half 373 of the balancing device 370, spent dialysate is forced to flow out of the second chamber half 375 of the balancing device 370 towards the functionality of the fluid conditioning system 300. In contrast, as spent dialysate flows into the second chamber half 375 of the balancing device 370, fresh dialysate is forced out of first chamber half 373 of balancing device 370 towards the dialyzer 1000. This balancing device construction and alternating flow of fresh and spent dialysate helps ensure that the volume of fresh dialysate entering the dialysate circuit is equal to the volume of spent dialysate exiting the dialysate circuit, when desired, during treatment.

During hemodialysis, fresh dialysate passing through the first chamber half 373 of the balancing device 370 is directed to the dialyzer 1000. After exiting the balancing device 370 the fresh dialysate can flow through a filter 374 to further filter the dialysate to generate substitution fluid. As depicted in FIG. 49, a substitution pump P5 is provided along the substitution fluid line 376 to pump the substitution fluid through the substitution fluid line 376 and into a pre/post dilution port C3 located along the blood line set. For example, balancing device 370 can be connected to the substitute port of the dialyzer 1000.

When the substitution pump P5 is not running, all the fresh dialysate passes through the filter 374 and flows along a dialysate inlet line 380 towards the dialyzer 1000. Before entering the dialyzer 1000, the fresh dialysate flows through a pressure sensor PT3 positioned along the dialysate inlet line 380. The pressure sensor PT3 is configured to measure the pressure of the fluid entering the dialyzer 1000. Any of various different types of pressure sensors capable of measuring the pressure of the substitution fluid entering the dialyzer 1000 can be used, such as ultrasonic sensors, piezoresistive strain gauges, capacitive sensors, electromagnetic sensors, or piezoelectric sensors.

After flowing through the dialyzer 1000, spent dialysate exits the dialyzer 1000 through the dialysate outlet line 382. A pressure sensor PT4 located along the dialysate outlet line 382 is adapted to measure the pressure of the spent substitution fluid exiting the dialyzer 1000.

A dialysate flow pump P6 is configured to pump the spent dialysate from the dialyzer 1000 to the second chamber half 458 of the balancing device 370.

As the second chamber half 375 of the balancing device 370 fills with the spent substitution fluid, fresh dialysate within the first chamber half 373 of the balancing device 370 is expelled towards the dialyzer 1000. Subsequently, as the first chamber half 373 of the balancing device 370 is refilled with fresh dialysate, the spent substitution fluid is forced out the second chamber half 375 of the balancing device 370 along fluid line 325 to be recycled and processed by the functionality of the built-in fluid conditioning system 100.

Additionally, line 396 can be used to bypass the balancing chamber 370. When valve V10 is open while simultaneously operating the flow pump P7, this causes an increase in vacuum pressure within the dialysate outlet line 382, and thus creates an increase in vacuum pressure within the dialyzer 1000. As a result of the increased vacuum pressure, additional fluid is pulled from the blood circuit into the dialysate circuit across the semi-permeable structure 391 (e.g., semi-permeable membrane or semi-permeable micro-fibers) of the dialyzer 1000. Thus, pump P7 can be operated to remove excess fluid from the patient. Such removal of excess fluid is referred to as ultrafiltration.

During hemodialysis, the patient 10 is connected to hemodialysis system 2 with the venous port C1 and the arterial port C2. Pressure transducers PT5 and PT6 measure the pressure of the blood in the arterial line 394 and venous line 390, respectively. The venous line 390 can further include a method for removing air in the blood 388.

Other embodiments are also possible.

For example, while embodiments discussed above include a hemodialysis system connected to or including a fluid conditioning system, other types of blood treatment systems can be used. Examples of such blood treatment systems include extracorporeal blood treatment systems, such as hemofiltration (HF) systems, hemodiafiltration (HDF) systems, and ultrafiltration (UF) systems, as well as peritoneal dialysis (PD) systems.

While the dialyzer 1000 has been described as a single-use device, in some embodiments, the dialyzer may be reused two or more times for a given patient.

While the hemodialysis system 20 has been shown using one balance device 370, two balance devices can be used and alternatively operated to generate a continuous flow of fresh and spend dialysate.

While the fluid conditioning system 100 has been shown to cooperate with the dialyzer 1000 of the hemodialysis system 1 to form the fluid circuit 350, in some cases the fluid conditioning system can cooperate with the hemodialysis machine 2000.

Other embodiments of the fluid conditioning system 100 will now be described.

Figure 26:
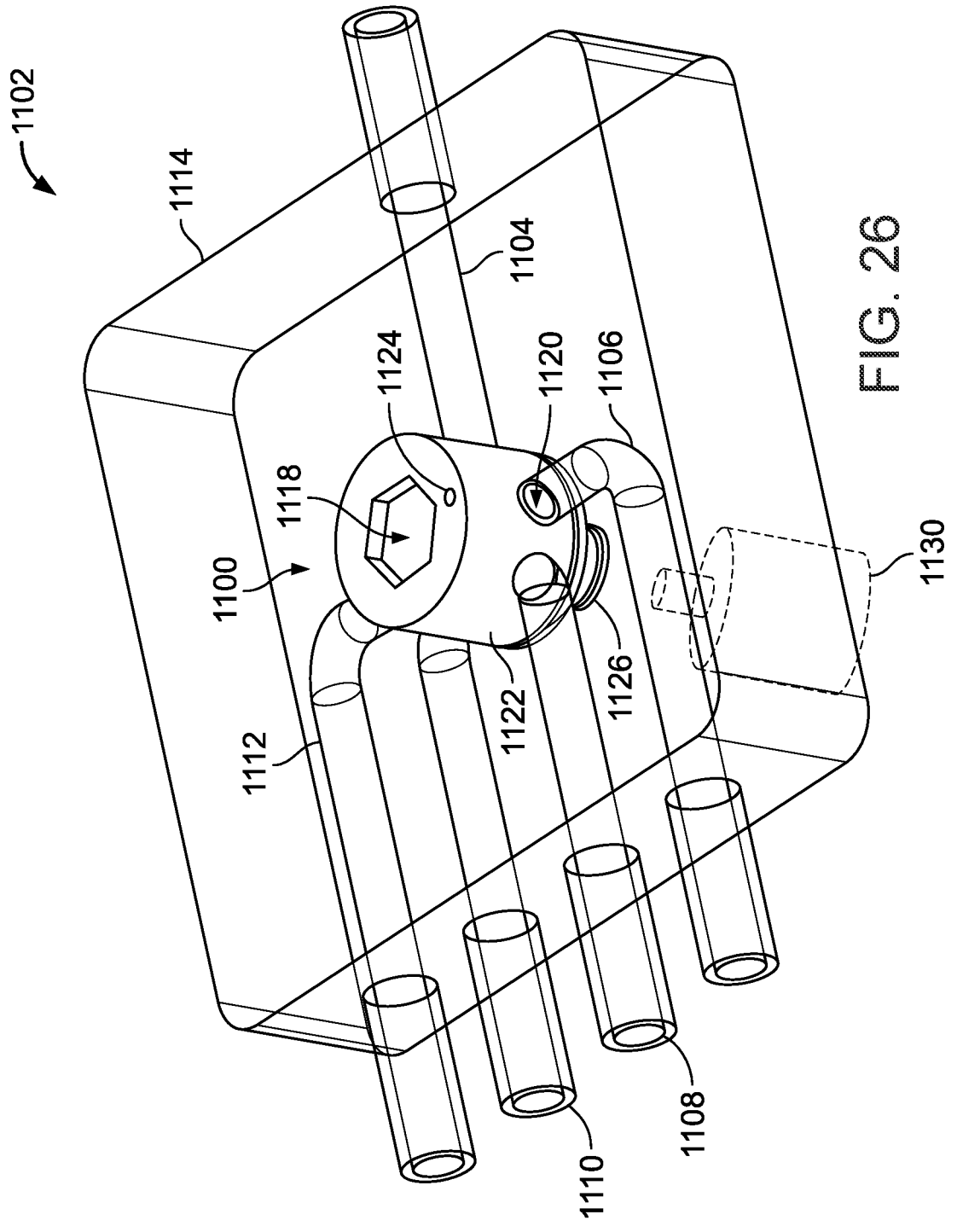
FIG. 26 is a perspective view of a portion of a dialysis fluid cassette including a rotary valve with a recessed actuation feature.

For example, FIG. 26 illustrates a rotary valve 1100 that can service multiple fluid pathways of a fluid cassette 1102 within a dialysis system. In some embodiments, the rotary valve 1100 may be an embodiment of a valve 202 of the fluid conditioning system 100, and such dialysis system may be embodied as the fluid conditioning system 100. In the example embodiment of FIG. 26, the cassette 1102 includes an inlet fluid line 1104, multiple outlet fluid lines 1106, 1108, 1110, 1112, and a housing 1114 that carries the fluid lines 1104, 1106, 1108, 1110, 1112, among other components that are not shown. The rotary valve 1100 can be rotated (e.g., spun about its central axis) by an actuator to allow fluid to flow from the inlet fluid line 1104 to a selected one of the outlet fluid lines 1106, 1108, 1110, 1112, while preventing fluid from flowing from the inlet fluid line 1104 to the other of the outlet fluid lines 1106, 1108, 1110, 1112.

The rotary valve 1100 has a generally cylindrical shape and defines a recessed profile 1118 (e.g., an actuation feature) by which the actuator can engage the rotary valve 1100 to rotate the rotary valve 1100. The rotary valve 1100 also defines an internal fluid pathway 1120 that is designed to align simultaneously with the inlet fluid line 1104 at an entry end and a selected one of the outlet fluid lines 1106,

1108, 1110, 1112 at an exit end to allow fluid to flow to the selected outlet fluid line, such that the other of the outlet fluid lines 1106, 1108, 1110, 1112 are closed (e.g., blocked off) by a sidewall 1122 of the rotary valve 1100. The rotary valve 1100 further defines a visual indicator 1124 that aligns with the selected one of the outlet fluid lines 1106, 1108, 1110, 1112 to indicate that the selected outlet fluid line 1106, 1108, 1110, 1112 is open. The visual indicator 1124 is formed as a circular recess, but in general may be provided as a variety of symbols, marks, or surface profiles.

The recessed profile 1118 is provided as a polygonal (e.g., hexagonal) recess that is sized to receive a complimentary polygonal actuator, such that rotational movement of the actuator applies a force to the recessed profile 1118 to effect a corresponding rotational movement of the rotary valve 1100. The rotary valve 1100 is rotated to an extent that is sufficient to align the exit end of the internal fluid pathway 1120 with a selected one of the outlet fluid lines 1106, 1108, 1110, 1112.

In some embodiments, the rotary valve 1100 includes a spring 1126 located along a lower end by which the rotary valve 1100 can be moved up or down by a solenoid 1130 (e.g., or another type of actuator) to enable or disable the rotary valve 1100. For example, in a compressed configuration of the spring 1126, a vertical position (e.g., a "down" position) of the internal fluid pathway 1120 of the rotary valve 1100 may align with a vertical position of the fluid lines 1104, 1106, 1108, 1110, 1112, such that the rotary valve 1100 is enabled for operation, as shown in FIG. 26. In contrast, in an extended configuration of the spring 1126, a vertical position (e.g., an "up" position) of the internal fluid pathway 1120 of the rotary valve 1100 may be offset from a vertical position of the fluid lines 1104, 1106, 1108, 1110, 1112, such that an operational capability of the rotary valve 1100 is disabled. Example cases for which the rotary valve 1100 may be disabled include a loss of power to the dialysis system, among other cases.

Owing to a capability of a single rotary valve 1100 to service multiple fluid pathways of a dialysis fluid cassette, a design of the dialysis fluid cassette can be simplified as compared to conventional dialysis fluid cassettes that require a dedicated valve for each fluid pathway. Accordingly, a cassette including the rotary valve 1100 can include a relatively reduced total number of valves, which can result in a reduced total heat generation within a dialysis system, a reduced cost of the dialysis system, a reduced size of a footprint of the cassette, and a reduced amount of hardware electronics within the dialysis system.

Figures 27, 28:
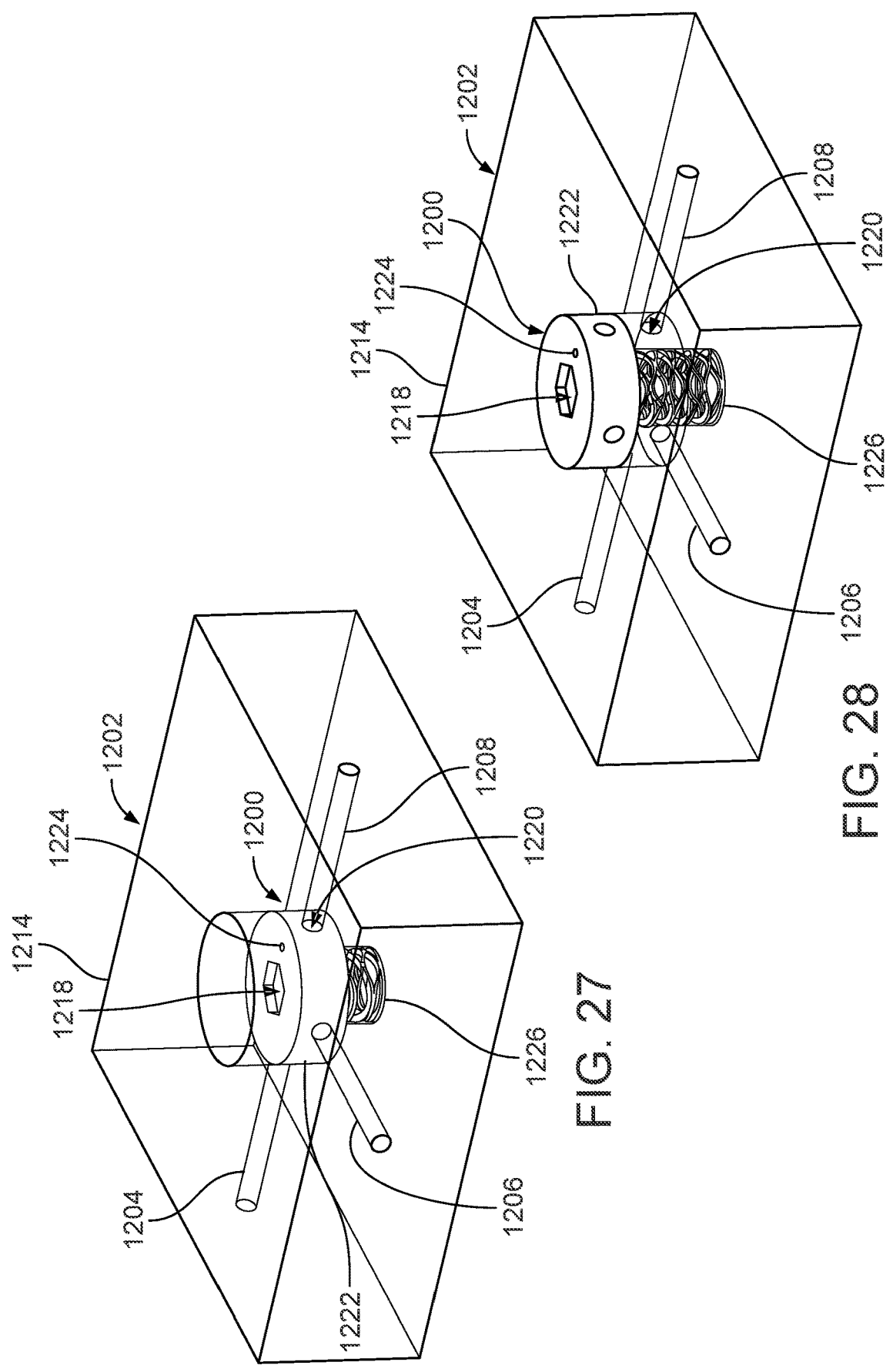
FIG. 27 is a perspective view of a portion of a dialysis fluid cassette including a rotary valve with a recessed actuation feature, with the rotary valve in an enabled configuration.
FIG. 28 is a perspective view of the portion of the dialysis fluid cassette of FIG. 27, with the rotary valve in a disabled configuration.

FIGS. 27 and 28 illustrate a rotary valve 1200 that can service multiple fluid pathways of a fluid cassette 1202 within a dialysis system. In some embodiments, the rotary valve 1200 may be an embodiment of a valve 202 of the fluid conditioning system 100, and such dialysis system may be embodied as the fluid conditioning system 100. In the example embodiment of FIGS. 27 and 28, the cassette 1202 includes an inlet fluid line 1204, two outlet fluid lines 1206, 1208 and a housing 1214 that carries the fluid lines 1204, 1206, 1208, among other components that are not shown. The rotary valve 1200 is similar in construction and function to the rotary valve 1100, except that the rotary valve 1200 is designed to interface with two fluid outlet lines 1206, 1208, instead of five fluid outline lines. Accordingly, the rotary valve 1200 can be acted upon by the solenoid 1130 to be enabled or disabled and includes an internal fluid pathway 1220, a sidewall 1222, a recessed profile 1218, and a visual indicator 1224 that are substantially similar in construction and function to like features of the rotary valve 1100, as described above.

For example, FIG. 27 illustrates the spring 1226 in a compressed configuration for which a vertical position (e.g., a "down" position) of the internal fluid pathway 1220 of the rotary valve 1200 aligns with a vertical position of the fluid lines 1204, 1206, 1208, such that the rotary valve 1200 is enabled for operation. In contrast, FIG. 28 illustrates an extended configuration of the spring 1226 for which a vertical position (e.g., an "up" position) of the internal fluid pathway 1220 of the rotary valve 1200 is offset from a vertical position of the fluid lines 1204, 1206, 1208, such that an operational capability of the rotary valve 1200 is disabled.

Figure 29:
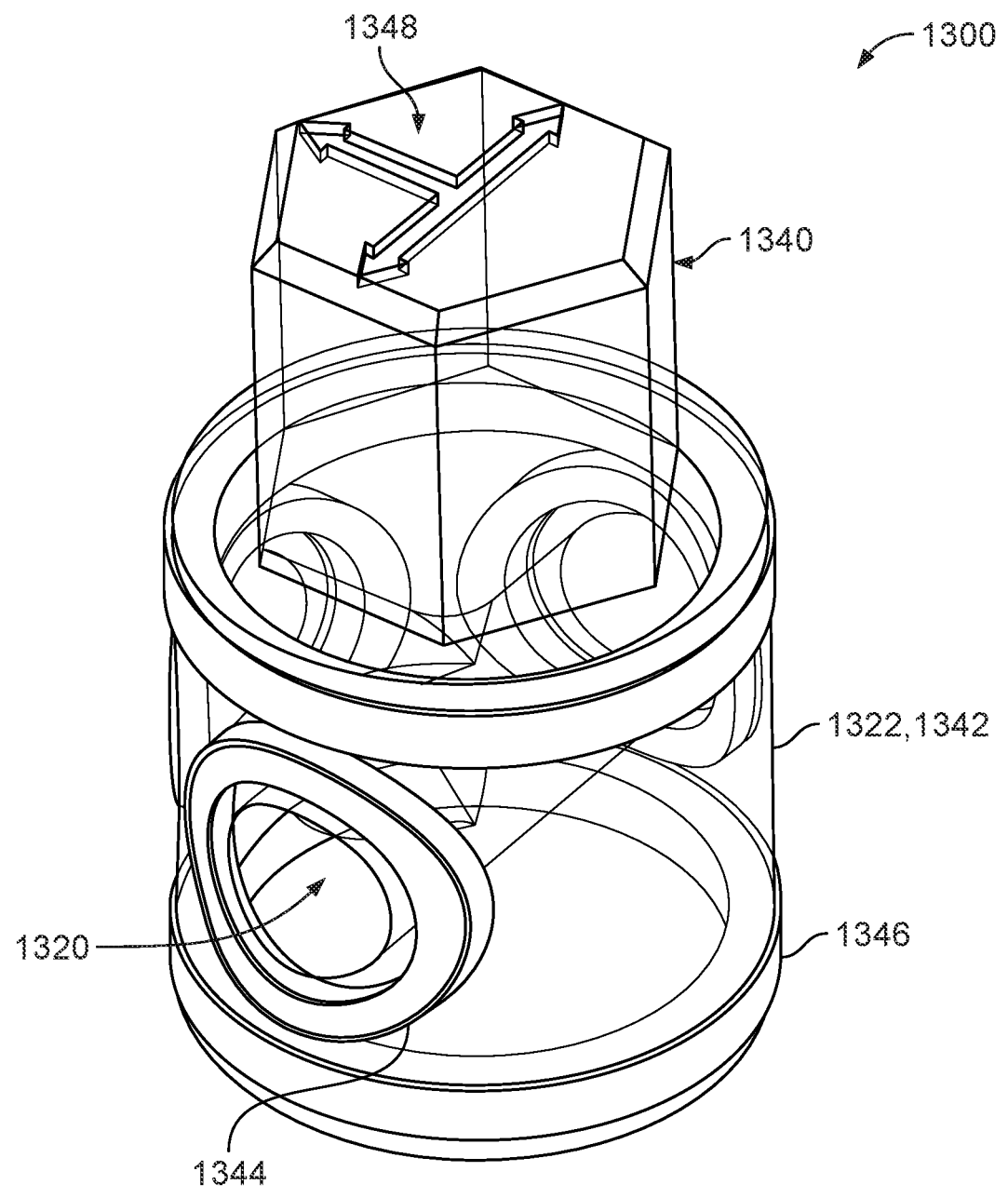
FIG. 29 is a perspective view of a rotary valve with a protruding actuation feature.

While the rotary valves 1100, 1200 have been described and illustrated as including a recessed profile 1118, 1218, in some embodiments, a rotary valve that is similar in function to either of the rotary valves 1100, 1200 may include a protruding actuation feature. For example, FIG. 29 illustrates a rotary valve 1300 that includes a valve stem 1340 as an actuation feature. As discussed above with respect to the rotary valves 1100, 1200, the rotary valve 1300 can be provided as part of a fluid cassette of a dialysis system. In some embodiments, the rotary valve 1300 may be an embodiment of a valve 202 of the fluid conditioning system 100, and such dialysis system may be embodied as the fluid conditioning system 100. The rotary valve 1300 further includes a valve body 1342 that defines an internal fluid pathway 1320 (e.g., a three-way fluid pathway).

The valve stem 1340 has a polygonal (e.g., hexagonal) exterior profile that can be engaged with (e.g., surrounded and/or grasped by) a complimentary profile of an actuator such that rotational movement of the actuator applies a force to the valve stem 1340 to effect a corresponding rotational movement of the rotary valve 1300. The rotary valve 1300 can be rotated to an extent that is sufficient to align ends of the internal fluid pathway 1320 with selected fluid lines of the cassette to permit flow into the fluid lines or to close (e.g., block off) selected fluid lines of a cassette (e.g., a long a sidewall 1322 of the valve body 1342) to prevent flow into the fluid lines. The valve stem 1340 defines an indicator 1348 (e.g., a recessed feature) that visually indicates branch directions of the internal fluid pathway 1320.

The valve body 1342 further includes multiple sealing rings 1344 positioned respectively about open ends of the internal fluid pathway 1320 and two oppositely disposed sealing rings 1346 arranged circumferentially about upper and lower ends of the valve body 1342. The sealing rings 1344 are designed to hermetically seal the rotary valve 1300 to fluid lines of a cassette. Because the sealing rings 1344 follow a curvature of both the sidewall 1322 of the valve body 1342 and a circumference of the fluid lines, a shape of the sealing rings 1344 exhibits a compound curve. The sealing rings 1346 are designed to hermetically seal the rotary valve 1300 to a housing of the cassette and thus have a substantially circular curvature. Placement of the sealing rings 1346 along both upper and lower ends of the valve body 1342 maintains a balanced position and a balanced orientation of the rotary valve 1300 within a cassette.

The sealing rings 1344, 1346 have a thin, rectangular cross-sectional shape (e.g., similar to that of a washer), as opposed to a circular cross-sectional shape exhibited by conventional o-rings, which would not provide adequate sealing of the rotary valve 1300. The sealing rings 1344, 1346 are elastomeric components that are typically rated to withstand a fluid pressure of about to about 50 psi. The sealing rings 1344, 1346 are typically manufactured via over-molding.

Figure 30:
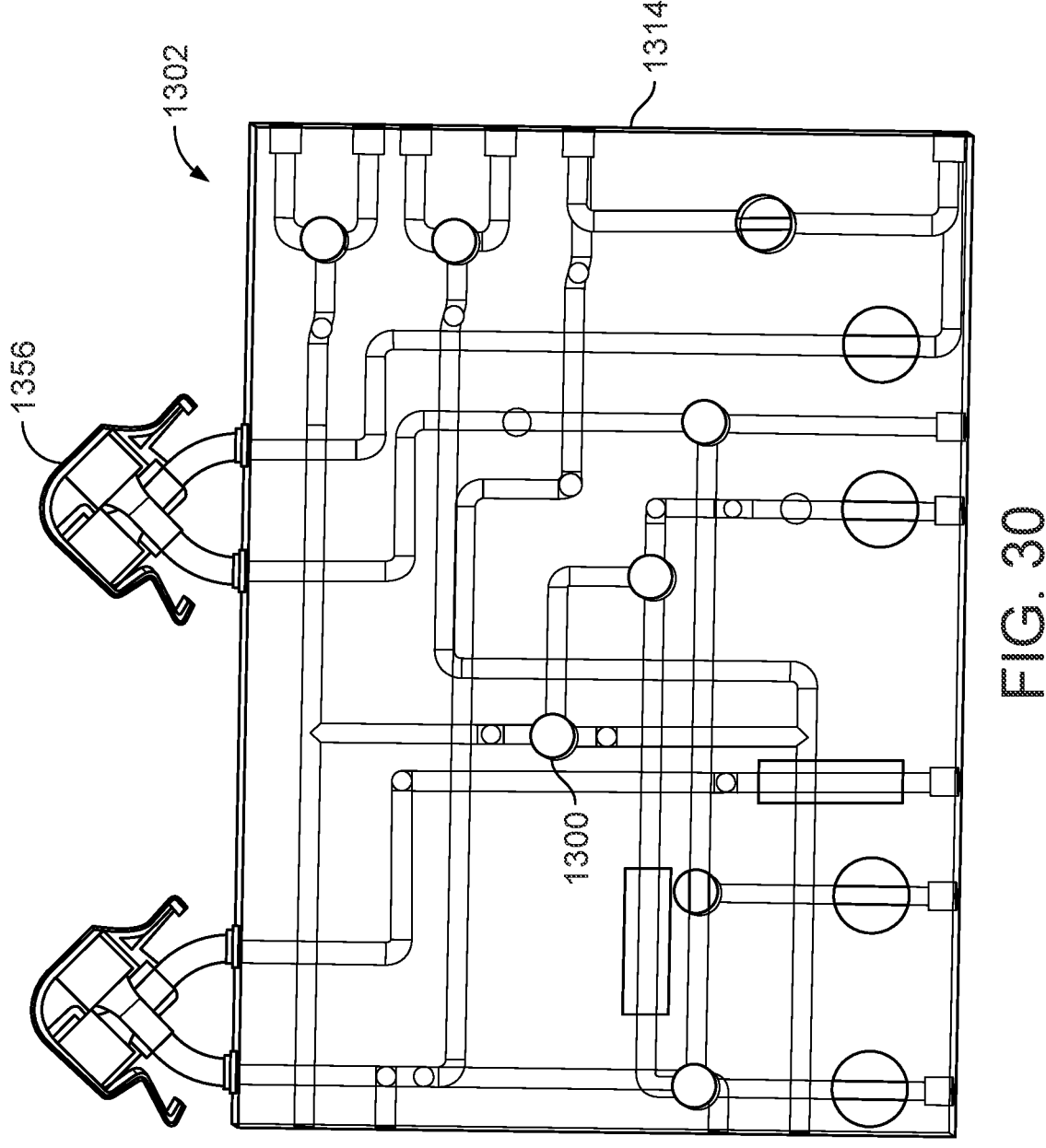
FIG. 30 is a top view of a dialysis fluid cassette including multiple rotary valves of FIG. 29 positioned along multiple fluid lines.
Figure 31:
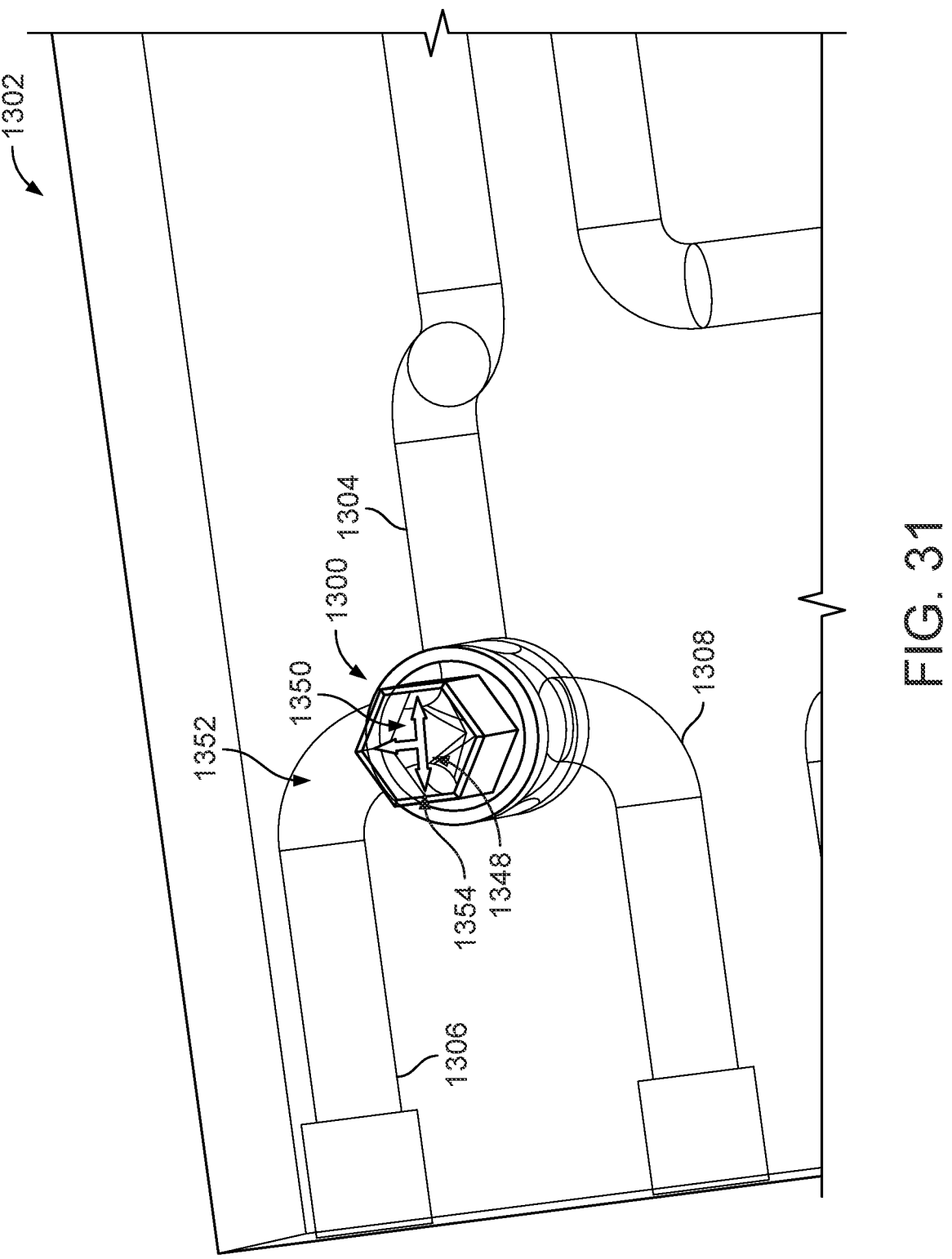
FIG. 31 is an enlarged perspective view of a portion of the dialysis fluid cassette of FIG. 5.

Referring to FIGS. 30 and 31, an example cassette 1302 includes seven rotary valves 1300 that are located along various fluid paths defined by the cassette 1302 and two fluid hubs 1356 to which tubing can be attached and routed to respective pumps of the dialysis system. In some embodiments, the cassette 1302 may be an embodiment of the fluid cassette 102 of the fluid conditioning system 100. The valve bodies 1342 are disposed within a perimeter of a housing 1314 of the cassette 1302, while the valve stems 1340 extend away from (e.g., above) the cassette 1302 for exposure to an actuator (not shown). Referring particularly to FIG. 31, the rotary valve 1300 is arranged at an intersection of an inlet fluid line 1304 and two outlet fluid lines 1306, 1308. First and second branches 1350, 1352 of the internal fluid pathway 1320 are aligned respectively with the inlet fluid line 1304 and the outlet fluid line 1306 such that fluid can flow from the inlet fluid line 1304 into the outlet fluid line 1306. A third branch 1354 of the internal fluid pathway 1320 is offset from all fluid lines, such that the sidewall 1322 of the valve body 1342 blocks the fluid outlet line 1308 to prevent fluid from flowing into the fluid outlet line 1308.

In some implementations, results that can be achieved by actuating one or more of the rotary valves 1100, 1200, 1300 within a dialysis fluid cassette include providing water to dry-chemistry bags (e.g., the bags 306, 307, 309 of the fluid conditioning system 100) for mixing, providing a flow of dialysate to a patient 10, opening a flow path to a sorbent cartridge (e.g., the sorbent cartridge 303 of the fluid conditioning system 100), or closing a flow path for heating.

Furthermore, while the rotary valves 1100, 1200, 1300 and the cassettes 1102, 1202, 1302 have been described and illustrated as including certain arrangements and configurations, in some embodiments, rotary valves and cassettes that are otherwise similar in structure and function to the rotary valves 1100, 1200, 1300 or the cassettes 1102, 1202, 1302 may include different arrangements or configurations.

For example, while the recessed profiles 1118, 1218 and the valve stem 1340 have been described and illustrated as having hexagonal profiles, in some embodiments, rotary valves that are otherwise similar in structure and function to the rotary valves 1100, 1200, 1300 may include actuation features that have different profiles, such as other polygonal profiles, non-polygonal profiles, other symmetric profiles, or asymmetric profiles. For example, an actuation feature with an asymmetric profile may ensure a correctly oriented mating between an actuator and a rotary valve.

While the cassette 1302 has been described and illustrated as including seven three-way rotary valves 1300, in some embodiments, a cassette that is otherwise similar in structure and function to the cassette 1302 may include a different number of rotary valves 1300 or one or more two-way rotary valves.

While the rotary valves 1100, 1200, 1300 have been described for use with the fluid conditioning system 100 as part of a larger hemodialysis system, in some embodiments, the rotary valves 1100, 1200, 1300 can be implemented with other types of medical systems, including PD systems, hemofiltration systems, hemodiafiltration systems, apheresis systems, dialysate generation systems, and water purification systems, among others. For example, a PD system may be operated such that certain rotary valves 1100, 1200, 1300 are operated (e.g., rotated and enabled or disabled) to allow dialysate to be pumped from a dialysate supply bag to a heater bag. After the dialysate in the heater bag is warmed, certain valves rotary valves 1100, 1200, 1300 can be operated for pumping the warmed dialysate to the patient 10. The rotary valves 1100, 1200, 1300 may then be operated to again allow for dialysate to be pumped to the heater bag where the dialysate is warmed. After the dialysate dwells within the patient's peritoneal cavity for a desired period of time, the rotary valves 1100, 1200, 1300 may be operated in a way to allow the spent dialysate to be pumped from the patient's peritoneal cavity to a drain. Such a process can be repeated several times during a treatment.

Figures 32, 33:
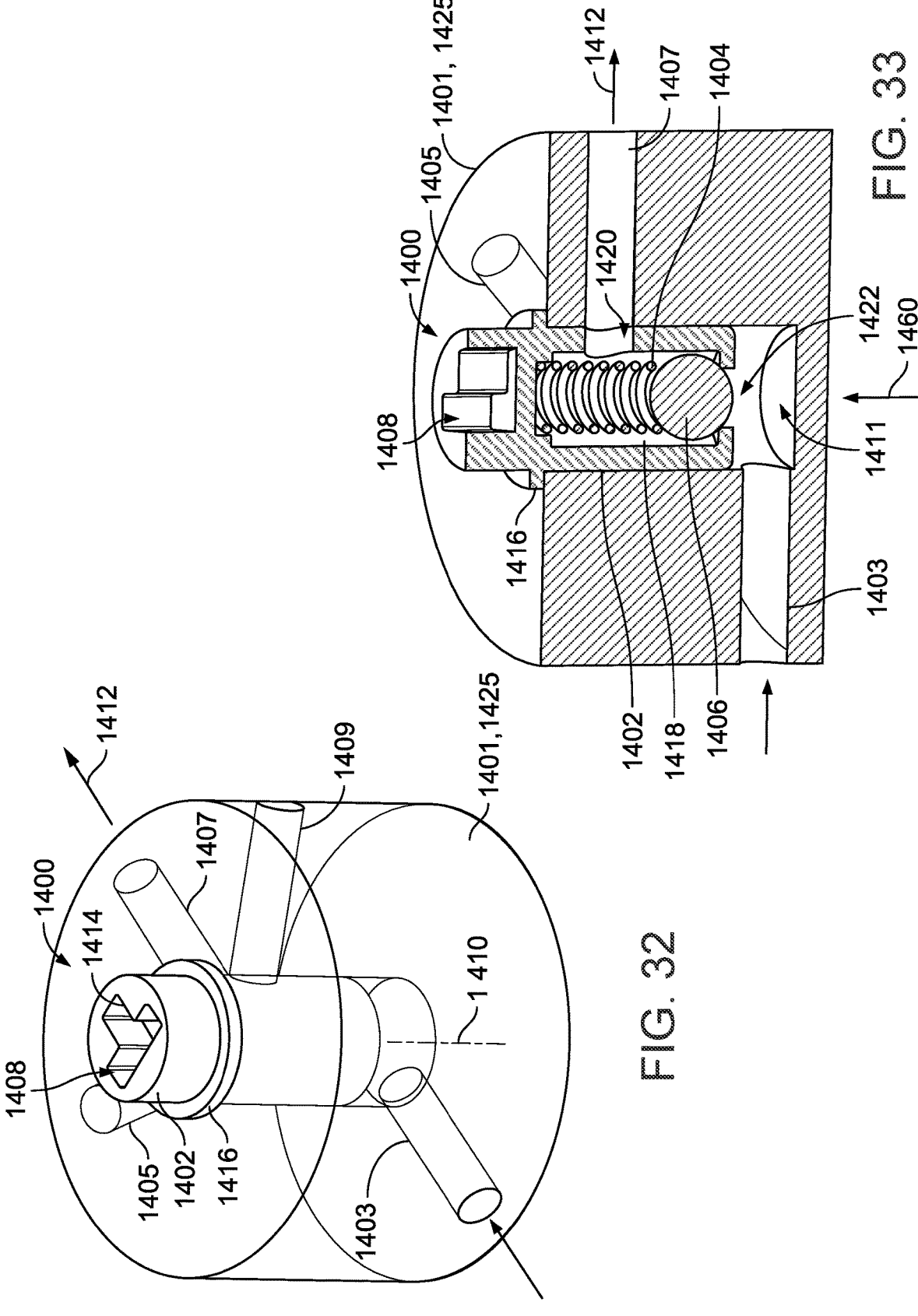
FIG. 32 is a perspective view of a rotary valve with a check valve configuration.
FIG. 33 is a cross-sectional perspective view of the rotary valve of FIG. 32.
Figures 34A, 34B, 34C, 34D:
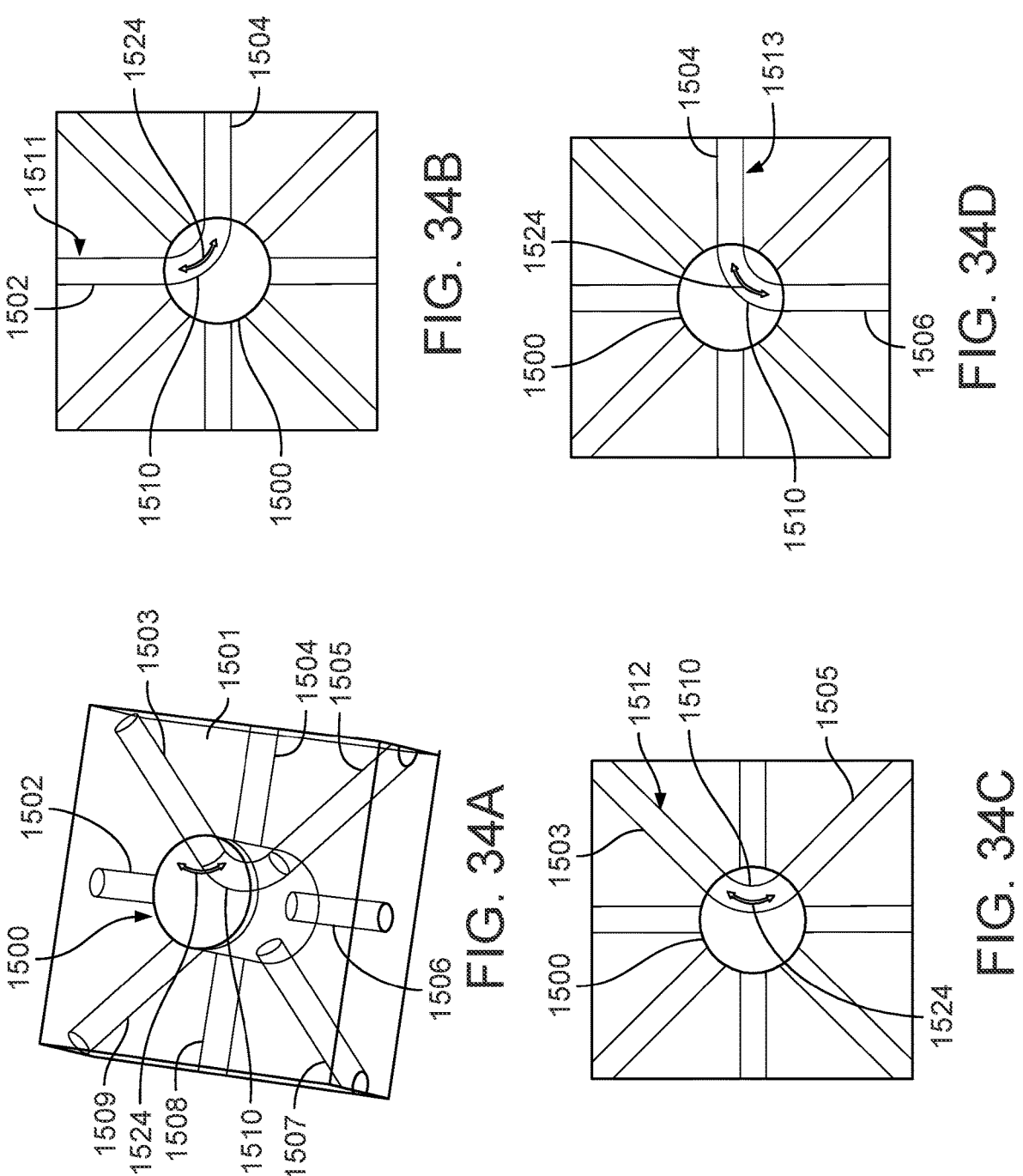
FIG. 34A is a perspective view of a rotary valve that enables a single fluid pathway of multiple sequential fluid pathways.
FIGS. 34B-34I are top views of the rotary valve of FIG. 34A in rotational positions that enables one of the multiple sequential fluid pathways of FIG. 34A.
Figures 34E, 34F, 34G, 34H, 34I:
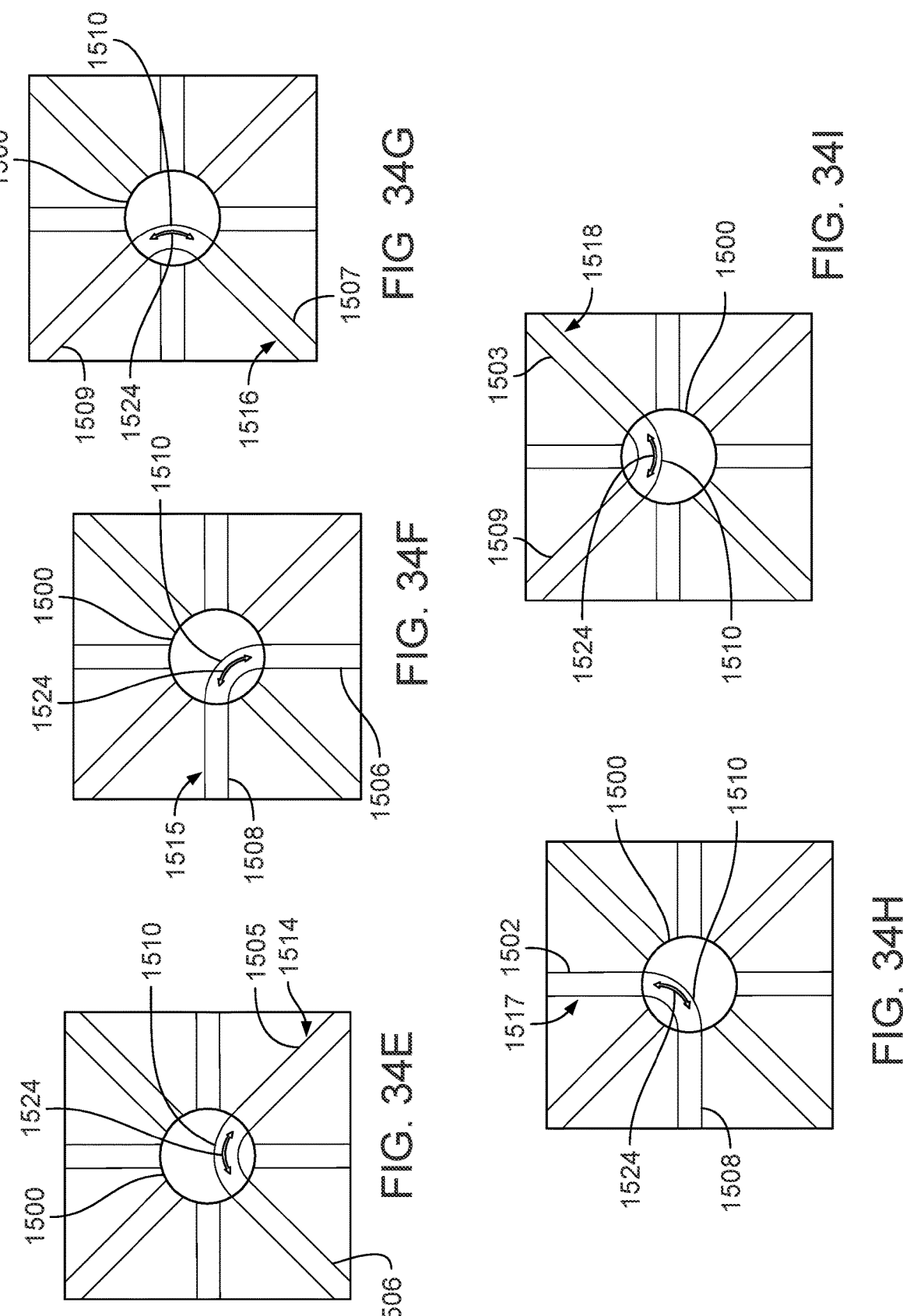

In some embodiments, a rotary valve designed to service multiple fluid pathways of a fluid cassette within a dialysis system includes a check valve configuration. For example, FIGS. 32 and 33 illustrate such a rotary valve 1400 installed in a fluid cassette 1401. In some embodiments, the rotary valve 1400 may be an embodiment of a valve 202 of the fluid conditioning system 100, and the fluid cassette 1401 may be an embodiment of the fluid cassette 102 of the fluid conditioning system 100. The cassette 1401 includes an inlet fluid line 1403, multiple outlet fluid lines 1405, 1407, 1409, and a housing 1425 that carries the fluid lines 1403, 1405, 1407, 1409, among other components that are not shown. As discussed above with respect to the rotary valve 1100, the rotary valve 1400 can be rotated by an actuator to allow fluid to flow from the inlet fluid line 1403 to a selected one of the outlet fluid lines 1405, 1407, 1409, while preventing fluid from flowing from the inlet fluid line 403 to the other two of the outlet fluid lines 1405, 1407, 1409.

The rotary valve 1400 includes a valve body 1402, a spring 1404 housed within the valve body 1402, and a ball bearing 1406 housed within the valve body 1402. The valve body 1402 is generally cylindrical in shape and defines a recessed profile 1408 (e.g., an interface) at which the rotary valve 1400 can be engaged by a system actuator (not shown) for rotating the rotary valve 1400 about a central axis 1410 of the valve body 1402. The recessed profile 1408 is formed as a receptacle with a shape that is complimentary to that of the system actuator and that indicates a fluid flow direction 1412 out of the rotary valve 1400. For example, the recessed profile 408 has a "t" shape with a central extension 1414 that can be oriented parallel to any of the outlet fluid lines 1405, 1407, 1409. The valve body 1402 also defines a flange 1416 that seats against the fluid cassette 1401.

The valve body 1402 further defines various features that direct fluid flow through the rotary valve 1400. For example, the valve body 1402 defines an interior pocket 1418 that contains the spring 1404 and the ball bearing 1406, a lateral opening 1420 to the interior pocket 1418, and an axial opening 1422 to the interior pocket 1418. The spring 1404 is biased to an extended configuration that forces the ball bearing 1406 to a position in which the ball bearing 1406 abuts the axial opening 1422 of the interior pocket 1418, as shown in FIG. 33. A diameter of the ball bearing 1406 is larger than a diameter of the axial opening 1422 such that the ball bearing 1406 closes (e.g., fluidically seals) the axial opening 1422 to any fluid flowing towards the axial opening 1422 when the spring 1404 is in the extended configuration. In this manner, the ball bearing 1406 acts as a plug within the interior pocket 1418 that can prevent or permit fluid flow through the axial opening 1422.

For fluid to flow through the rotary valve 1400, fluid must flow from the inlet fluid line 1403, into a fluid receptacle 1411, and towards the axial opening 1422 with a pressure great enough (e.g., a cracking pressure) to push the ball bearing 1406 in an upward direction 1460 from the axial opening 1422 (e.g., thereby compressing the spring 1404) such that the fluid unseats the ball bearing 1406 to allow fluid to flow up into the interior pocket 1418. The diameter of the ball bearing 1406 is smaller than a diameter of the interior pocket 1418 such that fluid can flow up and around the ball bearing 1406 within the interior pocket 1418 and out of the lateral opening 1420. If fluid was to flow from any of the outlet fluid lines 1405, 1407, 1409 and into the interior pocket 1418 through the lateral opening 1420, such fluid would urge the ball bearing 1406 toward the axial opening 1422, thereby seating the ball bearing 1406 in the axial opening 1422 and preventing fluid from flowing out of the interior pocket 1418 through the axial opening 1422. Accordingly, the spring 1404, the ball bearing 1406, and the interior pocket 1418 together form a check valve configuration that allows fluid to flow only in a single bulk direction 1460 along the central axis 1410 of the valve body 1402, which is transverse to the outlet fluid lines 1405, 1407, 1409. For example, while molecules of the fluid can flow in several different directions as the fluid travels around the ball bearing 1406, a bulk direction of the fluid flow is that of the bulk flow direction 1460. The check valve configuration of the rotary valve 1400 typically has a cracking pressure in a range of about 500 Pa to about 10,000 Pa.

The interior pocket 1418 of the valve body 1402 typically has a diameter of about 6.4 mm to about 6.8 mm (e.g., about 6.6 mm). The axial opening 1422 in the interior pocket 1418 typically has a diameter of about 3.9 mm to about 4.3 mm (e.g., about 4.1 mm). The ball bearing 1406 typically has a diameter of about 6.1 mm to about 6.5 mm (e.g., about 6.3 mm). The lateral opening 1420 typically has a diameter of about 3.6 mm to about 4.0 mm (e.g., about 3.8 mm). The valve body 1402 typically has an exterior diameter (e.g., excluding the flange 1416) of about 10.0 mm to about 10.4 mm (e.g., about 10.2 mm) and a total height of about 26.5 mm to about 26.9 mm (e.g., about 26.7 mm). The flange 1416 is typically spaced from an upper end of the valve body 1402 by a distance of about 4.9 mm to about 5.3 mm (e.g., about 5.1 mm).

The valve body 1402, the spring 1404, and the ball bearing 1406 are made of materials that are corrosion resistant, bio-compatible, durable, and suitable for manufacturing. For example, the valve body 1402 is typically made of polyetherimide, the spring 1404 is typically made of stainless steel, and the ball bearing 1406 is typically made of stainless steel. Furthermore, the valve body 1402 and the ball bearing 1406 are typically manufactured respectively via injection molding and grinding/lapping. In some embodiments, the rotary valve 1400 can be used to regulate the fluid pressure in a hemodialysis system to maintain the fluid pressure below a certain cracking pressure. For example, the pressure of dialysate fluid in a dialyzer of a hemodialysis system may be regulated using the rotary valve 1400.

In some embodiments, a rotary valve is designed to service multiple fluid pathways distributed about a circumference of the rotary valve within a fluid cassette of a dialysis system. For example, FIGS. 34A-I illustrate such a rotary valve 1500 installed in a fluid cassette 1501. The rotary valve 1500 can service multiple fluid pathways a fluid cassette 1501 within a dialysis system. In some embodiments, the rotary valve 1500 may be an embodiment of a valve 202 of the fluid conditioning system 100, the fluid cassette 5401 may be an embodiment of the fluid cassette 102 of the fluid conditioning system 100, and such dialysis system may be an embodiment of the fluid conditioning system 100. In the example embodiment of FIGS. 34A-34I, the fluid cassette 1501 includes fluid lines 1502-1509 that are distributed about a circumference of the rotary valve 1500 at an equal spacing, and any of the fluid lines 1502-1509 may serve as an inlet line or an outlet line, depending on a rotational position of the rotary valve 1500.

The rotary valve 1500 has a generally cylindrical shape and defines a recessed profile (e.g., an actuation feature, not shown) along one end of the rotary valve 1500 by which an actuator can engage the rotary valve 1500 to rotate the rotary valve 1500. The rotary valve 1500 also defines an internal fluid conduit 1510 that is designed to align simultaneously with alternating fluid lines 1502-1509 to define any one of eight sequential fluid paths 1511-1518, such that the other, seven remaining fluid pathways 1511-1518 are closed (e.g., blocked off or disabled) by a body of the rotary valve 1500. For example, a radius and a radial position of the internal fluid conduit 1510 are selected such that the internal fluid conduit 1510 can be rotationally positioned (e.g., upon rotation of the rotary valve 1500 at the recessed profile) to align with the fluid lines 1502, 1504 to define the fluid pathway 1511; with the fluid lines 1503, 1505 to define the fluid pathway 1512; with the fluid lines 1504, 1506 to define the fluid pathway 1513, and so on about a circumference of the rotary valve 1500. The rotary valve 1500 further defines a visual indicator 1524 (e.g., illustrated schematically as a curved arrow in FIGS. 34A-34I) that aligns with the selected fluid lines 1502-1509 to indicate that the selected fluid pathway 1511-1518 is activated (e.g., open for fluid flow). In some embodiments, driving the rotary valve 1500 with a motor and an absolute encoder with a unique connection interface for coupling with the rotary valve 1500 can allow selection from six different fluid pathways (e.g., with single-direction fluid flow) or from twelve different fluid pathways (e.g., with bi-directional fluid flow) within a dialysis system.

Figures 35A, 35B, 35C:
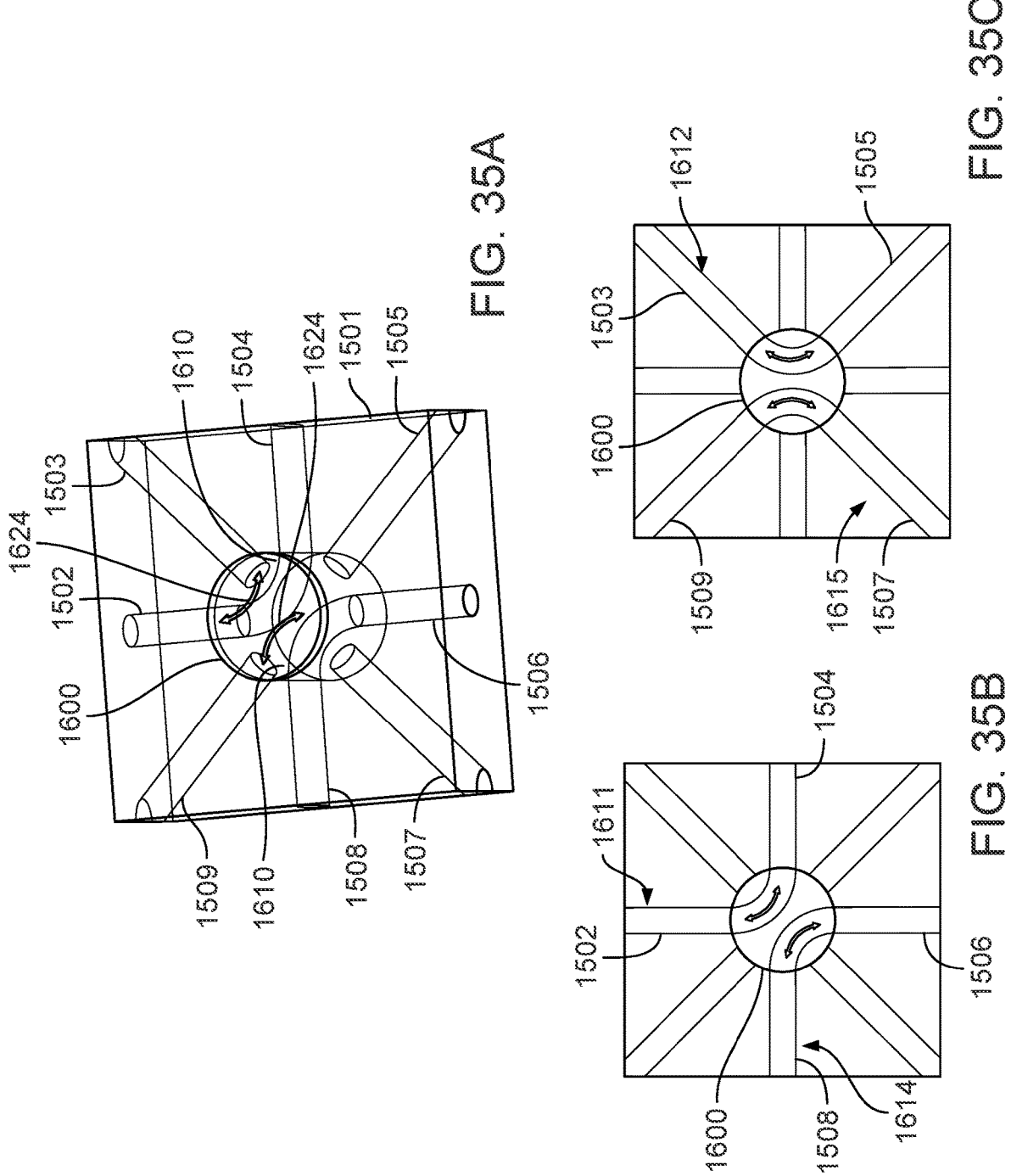
FIG. 35A is a perspective view of a rotary valve that enables dual fluid pathways of multiple sequential fluid pathways.
FIGS. 35B and 35C are top views of the rotary valve of FIG. 35A in rotational positions that enables two of the multiple sequential fluid pathways of FIG. 35A.
Figures 36, 37, 38, 39:
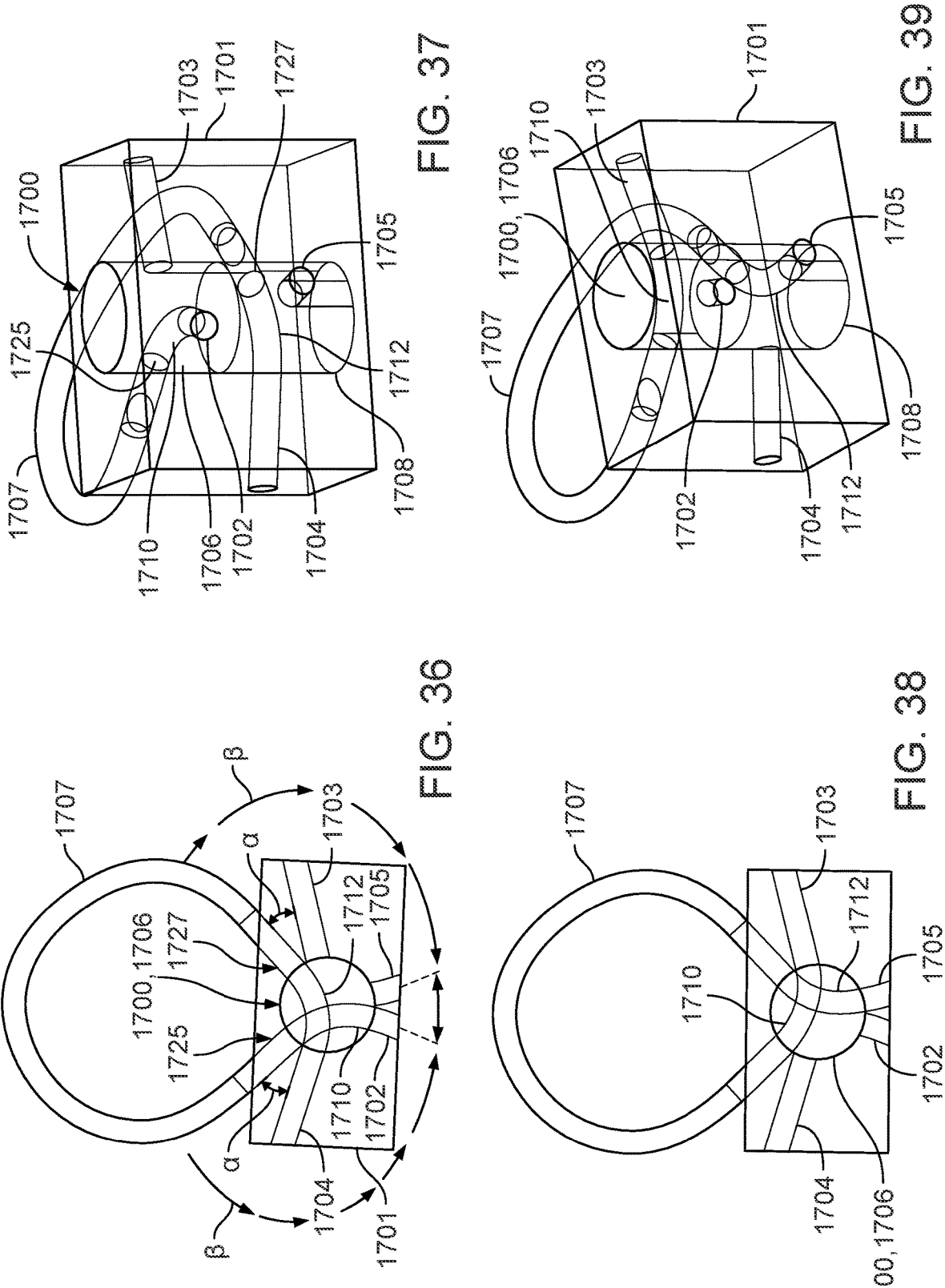
FIG. 36 is a top view of a rotary valve in a first configuration and including upper and lower fluid conduits for enabling a first fluid pathway at a fluid loop.
FIG. 37 is a perspective view of the rotary valve of FIG. 36 in the first configuration.
FIG. 38 is a top view of the rotary valve of FIG. 36 in a second configuration for enabling a second fluid pathway at the fluid loop.
FIG. 39 is a perspective view of the rotary valve of FIG. 36 in the second configuration.
Figures 40A, 40B, 40C, 40D, 41A, 41B, 41C, 41D:
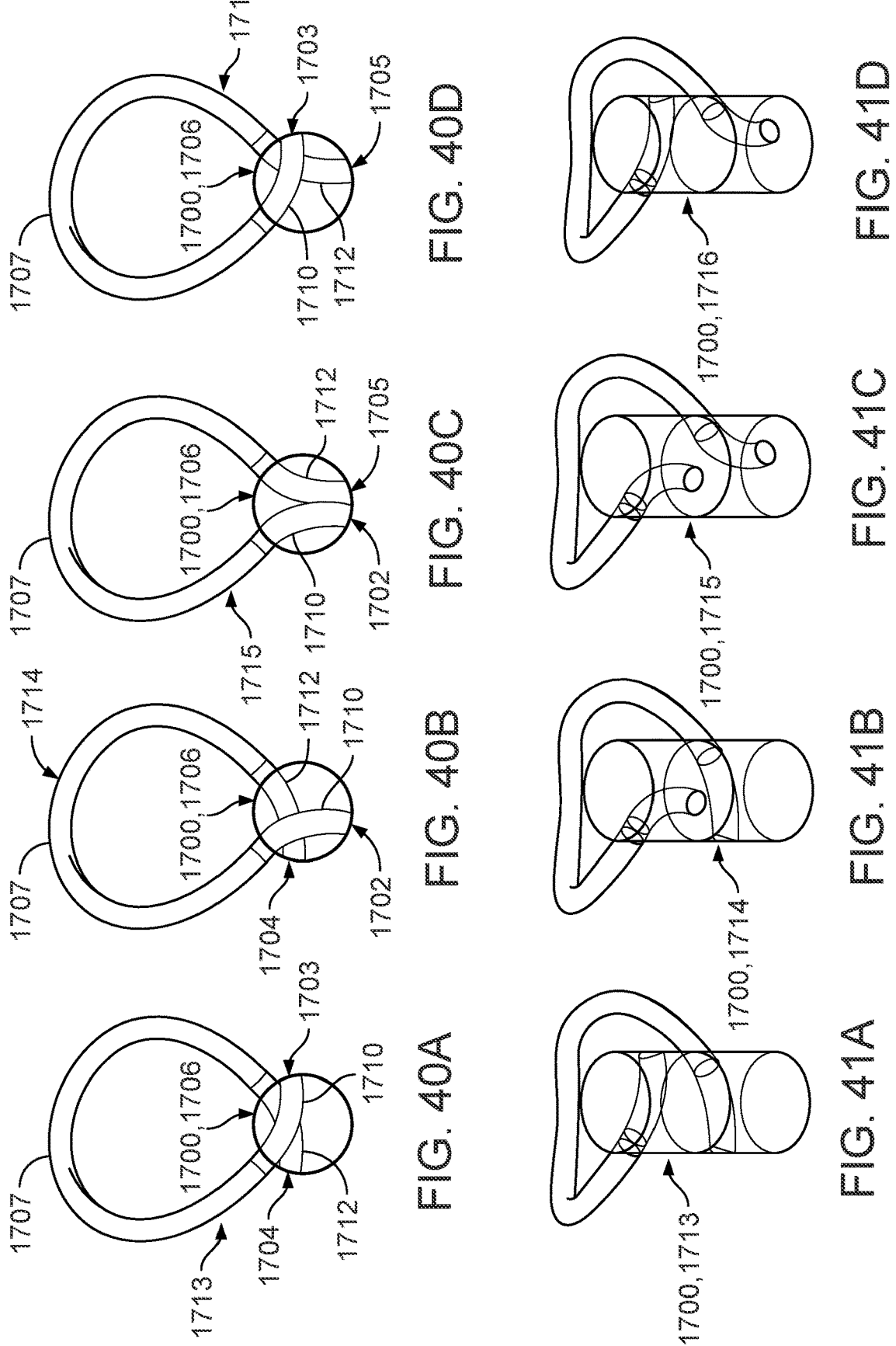
FIGS. 40A-40D are top views of the rotary valve of FIG. 36 in four different configurations for enabling respective fluid pathways at the fluid loop.
FIGS. 41A-41D are perspective views of the rotary valve of FIG. 36 in the four different configurations for enabling respective fluid pathways at the fluid loop.

In some embodiments, a rotary valve may include more than one internal fluid conduit for enabling activation of multiple fluid pathways within a fluid cassette. For example, FIGS. 35A-35C illustrate such a rotary valve 1600 installed within the fluid cassette 1501. In some embodiments, the rotary valve 1600 may be an embodiment of a valve 202 of the fluid conditioning system 100, and the fluid cassette 1601 may be an embodiment of the fluid cassette 102 of the fluid conditioning system 100. The rotary valve 1600 is substantially similar in construction and function to the rotary valve 1500, except for the inclusion of two internal fluid conduits 1610. Accordingly, the rotary valve 1600 has a generally cylindrical shape and defines a recessed profile (e.g., an actuation feature, not shown) along one end of the rotary valve 1600 by which an actuator can engage the rotary valve 1600 to rotate the rotary valve 1600.

The internal fluid conduits 1610 are designed to align simultaneously with alternating fluid lines 1502-1509 to define any two of eight sequential fluid paths, such that the other, six remaining fluid pathways are closed (e.g., blocked off or disabled) by a body of the rotary valve 1600. For example, a radius and a radial position of the internal fluid conduits 1610 are selected such that the internal fluid conduits 1610 can be rotationally positioned (e.g., upon rotation of the rotary valve 1600 at the recessed profile) to align with the fluid lines 1502, 1504 to define the fluid pathway 1611 and with the fluid lines 1506, 1508 to define the fluid pathway 1614; with the fluid lines 1503, 1505 to define the fluid pathway 1612 and with the fluid lines 1507, 1509 to define the fluid pathway 1615; with the fluid lines 1504, 1506 and with the fluid lines 1508, 1502 to define another pair of opposing fluid pathways (not indicated), and so on about a circumference of the rotary valve 1600. The rotary valve 1600 further defines visual indicators 1624 (e.g., illustrated schematically as curved arrows in FIGS.

35A-35C) that align with the selected fluid lines 1502-1509 to indicate that the selected fluid pathways are activated (e.g., open for fluid flow). In some embodiments, driving the rotary valve 1600 with a motor and an absolute encoder with a unique connection interface for coupling with the rotary valve 1600 can allow selection of two fluid pathways from eight different fluid pathways (e.g., with single-direction fluid flow) or from sixteen different fluid pathways (e.g., with bi-directional fluid flow) within a dialysis system.

In some embodiments, a rotary valve that is designed to service multiple fluid pathways distributed about a circumference of the rotary valve provides an inlet fluid conduit that is axially offset from an outlet fluid conduit. For example, FIGS. 36-39 illustrate such a rotary valve 1700 installed in a fluid cassette 1701 within a dialysis system. In some embodiments, the rotary valve 1700 may be an embodiment of a valve 202 of the fluid conditioning system 100, the fluid cassette 1701 may be an embodiment of the fluid cassette 102 of the fluid conditioning system 100, and such dialysis system may be an embodiment of the fluid conditioning system 100. In the example embodiment of FIGS. 36-39, the fluid cassette 1701 includes fluid lines 1702, 1703, 1704, 1705 that are positioned about a circumference of the rotary valve 1700. The fluid cassette 1701 also includes a fluid line 1707 (e.g., a fluid loop) that fluidly connects either of the fluid lines 1702, 1703 to either of the fluid lines 1704, 1705. Either of fluid lines 1702, 1703 may serve as an inlet line or an outlet line, while either of fluid lines 1704, 1705 may conversely serve as an outlet line or an inlet line, depending on a configuration of the rotary valve 1700.

The rotary valve 1700 has a generally cylindrical shape and includes an upper valve body 1706 and a lower valve body 1708 that are axially aligned. The upper valve body 1706 defines an upper fluid conduit 1710 that is formed (e.g., with an arcuate shape) to align simultaneously with an upper end 1725 of the fluid line 1707 and either the upper fluid line 1702 or the upper fluid line 1703, depending on a rotational position of the upper valve body 1706. The lower valve body 1708 defines a lower fluid conduit 1712 that is formed (e.g., with an arcuate shape) to align simultaneously with a lower end 1727 of the fluid line 1707 and either the lower fluid line 1704 or the lower fluid line 1705, depending on a rotational position of the lower valve body 1708.

Referring to FIGS. 40A-41D, a rotational configuration of the rotary valve 1700 can accordingly define any one of four alternative fluid paths 1713, 1714, 1715, 1716 such that the other, three remaining fluid pathways 1713, 1714, 1715, 1716 are closed (e.g., blocked off or disabled) by the upper and lower valve bodies 1706, 1708. For example, radii and radial positions of the upper and lower fluid conduits 1710, 1712 are selected such that the upper and lower fluid conduits 1710, 1712 can be rotationally positioned (e.g., upon rotation of the upper and lower valve bodies 1706, 1708 at recessed profiles) to align with the fluid lines 1703, 1707, 1704 to define the fluid pathway 1713; with the fluid lines 1702, 1707, 1704 to define the fluid pathway 1714; with the fluid lines 1702, 1707, 1705 to define the fluid pathway 1715, and with the fluid lines 1703, 1707, 1705 to define the fluid pathway 1716. Referring again to FIG. 36, a fixed angle $\alpha$ is defined by the fluid line 1704 and a left side of the fluid line 1707 and is defined by the fluid line 1703 and a right side of the fluid line 1707. Similarly, a fixed angle $\beta$ is defined by the fluid line 1702 and a right side of the fluid line 1707 and is defined by the fluid line 1705 and a left side of the fluid line 1707.

Figure 42:
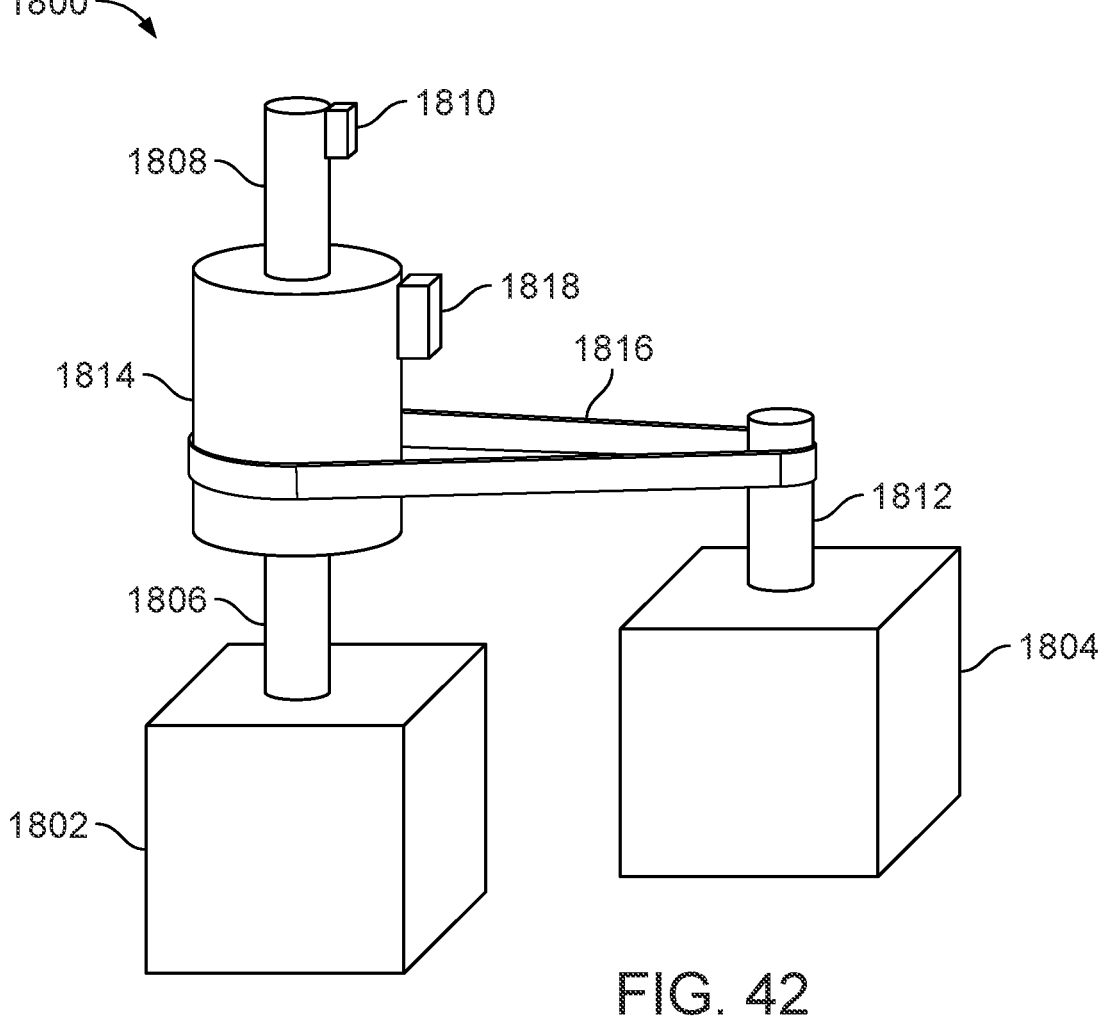
FIG. 42 is a perspective view of a drive assembly for adjusting a rotational configuration of the rotary valve of FIG. 11.

Referring to FIG. 42, the upper and lower valve bodies 1706, 1708 can be rotated independently of each other by a drive assembly 1800 of the dialysis system. In some embodiments, the drive assembly 1800 may be an embodiment of one or more of the actuator 125, the motor 129, and the drive unit 130 of the fluid conditioning system 100. The drive assembly 1800 includes a motor 1802 for rotating the upper valve body 1708 and a motor 1804 for rotating the lower valve body 1708. The motor 1802 is operable to rotate a drive shaft 1806 that is connected to a valve interface 1808. The valve interface 1808 includes a connection element 1810 by which the upper valve body 1706 can be coupled to the motor 1802. The motor 1804 is operable to rotate a drive shaft 1812 that is connected to a valve interface 1814 via a drive belt 1816. The valve interface 1814 includes a connection element 1818 by which the lower valve body 1708 can be coupled to the motor 1804. The rotary valve 1700 further defines visual indicators (not shown) that align with the upper and lower fluid conduits 1710, 1712 to indicate activation of a selected fluid pathway 1713, 1714, 1715, 1716. In some embodiments, driving the rotary valve 1700 with the motors 1802, 1804 and absolute encoders with unique connection interfaces for coupling with the rotary valve 1700 at the connection elements 1810, 1818 can allow selection from two different independent fluid pathways (e.g., with single-direction fluid flow) or from four different independent fluid pathways (e.g., with bi-directional fluid flow) for a pump fluid loop within a dialysis system.

As discussed above with respect to the rotary valve 1100, a capability of the rotary valves 1200, 1300, 1400, 1500, 1600, 1700 to service multiple fluid pathways of a dialysis fluid cassette allows a design of a dialysis fluid cassette to be simplified as compared to conventional dialysis fluid cassettes that require a dedicated valve for each fluid pathway. Accordingly, a cassette including any of the above-discussed rotary valves can include a relatively reduced total number of valves, which can result in a reduced total heat generation within a dialysis system, a reduced cost of the dialysis system, a reduced size of a footprint of the cassette, and a reduced amount of hardware electronics within the dialysis system.

For example, while the fluid conditioning system 100 has been described and illustrated as including the pressure transducers 119 (PT1, PT2, PT3, PT4) for regulating pump flow rates, in some embodiments, a fluid conditioning system that is otherwise similar in construction and function to the fluid conditioning system 100 may alternatively include flow meters instead of pressure transducers for regulating pump flow rates. In some embodiments, a fluid conditioning system that is otherwise similar in construction and function to the fluid conditioning system 100 may not include pressure transducers or flow meters and may instead be RPM-controlled based on a detailed knowledge of the system operation to regulate pump flow rates.

While the fluid conditioning system 100 has been described and illustrated as including peristaltic pumps 103, 104 (P1, P2, P3, P4), in some embodiments, a fluid conditioning system that is otherwise similar in construction and function to the fluid conditioning system 100 may alternatively include a different type of pump, such as an impeller pump, a linear displacement pump, positive displacement pump, or a centrifugal pump.

While the fluid conditioning system 100 has been described and illustrated as including one overflow reservoir (e.g., the secondary reservoir 305), in some embodiments, a fluid conditioning system that is otherwise similar in construction and function to the fluid conditioning system 100 may include one or more additional overflow reservoirs. For example, in some embodiments, an additional reservoir may be connected to the fluid circuit 350 upstream of pump P1 or downstream of pump P2. In some embodiments, an additional reservoir may have a capacity different than that of either reservoir 304 or reservoir 305 or may have a zero volume capacity. In some embodiments, a reservoir may be permanently connected to a drain.

While the heater bag 153 has been described and illustrated as being arranged downstream of pump P2 of the fluid conditioning system 100, in some embodiments, a fluid conditioning system that is otherwise similar in construction and function to the fluid conditioning system 100 may include a heater bag or other heating element that is arranged at a different location along the fluid circuit 350 in order to achieve optimal temperature control of fluid flowing through the fluid circuit 350. For example, in some embodiments, a heater bag may be positioned immediately downstream of the sorbent cartridge 303 and may be powered based on signals from temperature sensor T1 to ensure that the temperature of the dialysis fluid is not high enough to damage internal components of the sorbent cartridge 303. In some embodiments, a heater bag may be located along the fluid circuit 350 anywhere between valve V1 and valve V2, as advantageous (e.g., to promote dissolution of the dry chemicals in the supply bags 306, 307, 309).

While the fluid conditioning system 100 has been described as including three-way valves V1-V7, in some embodiments, a fluid conditioning system that is otherwise similar in construction and function to the fluid conditioning system 100 may alternatively include one or more two-way valves to achieve the fluid flow path scenarios discussed above.

While an operation of the fluid conditioning system 100 has been described and illustrated with respect to certain flow rates, fluid volumes, temperatures, pressures, and time periods, in some embodiments, the fluid conditioning system 100 may be operated to carry out a fluid conditioning cycle with one or more different flow rates, fluid volumes, temperatures, pressures, and time periods, while still functioning to adequately condition dialysate for use in a cooperating dialysis system.

Although the example control system 161, the example hardware system 500, and the example software system 600 have been described respectively in FIGS. 23-25, implementations of the subject matter and the functional operations described above can be implemented in other types of digital electronic circuitry, or in computer software, firmware, or hardware, including the structures disclosed in this specification and their structural equivalents, or in combinations of one or more of them.

Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described in detail above. However, various modifications to these embodiments may be made without departing from the spirit and scope of the above disclosures. Other embodiments are also within the scope of the following claims.

What is claimed is:

1. A system comprising:
a blood treatment machine;
a dialyzer configured to be coupled to the blood treatment machine, the dialyzer comprising:
  a dialyzer housing defining a blood inlet and a blood outlet;
  a bundle of hollow fibers within an interior of the dialyzer housing;
  a pumping device drivable to force blood received from the blood inlet through lumens of the bundle of hollow fibers and out the blood outlet;
  a dialysate inlet port in fluid communication with a dialysate flow path that includes space in the interior of the dialyzer housing between the bundle of hollow fibers; and
  a dialysate outlet port in fluid communication with the dialysate flow path; and
a fluid conditioning system comprising a dialysis fluid cassette, the dialysis fluid cassette comprising:
  an inlet fluid line;
  a plurality of outlet fluid lines; and a valve comprising an actuation feature by which the valve can be rotated to fluidly communicate the inlet fluid line with a selected fluid line of the plurality of outlet fluid lines,
wherein the fluid conditioning system is configured to (i) prepare and supply fresh dialysate to the dialyzer via the dialysate inlet port, and (ii) receive spent dialysate from the dialyzer via the dialysate outlet port, recycle the spent dialysate, and supply the recycled dialysate to the dialyzer via the dialysate inlet port.

2. The system of claim 1, wherein the fluid conditioning system is a standalone unit configured to be connected via fluid lines to the blood treatment machine.

3. The system of claim 1, wherein the fluid conditioning system is a standalone unit configured to be connected via fluid lines directly to the dialyzer.

4. The system of claim 1, wherein the fluid conditioning system is part of the blood treatment machine.

5. The system of claim 1, wherein the actuation feature of the dialysis fluid cassette comprises a surface profile that is formed to be engaged by an actuator for rotating the valve.

6. The system of claim 1, wherein the actuation feature of the dialysis fluid cassette has a polygonal shape.

7. The system of claim 1, wherein the valve of the dialysis fluid cassette further comprises:
a valve body defining an internal fluid pathway that can fluidly communicate the inlet fluid line with the selected fluid line; and
a spring that is configured to move the valve body to enable or disable an operation of the valve.

8. The system of claim 7, wherein the valve body of the dialysis fluid cassette is movable to:
a first position at which the internal fluid pathway is aligned with the inlet fluid line and the plurality of outlet fluid lines to enable the operation of the valve, and
a second position at which the internal fluid pathway is offset from the inlet fluid line and the plurality of outlet fluid lines to disable the operation of the valve.

9. The system of claim 1, wherein the dialysis fluid cassette further comprises a plurality of inlet fluid lines that includes the inlet fluid line, wherein the valve comprises a valve body defining an internal fluid conduit that can fluidly communicate the inlet fluid line of the plurality of inlet fluid lines with the selected fluid line of the plurality of outlet fluid lines to define a fluid pathway of a plurality of fluid pathways within the dialysis fluid cassette.

10. The system of claim 9, wherein the internal fluid conduit is a first internal fluid conduit, the inlet fluid line is a first selected inlet fluid line, the selected fluid line is a first selected outlet fluid line, and the fluid pathway is a first fluid pathway, the valve body further defining a second internal fluid conduit that can fluidly communicate a second selected inlet fluid line of the plurality of inlet fluid lines with a second selected outlet fluid line of the plurality of outlet fluid lines to define a second fluid pathway of the plurality of fluid pathways within the dialysis fluid cassette.

11. The system of claim 1, wherein the dialyzer further comprises a first end cap that defines the blood inlet and a second end cap that defines the blood outlet.

12. The system of claim 11, wherein the dialyzer further comprises a venous pressure detection chamber arranged between the bundle of hollow fibers and the blood outlet, the venous pressure detection chamber comprising a first flexible surface attached to the second end cap.

13. The system of claim 11, wherein the dialyzer further comprises an arterial pressure detection chamber arranged between the blood inlet and the bundle of hollow fibers, the arterial pressure detection chamber having a second flexible surface attached to the first end cap.

14. The system of claim 11, wherein the first end cap defines the dialysate outlet port and the second end cap defines the dialysate inlet port.

15. The system of claim 11, wherein the first end cap defines a substituate liquid inlet port in fluid communication with the lumens of the bundle of hollow fibers.

16. The system of claim 11, wherein the second end cap defines a substituate liquid outlet port in fluid communication with the lumens of the bundle of hollow fibers.

17. The system of claim 11, wherein the pumping device comprises a pump rotor within the first end cap.

18. The system of claim 17, wherein the dialyzer further comprises one or more magnets encased within the pump rotor, the pump rotor being magnetically-drivable to force blood through the lumens of the hollow fibers.

19. The system of claim 18, wherein the dialyzer further comprises one or more magnets attached to the pump rotor, the pump rotor being magnetically-drivable to force blood through the lumens of the hollow fibers.

20. The system of claim 17, wherein the pump rotor is magnetically levitated during operation.

21. The system of claim 17, wherein the dialyzer housing comprises a deaeration chamber.

22. The system of claim 21, wherein the deaeration chamber is defined in an end cap of the dialyzer housing.

23. The system of claim 1, wherein the pumping device is contained at a fixed location relative to the hollow fibers.

* * * * *